US011298405B2

(12) United States Patent
Brockmeyer et al.

(10) Patent No.: US 11,298,405 B2
(45) Date of Patent: Apr. 12, 2022

(54) PRE-FILLED PHARMACEUTICAL PACKAGE COMPRISING A LIQUID FORMULATION OF A VEGF-ANTAGONIST

(71) Applicants: FORMYCON AG, Martinsried/Planegg (DE); SIO2 MEDICAL PRODUCTS, INC., Auburn, AL (US); KLINGE BIOPHARMA GMBH, Holzkirchen (DE)

(72) Inventors: Carsten Brockmeyer, Marzling (DE); Christopher Weikart, Auburn, AL (US); Murray Stephen Bennett, Bellingham, WA (US); Jean-Pierre Giraud, Auburn, AL (US); Thomas Strungmann, Munich (DE)

(73) Assignees: FORMYCON AG (DE); SIO2 MEDICAL PRODUCTS, INC., Auburn, AL (US); KLINGE BIOPHARMA GMBH (DE)

( * ) Notice: Subject to any disclaimer, the term of this patent is extended or adjusted under 35 U.S.C. 154(b) by 0 days.

(21) Appl. No.: 17/154,702

(22) Filed: Jan. 21, 2021

(65) Prior Publication Data

US 2021/0220435 A1 Jul. 22, 2021

Related U.S. Application Data

(63) Continuation of application No. 15/777,276, filed as application No. PCT/US2016/062767 on Nov. 18, 2016, now Pat. No. 10,925,927.

(Continued)

(51) Int. Cl.
*A61K 38/17* (2006.01)
*A61K 39/395* (2006.01)
(Continued)

(52) U.S. Cl.
CPC .......... *A61K 38/179* (2013.01); *A61K 9/0019* (2013.01); *A61K 39/39591* (2013.01);
(Continued)

(58) Field of Classification Search
CPC ............ A61K 38/179; A61K 39/39591; A61K 9/0019; A61M 5/3129; A61M 2005/3131
See application file for complete search history.

(56) References Cited

U.S. PATENT DOCUMENTS 4,184,593 A 1/1980 Dorr
4,294,695 A 9/1981 Bekkering et al.
(Continued)

FOREIGN PATENT DOCUMENTS

DE 102009023335 A1 12/2010
EP 0649318 4/1995
(Continued)

OTHER PUBLICATIONS

Bakri et al., "Intravitreal Silicone Oil Droplets After Intravitreal Drug Injections", Retina, vol. 28, pp. 996-1001 (2008).
(Continued)

*Primary Examiner* — Michael C Miggins
(74) *Attorney, Agent, or Firm* — McAndrews, Held & Malloy, Ltd.

(57) ABSTRACT

A pre-filled pharmaceutical package comprising a liquid formulation of a VEGF-antagonist, for example Ranibizumab, in a pre-filled pharmaceutical package, for example a syringe, cartridge, or vial, made in part or in whole of a thermoplastic polymer, coated on the interior with a tie coating or layer, a barrier coating or layer, a pH protective coating or layer, and optionally a lubricity coating or layer. Stability performance of the VEGF-antagonist packaged in the coated COP vessel comparable to or better than glass was obtained.

19 Claims, 14 Drawing Sheets

Related U.S. Application Data

(60) Provisional application No. 62/257,210, filed on Nov. 18, 2015.

(51) Int. Cl.
*A61K 9/00* (2006.01)
*C07K 16/22* (2006.01)
*A61M 5/31* (2006.01)
*A61K 45/06* (2006.01)

(52) U.S. Cl.
CPC .......... *A61M 5/3129* (2013.01); *C07K 16/22* (2013.01); *A61K 45/06* (2013.01); *A61K 2300/00* (2013.01); *A61M 2005/3131* (2013.01); *C07K 2317/24* (2013.01); *C07K 2317/55* (2013.01); *C07K 2317/76* (2013.01); *C07K 2319/30* (2013.01)

(56) References Cited

U.S. PATENT DOCUMENTS

| | | |
|---|---|---|
| 4,424,057 A | 1/1984 | House |
| 4,820,278 A | 4/1989 | Balisky |
| 4,846,801 A | 7/1989 | Okuda et al. |
| 4,874,381 A | 10/1989 | Vetter |
| 4,986,820 A | 1/1991 | Fischer |
| 5,069,670 A | 12/1991 | Vetter et al. |
| RE34,845 E | 1/1995 | Vetter et al. |
| 5,731,144 A | 3/1998 | Toothman et al. |
| 5,731,424 A | 3/1998 | Toothman et al. |
| 6,124,449 A | 9/2000 | Gold et al. |
| 6,207,816 B1 | 3/2001 | Gold et al. |
| 6,582,959 B2 | 6/2003 | Kim |
| 6,703,020 B1 | 3/2004 | Thorpe et al. |
| 7,985,188 B2 | 7/2011 | Felts et al. |
| 8,067,070 B2 | 11/2011 | Klein et al. |
| 9,192,725 B2 | 11/2015 | Kawamura |
| 9,340,594 B2 | 5/2016 | Furfine et al. |
| 2003/0190317 A1 | 10/2003 | Baca et al. |
| 2004/0231926 A1 | 11/2004 | Sakhrani et al. |
| 2008/0228147 A1 | 9/2008 | David-Hegerich et al. |
| 2008/0262435 A1 | 10/2008 | Erickson et al. |
| 2010/0270335 A1 | 10/2010 | Pa |
| 2012/0003497 A1 | 1/2012 | Handy et al. |
| 2014/0012227 A1 | 1/2014 | Sigg et al. |
| 2016/0067405 A1 | 3/2016 | Matusch |

FOREIGN PATENT DOCUMENTS

| | | |
|---|---|---|
| EP | 0666868 | 8/1995 |
| EP | 0764450 A1 | 3/1997 |
| EP | 0882467 A2 | 12/1998 |
| EP | 0649318 B1 | 3/1999 |
| EP | 0882467 A3 | 10/1999 |
| EP | 0764450 B1 | 8/2002 |
| EP | 0882467 B1 | 10/2003 |
| EP | 2251455 A2 | 11/2010 |
| EP | 1539065 B1 | 12/2012 |
| EP | 2601991 B1 | 1/2016 |
| GB | 2500092 A | 9/2013 |
| JP | 2005073930 | 3/2005 |
| JP | 2013541375 | 11/2013 |
| JP | 2014028114 | 2/2014 |
| RU | 2550452 C2 | 5/2015 |
| WO | 9410202 A1 | 5/1994 |
| WO | 9426334 A1 | 11/1994 |
| WO | 9630046 A1 | 10/1996 |
| WO | 9845331 A2 | 10/1998 |
| WO | 9845332 A2 | 10/1998 |
| WO | 0075319 A1 | 12/2000 |
| WO | 2005044853 A2 | 5/2005 |
| WO | 2009099641 A2 | 8/2009 |
| WO | 2009155724 A2 | 12/2009 |
| WO | 2010060748 A1 | 6/2010 |
| WO | 2011117878 A1 | 9/2011 |
| WO | 2011135067 A1 | 11/2011 |
| WO | 2012044744 | 4/2012 |
| WO | 2013063275 | 5/2013 |
| WO | 2014005728 A1 | 1/2014 |
| WO | 2014052792 A1 | 4/2014 |
| WO | 2014085346 A1 | 6/2014 |
| WO | 2014085348 A2 | 6/2014 |
| WO | 2014144926 | 9/2014 |
| WO | 2014164928 | 10/2014 |
| WO | 2015054075 | 4/2015 |
| WO | 2015071348 A1 | 5/2015 |
| WO | 2015173260 A1 | 11/2015 |
| WO | 2018123276 A1 | 7/2018 |

OTHER PUBLICATIONS

Bell et al., "Oligonucleotide NX1838 Inhibits VEGF165 Mediated Cellular Responses in vitro", In Vitro Cell. Div. Biol.-Animal, vol. 35, pp. 533-542 (1999).

Chen et al., "Selection and Analysis of an Optimized Anti-VEGF Antibody: Crystal Structure of an Affinity-matured Fab n Complex with Antigen", J. Mol. Biol., vol. 293, pp. 865-881 (1999).

Green et al., "Inhibitory DNA Ligands to Platelet-Derived Growth Factor B-Chain", Biochemistry, vol. 35, pp. 14413-14424 (1996).

Holash et al., "VEGF-Trap: A VEGF blocker with potent antitumor effects", PNAS, vol. 99, No. 17, pp. 11393-11398 (2002).

Johnson et al., "Ocular and Systemic Safety of Bevacizumab and Ranibizumab in Patients with Neovascular Age-Related Macular Degeneration", Curr. Opin. Ophthalmol., vol. 24, pp. 205-212 (2013).

Liu et al., "Root Cause Analysis of Tungsten-Induced Protein Aggregation in Pre-Filled Syringes", PDA J. Pharm. Sci. and Tech., vol. 64, pp. 11-19 (2010).

Popkov et al., "Human/Mouse Cross-Reactive Anti-VEGF Receptor 2 Recombinant Antibodies Selected from an immune b9 Allotype Rabbit Antibody Library", Journal of Immunological Methods, vol. 288, pp. 149-164 (2004).

Pryce Lewis et al., "HWCVD of Polymers: Commercialization and Scale-Up", Thin Solid Films, vol. 517, pp. 3551-3554 (2009).

Seidl et al., "Tungsten-Induced Denaturation and Aggregation of Epoetin Alfa During Primary Packaging as a Cause of Immunogenicity", Pharm. Res., vol. 29, pp. 1454-1467 (2012).

Wolgemuth, "Challenges with Prefilled Syringes: The Parylene Solution", www.ondrugdelivery.com, pp. 44-45 (2012).

International Search Report for PCT/US2016/062767, dated Feb. 8, 2017.

PRE-FILLED PHARMACEUTICAL PACKAGE COMPRISING A LIQUID FORMULATION OF A VEGF-ANTAGONIST

This application is a continuation of U.S. patent application Ser. No. 15/777,276, filed on May 18, 2018, which is a U.S. National Phase of International Application No. PCT/US2016/062767, filed Nov. 18, 2016, which claims priority to U.S. Provisional Patent Application No. 62/257,210, filed Nov. 18, 2015, all of which are incorporated herein by reference in their entireties.

The entire specification and all the drawings of each of the following patent applications is incorporated here by reference to provide continuity of disclosure: U.S. Provisional Applications 61/776,733, filed Mar. 11, 2013, and 61/800,746, filed Mar. 15, 2013; U.S. Pat. No. 7,985,188; PCT Application PCT/US14/23813, filed Mar. 11, 2014; and published PCT Publ. Appl. WO2014085348 (A2), WO2014164928 (A1), WO2014/005728 A1, and WO2015/071,348. The entire specification and all the drawings of each of these applications are incorporated here by reference to provide continuity of disclosure.

FIELD OF THE INVENTION

The present invention relates generally to liquid formulations of VEGF-antagonists in pre-filled pharmaceutical packages, for example pre-filled syringes, for intravitreal injection (injection of medication into the vitreous body of the eye). Such pharmaceutical packages are suitable for storage and intravitreal administration of liquid formulations of drugs, for example VEGF-antagonists, for example Ranibizumab, Aflibercept, or Bevacizumab.

BACKGROUND OF THE INVENTION

Ocular diseases such as age-related macular degeneration and diabetic macular oedema are caused by the uncontrolled growth of blood vessels in the eye. Hence, one option to treat these and similar diseases is to inhibit angiogenesis in the eye. Since VEGF is a key factor in the stimulation of angiogenesis, it is an attractive target for down-regulating angiogenesis. Many treatments for these and other ocular diseases require intravitreal injection of liquid pharmaceutical formulations.

The term "intravitreal injection" refers to the administration of a pharmaceutical composition in which the substance is injected directly into the eye. More specifically, the substance is injected into the vitreous humour (also called vitreous body or simply vitreous) which is the clear gel that fills the space between the lens and the retina of the eyeball of humans and other vertebrates.

WO 2014005728 A1 discloses pre-filled syringes containing a VEGF-antagonist; the syringes have low silicone oil content. The whole disclosure of this document is focused on the use of glass syringes and therefore teaches that a low amount of silicone oil has to be present within the syringe.

Currently, LUCENTIS® (Ranibizumab injection) is an approved drug in the United States and Europe for intravitreal injection, for example for treatment of diabetic macular oedema. It is available packaged in glass vials. Recently, a pre-filled Ranibizumab syringe has been approved by the European Medicines Agency (EMA). The syringe barrel consists of borosilicate glass which is spray-coated with silicon oil-in-water emulsion and subsequently heat-fixed (so-called "baked silicone") (poster presentation by Clunas et al. at the 5th World Congress on Controversies in Ophthalmology, Mar. 20-23, 2014; poster presentation of Michaud et al. at the ARVO Annual Meeting 2014).

Pre-filled syringes have many benefits compared to a vial and a separately provided syringe, such as improved convenience, affordability, accuracy, sterility, and safety. The use of pre-filled syringes results in greater dose precision, in a reduction of the potential for needle stick injuries that can occur while drawing medication from vials, in pre-measured dosage reducing dosing errors due to the need to reconstitute and/or draw medication into a syringe, and in less overfilling of the syringe helping to reduce costs by minimizing drug waste.

The traditional glass pharmaceutical packages, including pre-filled syringes, are prone to breakage or degradation during manufacture, filling operations, shipping and use, which means that glass particulates may enter the drug.

Further, glass pre-filled syringes have been treated with silicone, in processes generally known as siliconization, to enable the correct movement of the stopper within the glass barrel and thereby allow effective and accurate drug delivery. Siliconization of the traditional glass pharmaceutical packages has been used to facilitate insertion of a stopper into the package, or to advance a plunger through a syringe to dispense the drug. Siliconization, however, may result in introduction of silicone particles into the drug. This problem has been observed whether using the traditional coating of silicone oil or a baked-on silicone coating. Also, glass syringes such as the approved Ranibizumab pre-filled syringe have a relatively large weight compared to plastic syringes.

When administering a drug intravitreally, it is extremely important to minimize the introduction of particles into the vitreous body of the eye, which may be seen as floaters or otherwise interfere with the patient's vision. The standards limiting the amount and size of particles in formulations for intravitreal injection—for example USP789 or Ph. Eur. 5.7.1—are stringent. Nonetheless, it has been shown that silicone droplets occur in the vitreous cavity after intravitreal administration of VEGF-antagonists, and it was hypothesized that the silicone is derived from the needles and syringes used for the injections (Bakri and Ekdawi (2008) Retina 28: 996-1001).

Additionally, the glue which is necessary to attach a staked-in needle to a glass syringe can lead to impurities or increased protein oxidation (presentation of Adler at the 2011 PDA Europe The Universe of Pre-Filled Syringes and Injection Devices, Basel, 7-11 Nov. 2011; presentation of Markovic at the PDA Single Use Systems Workshop, Bethesda, 22-23 Jun. 2011).

Further, during the manufacturing of glass pre-fillable syringes, usually tungsten pins are used. It has been shown that soluble tungsten found in pre-filled glass syringes leads to protein aggregation and protein oxidation (Liu et al. (2010) PDA J. Pharm. Sci. Technol. 64(1): 11-19; Seidl et al. (2012) Pharm. Res. 29: 1454-1467).

Several non-glass pre-filled syringes have been described. WO 2011/117878 A1 discloses a polycarbonate syringe. WO 2009/099641 A2 discloses cyclic olefin polymer syringes.

Pre-filled syringes for intravitreal injection typically are usually terminally sterilized using oxidizing gases such as ethylene oxide to reduce the risk of microbial infection of the eye. Syringe barrels made from plastic typically have not been suitable for terminal sterilization because the plastic is permeable by the gases used for sterilization. Gases which enter into the pre-filled syringe may chemically react with the drug contained in the syringe and may thus significantly reduce the stability of the drug.

SUMMARY OF THE INVENTION

An aspect of the invention is a liquid formulation of a VEGF-antagonist, for example Ranibizumab, Aflibercept, or Bevacizumab, in a pre-filled pharmaceutical package. The pre-filled pharmaceutical package includes a wall, a coating set on the interior surface of the wall defining a lumen, a liquid formulation of a VEGF-antagonist in the lumen, and a closure closing the lumen having a front face having a fluoropolymer lubricity coating or layer facing the liquid formulation.

Another aspect of the invention is a pre-filled pharmaceutical package containing a liquid formulation of a VEGF-antagonist, for example Ranibizumab, Aflibercept, or Bevacizumab. The pre-filled pharmaceutical package includes a wall, a coating set on the interior surface of the wall defining a lumen and a liquid formulation of a VEGF-antagonist in the lumen.

The wall can be made in part or in whole of a cyclic olefin polymer (COP) having an interior surface enclosing at least a portion of a lumen.

The coating set includes a tie coating or layer, a barrier coating or layer, a pH protective coating or layer, and optionally a lubricity coating or layer.

The tie coating or layer is deposited on the wall interior surface. The tie coating or layer can have the empirical formula $SiO_xC_yH_z$, in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS).

The barrier coating or layer can have the empirical formula $SiO_x$, in which x is from about 1.5 to about 2.9 as measured by XPS. The barrier coating or layer can be positioned between the tie coating or layer and the lumen.

The pH protective coating or layer can have the empirical formula $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS. The pH protective coating or layer can be positioned between the barrier coating or layer and the lumen.

Some embodiments of the present invention relate to any one of the items below, in which numbers expressed using Arabic numerals optionally can be substituted for the corresponding numbers expressed here in Roman numerals, with the same meaning.

Item I is a liquid formulation of Ranibizumab, Aflibercept, or Bevacizumab in a pre-filled pharmaceutical package comprising: a wall comprising a cyclic olefin polymer (COP) having an interior surface enclosing at least a portion of a lumen; a tie coating or layer on the wall interior surface comprising $SiO_xC_yH_z$, in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS); a barrier coating or layer of $SiO_x$, in which x is from about 1.5 to about 2.9 as measured by XPS, the barrier coating or layer positioned between the tie coating or layer and the lumen; a pH protective coating or layer of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS, positioned between the barrier coating or layer and the lumen; a liquid formulation of Ranibizumab, Aflibercept, or Bevacizumab in the lumen; and a closure closing the lumen having a front face having a fluoropolymer lubricity coating or layer facing the liquid formulation.

Item II is a liquid formulation of Ranibizumab, Aflibercept, or Bevacizumab in a pre-filled pharmaceutical package according to item I, comprising a liquid formulation of Ranibizumab in the lumen.

Item III is a liquid formulation of Ranibizumab, Aflibercept, or Bevacizumab in a pre-filled pharmaceutical package according to item II, in which the liquid formulation of Ranibizumab in the lumen comprises Ranibizumab at a concentration of 6 or 10 mg/ml, optionally administered in a volume of 0.05 mL.

Item IV is a liquid formulation of Ranibizumab, Aflibercept, or Bevacizumab in a pre-filled pharmaceutical package according to item III, in which the liquid formulation of Ranibizumab in the lumen further comprises: a buffer in an amount effective to provide a pH of the liquid formulation in the range from about 5 to about 7; a non-ionic surfactant in the range of 0.005 to 0.02 mg./mL of complete formulation, and water for injection.

Item V is a liquid formulation of Ranibizumab, Aflibercept, or Bevacizumab in a pre-filled pharmaceutical package according to item III, in which the liquid formulation of Ranibizumab in the lumen comprises, per mL of formulation:
  6 or 10 mg. Ranibizumab;
  100 mg. α,α-trehalose dihydrate;
  1.98 mg. L-histidine;
  0.1 mg Polysorbate 20; and
  water for injection qs to 1 mL.

Item VI is a liquid formulation of Ranibizumab, Aflibercept, or Bevacizumab in a pre-filled pharmaceutical package according to item III, in which the liquid formulation of Ranibizumab in the lumen comprises, per mL of formulation:
  6 or 10 mg. Ranibizumab;
  100 mg. α,α-trehalose dihydrate;
  1.98 mg. L-histidine;
  0.1 mg Polysorbate 20; and
  water for injection qs to 1 mL;
  adjusted to pH 5.5 with HCl.

Item VII is a liquid formulation of Ranibizumab, Aflibercept, or Bevacizumab in a pre-filled pharmaceutical package according to item III, in which the liquid formulation of Ranibizumab in the lumen comprises, per mL of formulation:
  6 or 10 mg. Ranibizumab;
  100 mg. α,α-trehalose dihydrate;
  0.32 mg. L-histidine
  1.66 mg. L-histidine hydrochloride monohydrate;
  mg Polysorbate 20; and
  water for injection qs to 1 mL Item VIII is a liquid formulation of Ranibizumab, Aflibercept, or Bevacizumab in a pre-filled pharmaceutical package according to item I, comprising a liquid formulation of Aflibercept in the lumen.

Item IX is a liquid formulation of Ranibizumab, Aflibercept, or Bevacizumab in a pre-filled pharmaceutical package according to item VIII, in which the liquid formulation of Aflibercept in the lumen comprises Aflibercept at a concentration of 40 mg/ml, optionally administered in a volume of 0.05 mL.

Item X is a liquid formulation of Ranibizumab, Aflibercept, or Bevacizumab in a pre-filled pharmaceutical package according to item 1, comprising a liquid formulation of Bevacizumab in the lumen.

Item XI is a liquid formulation of Ranibizumab, Aflibercept, or Bevacizumab in a pre-filled pharmaceutical package according to item X, in which the liquid formulation of Bevacizumab in the lumen comprises Bevacizumab at a concentration of 25 mg/ml, optionally administered in a volume of 0.05 mL.

Item XII is a liquid formulation of Ranibizumab, Aflibercept, or Bevacizumab in a pre-filled pharmaceutical package according to any one of the preceding items, in which the liquid formulation is contained in a pre-filled pharmaceutical package having a nominal maximum fill volume of 0.5 or 1 mL.

Item XIII is a liquid formulation of Ranibizumab, Aflibercept, or Bevacizumab in a pre-filled pharmaceutical package according to any one of the preceding items, in which the package is a vial or a cartridge.

Item XIV is a liquid formulation of Ranibizumab, Aflibercept, or Bevacizumab in a pre-filled pharmaceutical package according to any one of the preceding items, in which the package is a syringe and the stopper is a plunger slidable along the wall to deliver contents.

Item XV is a liquid formulation of Ranibizumab, Aflibercept, or Bevacizumab in a pre-filled pharmaceutical package according to item XIV, in which the plunger comprises a side surface slidable along the wall.

Item XVI is a liquid formulation of Ranibizumab, Aflibercept, or Bevacizumab in a pre-filled pharmaceutical package according to item XV, in which at least a portion of the side surface comprises a fluoropolymer lubricity coating or layer abutting the wall.

Item XVII is a liquid formulation of Ranibizumab, Aflibercept, or Bevacizumab in a pre-filled pharmaceutical package according to any one of the preceding items, having a breakout force less than or equal to 10N for initiating travel of the stopper in the lumen.

Item XVIII is a liquid formulation of Ranibizumab, Aflibercept, or Bevacizumab in a pre-filled pharmaceutical package according to any one of the preceding items, having a plunger sliding force less than or equal to 10N for advancing the stopper in the lumen.

Item XIX is a liquid formulation of Ranibizumab, Aflibercept, or Bevacizumab in a pre-filled pharmaceutical package according to any one of the preceding items, in which the liquid formulation of Ranibizumab, Aflibercept, or Bevacizumab in the lumen forms an equal or smaller area % of basic decomposition species, after storage of the pharmaceutical package at 5° C. for three months, than a glass pharmaceutical package of the same volumetric capacity, internally coated with baked-on silicone.

Item XX is a liquid formulation of Ranibizumab, Aflibercept, or Bevacizumab in a pre-filled pharmaceutical package according to any one of the preceding items I-VII or XII-XIX, in which the VEGF-antagonist is Ranibizumab and the liquid formulation of Ranibizumab in the lumen forms an equal or smaller area % of acidic decomposition species, after storage of the pharmaceutical package at 5° C. for three months, than a glass pharmaceutical package of the same volumetric capacity, internally coated with baked-on silicone.

Item XXI is a liquid formulation of Ranibizumab, Aflibercept, or Bevacizumab in a pre-filled pharmaceutical package according to any one of the preceding items I-VII or XII-XX, in which the VEGF-antagonist is Ranibizumab and the liquid formulation of Ranibizumab in the lumen forms an equal or smaller area % of basic decomposition species, after storage of the pharmaceutical package at 25° C. and 60% relative humidity for three months, than a glass pharmaceutical package of the same volumetric capacity, internally coated with baked-on silicone.

Item XXII is a liquid formulation of Ranibizumab, Aflibercept, or Bevacizumab in a pre-filled pharmaceutical package according to any one of the preceding items I-VII or XII-XXI, in which the VEGF-antagonist is Ranibizumab and the liquid formulation of Ranibizumab in the lumen forms an equal or smaller area % of acidic decomposition species, after storage of the pharmaceutical package at 25° C. and 60% relative humidity for three months, than a glass pharmaceutical package of the same volumetric capacity, internally coated with baked-on silicone.

Item XXIII is a liquid formulation of Ranibizumab, Aflibercept, or Bevacizumab in a pre-filled pharmaceutical package according to any one of the preceding items I-VII or XII-XXII, in which the VEGF-antagonist is Ranibizumab and the liquid formulation of Ranibizumab in the lumen forms an equal or smaller area % of basic decomposition species, after storage of the pharmaceutical package at 40° C. and 75% relative humidity for three months, than a glass pharmaceutical package of the same volumetric capacity, internally coated with baked-on silicone.

Item XXIV is a liquid formulation of Ranibizumab, Aflibercept, or Bevacizumab in a pre-filled pharmaceutical package according to any one of the preceding items I-VII or XII-XXIII, in which the VEGF-antagonist is Ranibizumab and the liquid formulation of Ranibizumab in the lumen forms an equal or smaller area % of acidic decomposition species, after storage of the pharmaceutical package at 40° C. and 75% relative humidity for three months, than a glass pharmaceutical package of the same volumetric capacity, internally coated with baked-on silicone.

Item XXV is a liquid formulation of Ranibizumab, Aflibercept, or Bevacizumab in a pre-filled pharmaceutical package according to any one of the preceding items I-VII or XII-XXIV, in which the VEGF-antagonist is Ranibizumab and the liquid formulation of Ranibizumab in the lumen forms an equal or smaller area % of aggregates, after storage of the pharmaceutical package at 25° C. and 60% relative humidity for three months, than a glass pharmaceutical package of the same volumetric capacity, internally coated with baked-on silicone.

Item XXVI is a liquid formulation of Ranibizumab, Aflibercept, or Bevacizumab in a pre-filled pharmaceutical package preceding items I-VII or XII-XXV, in which the VEGF-antagonist is Ranibizumab and the liquid formulation of Ranibizumab in the lumen forms an equal or smaller area % of aggregates, after storage of the pharmaceutical package at 40° C. and 75% relative humidity for three months, than a glass pharmaceutical package of the same volumetric capacity, internally coated with baked-on silicone.

Item XXVII is a liquid formulation of Ranibizumab, Aflibercept, or Bevacizumab in a pre-filled pharmaceutical package according to any one of the preceding items I-VII or XII-XXVI, in which the VEGF-antagonist is Ranibizumab and the liquid formulation of Ranibizumab contains no more than 50 particles ≥10 μm diameter per mL, no more than 5 particles ≥25 μm diameter per mL, and no more than 2 particles ≥50 μm diameter per mL, during shelf life, measured by microscopic inspection.

Item XXVIII is a liquid formulation of Ranibizumab, Aflibercept, or Bevacizumab in a pre-filled pharmaceutical package according to any one of the preceding items I-VII or XII-XXVII, in which the VEGF-antagonist is Ranibizumab and the liquid formulation of Ranibizumab meets the particle count requirements of USP789 or Ph. Eur. 5.7.1 or both at the time of filling the pre-filled pharmaceutical package, alternatively after three months of storage of the pre-filled pharmaceutical package at 5° C., alternatively after three months of storage of the pre-filled pharmaceutical package at 25° C. and 60% relative humidity, alternatively after three months of storage of the pre-filled pharmaceutical package at 40° C. and 75% relative humidity.

Item XXIX is a liquid formulation of Ranibizumab, Aflibercept, or Bevacizumab in a pre-filled pharmaceutical package according to any one of the preceding items, which is free of silicone oil on all product contacting surfaces of the pre-filled pharmaceutical package.

Item XXX is a liquid formulation of Ranibizumab, Aflibercept, or Bevacizumab in a pre-filled pharmaceutical package according to any one of the preceding items, which is free of baked-on silicone.

Item XXXI is a liquid formulation of Ranibizumab, Aflibercept, or Bevacizumab in a pre-filled pharmaceutical package according to any one of the preceding items, in which the wall comprises a staked needle or a luer connector.

Item XXXII is a liquid formulation of Ranibizumab, Aflibercept, or Bevacizumab in a pre-filled pharmaceutical package of any preceding item for use in administering a liquid formulation of Ranibizumab, Aflibercept, or Bevacizumab to a patient having an ocular disease, wherein the ocular disease optionally is selected from the group consisting of age-related macular degeneration (AMD), visual impairment due to diabetic macular edema (DME), visual impairment due to macular edema secondary to retinal vein occlusion (branch RVO or central RVO), or visual impairment due to choroidal neovascularization (CNV) secondary to pathologic myopia.

Item XXXIII is a liquid formulation of Ranibizumab, Aflibercept, or Bevacizumab in a pre-filled pharmaceutical package for the use according to item XXX, wherein a volume of 30 to 100 μl of the liquid formulation is administered to the patient.

Item XXXIV is a liquid formulation of Ranibizumab, Aflibercept, or Bevacizumab in a pre-filled pharmaceutical package according to any one of the preceding items, which is suitable for terminal sterilization by sterilizing gas, optionally ethylene oxide EO gas, optionally at a pressure of 16.6 in. (42.2 cm.) Hg for 10 hours at 120° F. (49° C.), or suitable for terminal sterilization by vaporized hydrogen peroxide (VHP), and in which the lumen is free or essentially free of sterilizing gas following the terminal sterilization.

Item XXXV is a liquid formulation of Ranibizumab, Aflibercept, or Bevacizumab in a pre-filled pharmaceutical package according to any one of the preceding items, which is terminally sterilized.

Item XXXVI is a liquid formulation of a VEGF-antagonist in a pre-filled pharmaceutical package comprising:
  a wall comprising a thermoplastic material; optionally a polyolefin, for example a cyclic olefin polymer, a cyclic olefin copolymer, or polypropylene; a polyester, for example polyethylene terephthalate; a polycarbonate; or any combination or copolymer of any two or more of these, preferably a cyclic olefin polymer (COP), having an interior surface enclosing at least a portion of a lumen;
  a tie coating or layer on the wall interior surface comprising $SiO_xC_yH_z$, in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS);
  a barrier coating or layer of $SiO_x$, in which x is from about 1.5 to about 2.9 as measured by XPS, the barrier coating or layer positioned between the tie coating or layer and the lumen;
  a pH protective coating or layer of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS, positioned between the barrier coating or layer and the lumen;
  a liquid formulation of a VEGF-antagonist, optionally Ranibizumab, Aflibercept, or Bevacizumab, in the lumen; and
  a closure closing the lumen.

Item XXXVII is a liquid formulation of a VEGF-antagonist in a pre-filled pharmaceutical package according to item XXXVI, further comprising a lubricity coating or layer positioned between the pH protective coating or layer and the lumen.

Item XXXVIII is a liquid formulation of a VEGF-antagonist in a pre-filled pharmaceutical package according to any one of the preceding items XXXVI to XXXVII, wherein the lubricity coating or layer has the atomic proportions $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS.

Item XXXIX is a liquid formulation of a VEGF-antagonist in a pre-filled pharmaceutical package according to any one of the preceding items XXXVI to XXXVIII, wherein the lubricity coating or layer is prepared by PECVD from an organosilicon precursor.

Item XL is a liquid formulation of a VEGF-antagonist in a pre-filled pharmaceutical package according to item XXXIX, wherein the lubricity coating or layer is prepared by PECVD from octamethylcyclotetrasiloxane (OMCTS) as the organosilicon precursor.

Item XLI is a liquid formulation of a VEGF-antagonist in a pre-filled pharmaceutical package according to any one of the preceding items XXXVI to XL, in which the front face of the closure closing the lumen is covered with a fluoropolymer coating or layer, wherein the front face is facing the liquid formulation.

Item XLII is a liquid formulation of a VEGF-antagonist in a pre-filled pharmaceutical package according to any one of the preceding items XXXVI to XLI, comprising a liquid formulation of Ranibizumab in the lumen.

Item XLIII is a liquid formulation of a VEGF-antagonist in a pre-filled pharmaceutical package according to item XLII, in which the liquid formulation of Ranibizumab in the lumen comprises Ranibizumab at a concentration of 6 or 10 mg/ml, optionally administered in a volume of 0.05 mL.

Item XLIV is a liquid formulation of a VEGF-antagonist in a pre-filled pharmaceutical package according to item XLII or XLIII, in which the liquid formulation of Ranibizumab in the lumen further comprises:
  a buffer in an amount effective to provide a pH of the liquid formulation in the range from about 5 to about 7;
  a non-ionic surfactant in the range of 0.005 to 0.02 mg/mL of complete formulation, and
  water for injection.

Item XLV is a liquid formulation of a VEGF-antagonist in a pre-filled pharmaceutical package according to item XLII, XLIII, or XLIV, in which the liquid formulation of Ranibizumab in the lumen comprises, per mL of formulation:
6 or 10 mg. Ranibizumab;
100 mg. α,α-trehalose dihydrate;
1.98 mg. L-histidine;
0.1 mg Polysorbate 20; and
water for injection qs to 1 mL.

Item XLVI is a liquid formulation of a VEGF-antagonist in a pre-filled pharmaceutical package according to item XLV, in which the liquid formulation of Ranibizumab has been adjusted to pH 5.5 with HCl.

Item XLVII is a liquid formulation of a VEGF-antagonist in a pre-filled pharmaceutical package according to any one of the preceding items XLII, XLIII, or XLIV, in which the liquid formulation of Ranibizumab in the lumen comprises, per mL of formulation:
6 or 10 mg. Ranibizumab;
100 mg. α,α-trehalose dihydrate;
0.32 mg. L-histidine
1.66 mg. L-histidine hydrochloride monohydrate;
0.1 mg Polysorbate 20; and
water for injection qs to 1 mL Item XLVIII is a liquid formulation of a VEGF-antagonist in a pre-filled pharmaceutical package according to any one of the preceding items XXXVI-XLI, comprising a liquid formulation of Aflibercept in the lumen.

Item XLIX is a liquid formulation of a VEGF-antagonist in a pre-filled pharmaceutical package according to item XLVIII, in which the liquid formulation of Aflibercept in the lumen comprises Aflibercept at a concentration of 40 mg/ml, optionally administered in a volume of 0.05 mL.

Item L is a liquid formulation of a VEGF-antagonist in a pre-filled pharmaceutical package according to any one of the preceding items XXXVI-XLI, comprising a liquid formulation of Bevacizumab in the lumen.

Item LI is a liquid formulation of a VEGF-antagonist in a pre-filled pharmaceutical package according to item L, in which the liquid formulation of Bevacizumab in the lumen comprises Bevacizumab at a concentration of 25 mg/ml, optionally administered in a volume of 0.05 mL.

Item LII is a liquid formulation of a VEGF-antagonist in a pre-filled pharmaceutical package according to any one of the preceding items XXXVI to LI, in which the liquid formulation is contained in a pre-filled pharmaceutical package having a nominal maximum fill volume of 0.5 or 1 mL.

Item LIII is a liquid formulation of a VEGF-antagonist in a pre-filled pharmaceutical package according to any one of the preceding items XXXVI to LII, in which the package is a vial or a cartridge.

Item LIV is a liquid formulation of a VEGF-antagonist in a pre-filled pharmaceutical package according to any one of the preceding items XXXVI to LIII, in which the package is a syringe and the stopper is a plunger slidable along the wall to deliver contents.

Item LV is a liquid formulation of a VEGF-antagonist in a pre-filled pharmaceutical package according to item LIV, in which the plunger comprises a side surface slidable along the wall.

Item LVI is a liquid formulation of a VEGF-antagonist in a pre-filled pharmaceutical package according to item LV, in which at least a portion of the side surface comprises a fluoropolymer lubricity coating or layer abutting the wall.

Item LVII is a liquid formulation of a VEGF-antagonist in a pre-filled pharmaceutical package according to any one of the preceding items LIV-LVI, having a breakout force less than or equal to 15N, optionally less than or equal to 10N, for initiating travel of the stopper in the lumen.

Item LVIII is a liquid formulation of a VEGF-antagonist in a pre-filled pharmaceutical package according to any one of the preceding items LIV-LVI, having a plunger sliding force less than or equal to 15N, optionally less than or equal to 10N for advancing the stopper in the lumen.

Item LIX is a liquid formulation of a VEGF-antagonist in a pre-filled pharmaceutical package according to any one of the preceding items XXXVI to LVIII, in which the liquid formulation of a VEGF-antagonist, optionally Ranibizumab, Aflibercept, or Bevacizumab, in the lumen forms an equal or smaller area % of basic decomposition species, after storage of the pharmaceutical package at 5° C. for three months, than a glass pharmaceutical package of the same volumetric capacity, internally coated with baked-on silicone.

Item LX is a liquid formulation of a VEGF-antagonist in a pre-filled pharmaceutical package according to any one of the preceding items XXXVI-XLVII or LII-LVIII, in which the VEGF-antagonist is Ranibizumab, and the liquid formulation of Ranibizumab in the lumen forms an equal or smaller area % of acidic decomposition species, after storage of the pharmaceutical package at 5° C. for three months, than a glass pharmaceutical package of the same volumetric capacity, internally coated with baked-on silicone.

Item LXI is a liquid formulation of a VEGF-antagonist in a pre-filled pharmaceutical package according to any one of the preceding items XXXVI-XLVII or LII-LVIII, in which the VEGF-antagonist is Ranibizumab, and the liquid formulation of Ranibizumab in the lumen forms an equal or smaller area % of basic decomposition species, after storage of the pharmaceutical package at 25° C. and 60% relative humidity for three months, than a glass pharmaceutical package of the same volumetric capacity, internally coated with baked-on silicone.

Item LXII is a liquid formulation of a VEGF-antagonist in a pre-filled pharmaceutical package according to any one of the preceding items XXXVI-XLVII or LII-LVIII, in which the VEGF-antagonist is Ranibizumab and the liquid formulation of Ranibizumab in the lumen forms an equal or smaller area % of acidic decomposition species, after storage of the pharmaceutical package at 25° C. and 60% relative humidity for three months, than a glass pharmaceutical package of the same volumetric capacity, internally coated with baked-on silicone.

Item LXIII is a liquid formulation of a VEGF-antagonist in a pre-filled pharmaceutical package according to any one of the preceding items XXXVI-XLVII or LII-LVIII, in which the VEGF-antagonist is Ranibizumab and the liquid formulation of Ranibizumab in the lumen forms an equal or smaller area % of basic decomposition species, after storage of the pharmaceutical package at 40° C. and 75% relative humidity for three months, than a glass pharmaceutical package of the same volumetric capacity, internally coated with baked-on silicone.

Item LXIV is a liquid formulation of a VEGF-antagonist in a pre-filled pharmaceutical package according to any one of the preceding items XXXVI-XLVII or LII-LVIII, in which the VEGF-antagonist is Ranibizumab and the liquid formulation of Ranibizumab in the lumen forms an equal or smaller area % of acidic decomposition species, after storage of the pharmaceutical package at 40° C. and 75% relative humidity for three months, than a glass pharmaceutical package of the same volumetric capacity, internally coated with baked-on silicone.

Item LXV is a liquid formulation of a VEGF-antagonist in a pre-filled pharmaceutical package according to any one of the preceding items XXXVI-XLVII or LII-LXIV, in which the VEGF-antagonist is Ranibizumab and the liquid formulation of Ranibizumab in the lumen forms an equal or smaller area % of aggregates, after storage of the pharmaceutical package at 25° C. and 60% relative humidity for three months, than a glass pharmaceutical package of the same volumetric capacity, internally coated with baked-on silicone.

Item LXVI is a liquid formulation of a VEGF-antagonist in a pre-filled pharmaceutical package preceding items XXXVI-XLVII or LII-LXIV, in which the VEGF-antagonist is Ranibizumab and the liquid formulation of Ranibizumab in the lumen forms an equal or smaller area % of aggregates, after storage of the pharmaceutical package at 40° C. and 75% relative humidity for three months, than a glass pharmaceutical package of the same volumetric capacity, internally coated with baked-on silicone.

Item LXVII is a liquid formulation of a VEGF-antagonist in a pre-filled pharmaceutical package according to any one of the preceding items XXXVI-XLVII or LII-LXVI, in which the VEGF-antagonist is Ranibizumab and the liquid formulation of Ranibizumab contains no more than 50 particles ≥10 μm diameter per mL, no more than 5 particles ≥25 μm diameter per mL, and no more than 2 particles ≥50 μm diameter per mL, during shelf life, measured by microscopic inspection.

Item LXVIII is a liquid formulation of a VEGF-antagonist in a pre-filled pharmaceutical package according to any one of the preceding items XXXVI-XLVII or LII-LXVII, in which the VEGF-antagonist is Ranibizumab and the liquid formulation of Ranibizumab meets the particle count requirements of USP789 or Ph. Eur. 5.7.1 or both at the time of filling the pre-filled pharmaceutical package, alternatively after three months of storage of the pre-filled pharmaceutical package at 5° C., alternatively after three months of storage of the pre-filled pharmaceutical package at 25° C. and 60% relative humidity, alternatively after three months of storage of the pre-filled pharmaceutical package at 40° C. and 75% relative humidity.

Item LXIX is a liquid formulation of a VEGF-antagonist in a pre-filled pharmaceutical package according to any one of the preceding items XXXVI to LXVIII, which is free of silicone oil on all product contacting surfaces of the pre-filled pharmaceutical package.

Item LXX is a liquid formulation of a VEGF-antagonist in a pre-filled pharmaceutical package according to any one of the preceding items XXXVI to LXIX, which is free of baked-on silicone.

Item LXXI is a liquid formulation of a VEGF-antagonist in a pre-filled pharmaceutical package according to any one of the preceding items XXXVI to LXX, in which the wall comprises a staked needle or a luer connector.

Item LXXII is a liquid formulation of a VEGF-antagonist in a pre-filled pharmaceutical package of any one of the preceding items XXXVI to LXXI for use in administering a liquid formulation of a VEGF-antagonist, optionally Ranibizumab, Aflibercept, or Bevacizumab, to a patient having an ocular disease, wherein the ocular disease optionally is selected from the group consisting of age-related macular degeneration (AMD), visual impairment due to diabetic macular edema (DME), visual impairment due to macular edema secondary to retinal vein occlusion (branch RVO or central RVO), or visual impairment due to choroidal neovascularization (CNV) secondary to pathologic myopia.

Item LXXIII is a liquid formulation of a VEGF-antagonist in a pre-filled pharmaceutical package for the use according to any one of the preceding items XXXVI to LXXII, wherein a volume of 30 to 100 μl of the liquid formulation is administered to the patient.

Item LXXIV is a liquid formulation of a VEGF-antagonist in a pre-filled pharmaceutical package according to any one of the preceding items XXXVI to LXXIII, which is suitable for terminal sterilization by sterilizing gas, optionally ethylene oxide EO gas, optionally at a pressure of 16.6 in. (42.2 cm.) Hg for 10 hours at 120° F. (49° C.), or suitable for terminal sterilization by vaporized hydrogen peroxide (VHP), and in which the lumen is free or essentially free of sterilizing gas following the terminal sterilization.

Item LXXV is a liquid formulation of a VEGF-antagonist in a pre-filled pharmaceutical package according to any one of the preceding items XXXVI to LXXIV, which is terminally sterilized.

Item LXXVI is a pre-filled pharmaceutical package according to any one of claims 33, 35, 37-45, in which the plunger breakout force is determined using the ISO 7886-1:1993 test.

Item LXXVII is a liquid formulation of a VEGF-antagonist in a pre-filled pharmaceutical package according to any one of the preceding items XVII, XIX-XXXV of this specification, in which the plunger breakout force is determined using the ISO 7886-1:1993 test.

Item LXXVIII is a pre-filled pharmaceutical package according to any one of claims 34, 35, 37-45, in which the plunger sliding force is determined using the ISO 7886-1: 1993 test.

Item LXXIX is a liquid formulation of a VEGF-antagonist in a pre-filled pharmaceutical package according to any one of the preceding items XVIII-XXXV of this specification, in which the plunger sliding force is determined using the ISO 7886-1:1993 test.

Item LXXX is a pre-filled pharmaceutical package according to any one of claims 33, 35, 37-45, in which the plunger breakout force is determined using the Protocol for Lubricity Testing defined in this specification.

Item LXXXI is a liquid formulation of a VEGF-antagonist in a pre-filled pharmaceutical package according to any one of the preceding items XVII, XIX-XXXV of this specification, in which the plunger breakout force is determined using the Protocol for Lubricity Testing defined in this specification.

Item LXXXII is a pre-filled pharmaceutical package according to any one of claims 34, 35, 37-45, in which the plunger sliding force is determined using the Protocol for Lubricity Testing defined in this specification.

Item LXXXIII is a liquid formulation of a VEGF-antagonist in a pre-filled pharmaceutical package according to any one of the preceding items XVIII-XXXV of this specification, in which the plunger sliding force is determined using the Protocol for Lubricity Testing defined in this specification.

Many additional and alternative aspects and embodiments of the invention are also contemplated, and are described in the specification and claims that follow.

Figure 1:
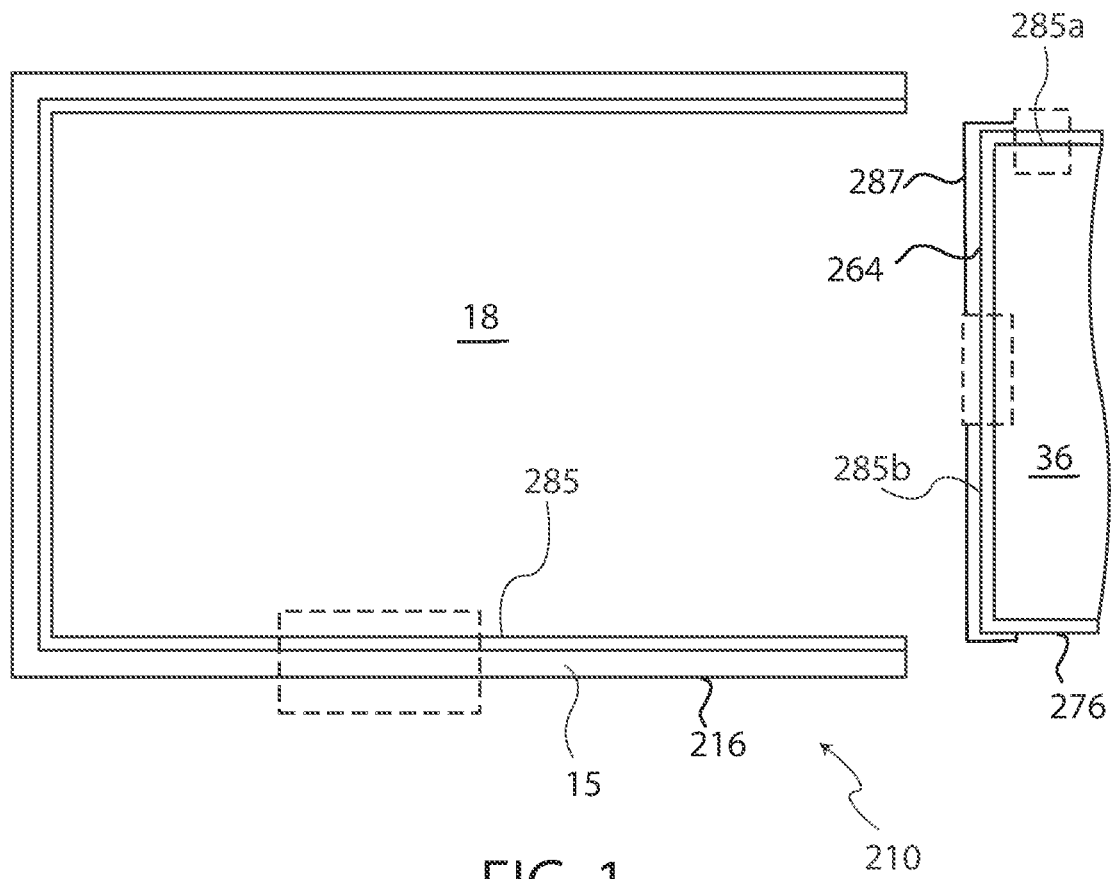
FIG. 1 is a schematic sectional view of a pharmaceutical package, with the closure removed to show detail.

The following reference characters are used in the drawing figures:

| | |
|---|---|
| 12 | Capped assembly or workpiece |
| 14 | Vessel |
| 15 | Wall |
| 16 | Interior surface (of 15) |
| 18 | Lumen |
| 20 | Dispensing portion (for example needle) |
| 22 | Front end (of 14) |
| 24 | Distal opening |
| 26 | Dispensing portion lumen |
| 28 | Shield |
| 30 | Barrier coating or layer |
| 32 | Back end (of 14) |
| 34 | pH protective coating or layer |
| 35 | Front face (of 36) |
| 36 | Stopper (of 210) |
| 38 | Plunger rod |
| 40 | Formulation |
| 42 | Rib |
| 48 | Catch |
| 50 | Vessel support |
| 60 | Coating station |
| 61 | Quadrupole magnet |
| 62 | Quadrupole magnet |
| 63 | Quadrupole magnet |
| 64 | Quadrupole magnet |
| 79 | Polar axis of magnet |
| 80 | Axis |
| 81 | Recess between magnets or within coil |
| 82 | Opening |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (inner electrode) |
| 110 | Gas delivery port (of 108) |
| 114 | Housing (of 50) |
| 116 | Collar |
| 118 | Exterior surface (of 80) |
| 144 | PECVD gas source |
| 152 | Pressure gauge |
| 160 | Outer electrode |
| 162 | Power supply |
| 164 | Sidewall (of 160) |
| 166 | Sidewall (of 160) |
| 168 | Closed end (of 160) |
| 210 | pharmaceutical package |
| 216 | Outer surface |
| 220 | Interior surface (of 30) |
| 222 | Outer surface (of 30) |
| 224 | Interior surface (of 34) |
| 285a | Vessel coating set |
| 285b | Vessel coating set |
| 226 | Outer surface (of 34) |
| 264 | Inner or interior surface (of 36) |
| 276 | Side surface |
| 278 | Inner or interior surface (of 280) |
| 287 | Lubricity coating or layer |
| 404 | Exhaust |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Precursor gas |
| 590 | Organosilicon feed line (capillary) |
| 592 | Organosilicon shut-off valve |
| 594 | Oxidizing gas |
| 596 | Oxygen feed line |
| 598 | Mass flow controller |
| 600 | Oxygen shut-off valve |
| 602 | Diluent gas reservoir |
| 604 | Feed line |
| 606 | Shut-off valve |
| 614 | Headspace |
| 616 | Pressure source |
| 618 | Pressure line |
| 620 | Capillary connection |
| 838 | Tie coating or layer |

In the context of the present invention, the following definitions and abbreviations are used:

A "pre-filled syringe" is a conventional syringe or cartridge which is supplied by the manufacturer in a filled state, i.e. a measured dose of the drug to be administered is already present in the syringe when it is purchased and ready for administration. In particular, the pharmaceutical composition containing the drug does not have to be drawn from a vial containing the composition by using an empty syringe. The term pre-filled syringe within the meaning of the present invention does not refer to syringes the content of which has been drawn from a vial in a repackaging process. A "pre-filled pharmaceutical package" includes a pre-filled syringe or cartridge, but is more broadly defined to also include a vial or other type of storage vessel containing one or multiple doses of a drug which is supplied by the manufacturer in a filled state, even if the drug must be transferred to a syringe or other intermediate device for administration.

The term "at least" in the context of the present invention means "equal or more" than the number following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, for example, coatings or layers, refer to the minimum number of items, such as coatings or layers, that are present, but do not necessarily represent the order or total number of coatings or layers require additional coatings or layers beyond the stated number. For example, a "first" coating or layer in the context of this specification can be either the only coating or layer or any one of plural coatings or layers, without limitation. In other words, recitation of a "first" coating or layer allows but does not require an embodiment that also has a second or further coating or layer.

For purposes of the present invention, an "organosilicon precursor" is a compound having at least one of the linkages:

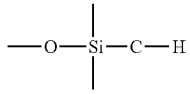

which is a tetravalent silicon atom connected to an oxygen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be a pharmaceutical package or other vessel. Some examples of a pharmaceutical package include, but are not limited to, a vial, a cartridge, or a syringe.

In the empirical composition $Si_wO_xC_yH_z$ or the equivalent composition $SiO_xC_yH_z$ or $SiO_xC_y$, the values of w, x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

Also, although $SiO_xC_yH_z$ is described as equivalent to $SiO_xC_y$, it is not necessary to show the presence of hydrogen in any proportion to show the presence of $SiO_xC_y$. Unless otherwise indicated here, the value of w is normalized to 1, and the subscript w is then conventionally omitted. The coating or layer may thus in one aspect have the formula $Si_wO_xC_yH_z$, for example where w is 1, x is from about 0.5 to about 2.4, y is from about 0.6 to about 3, and z is from about 2 to about 9. The same coating or layer, with the same determination of w, x, and y, may thus in another aspect have the formula $SiO_xC_y$, for example where x is from about 0.5 to about 2.4, y is from about 0.6 to about 3, and w and z are omitted.

The atomic ratios of silicon, oxygen, and carbon can be determined by XPS. The atomic ratio of H atoms cannot be measured by XPS, which does not detect hydrogen. Optionally, the proportion of H atoms can be determined separately, for example by Rutherford backscattering (RBS) or hydrogen forward scattering (HFS), preferably the former.

The term "syringe" is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

A coating or layer or treatment is defined as "hydrophobic" if it lowers the wetting tension of a surface, compared to the corresponding uncoated or untreated surface. Hydrophobicity is thus a function of both the untreated substrate and the treatment.

A "lubricity layer" according to the present invention is a coating which has a lower frictional resistance than the uncoated surface. In other words, it reduces the frictional resistance of the coated surface in comparison to a reference surface that is uncoated. The present lubricity layers are primarily defined by their lower frictional resistance than the uncoated surface and the process conditions providing lower frictional resistance than the uncoated surface.

"Frictional resistance" can be static frictional resistance and/or kinetic frictional resistance.

One of the optional embodiments of the present invention is a syringe part, e.g. a syringe barrel or plunger, coated with a lubricity layer. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity characteristics of a lubricity layer or coating in the context of the present invention whenever the coating is applied to any syringe or syringe part, for example to the inner wall of a syringe barrel. The breakout force is of particular relevance for evaluation of the coating effect on a prefilled syringe, i.e. a syringe which is filled after coating and can be stored for some time, e.g. several months or even years, before the plunger is moved again (has to be "broken out").

The "plunger sliding force" (synonym to "glide force," "maintenance force," $F_m$, also used in this description) in the context of the present invention is the force required to maintain movement of a plunger in a syringe barrel, e.g. during aspiration or dispense. It can advantageously be determined using the ISO 7886-1:1993 test known in the art. A synonym for "plunger sliding force" often used in the art is "plunger force" or "pushing force".

The "plunger breakout force" (synonym to "breakout force", "break loose force", "initiation force", $F_i$, also used in this description) in the context of the present invention is the initial force required to move the plunger in a syringe, for example in a prefilled syringe.

Both "plunger sliding force" and "plunger breakout force" and methods for their measurement are described in more detail in this description. These two forces can be expressed in N, lbs. or kg and all three units are used herein. These units correlate as follows: 1N=0.102 kg=0.2248 lbs. (pounds).

Sliding force and breakout force are sometimes used herein to describe the forces required to advance a stopper or other closure into a vessel, such as a medical sample tube or a vial, to seat the closure in a vessel to close the vessel. Its use is analogous to use in the context of a syringe and its plunger, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger, closure, or other removable part is permitted to slide in a syringe barrel or other vessel.

The term "closure" as used in this specification and claims refers to any part or sub-assembly of a pharmaceutical package or vessel closing the lumen, or that can be used to close the vessel lumen, and can be removed, moved, broken, deformed, pierced, or otherwise manipulated to open the package or vessel, dispense its contents, or provide access to its contents. The closure can be a separable part, such as a crimp, septum, stopper, plunger, plunger tip, cap, piston, seal, or needle shield; or an integral or joined part, such as the wall portion of an ampoule or film packet broken or parted to release contents or a web blocking the nozzle of a tube before it is pierced to release the contents through the nozzle, or a valve that is closed and can be opened. The term "closure" equally applies to a plunger tip, a plunger piston, a plunger piston and plunger tip assembly; to any of these further assembled with a plunger rod; or to any of these without a plunger rod present.

In the context of a prefilled syringe the closure is typically a stopper which is often also referred to as a plunger stopper or simply plunger. Thus, in the context of a prefilled syringe the terms "stopper", "plunger stopper" and "plunger" are used interchangably herein. The plunger stopper can be moved within the syringe barrel by a plunger rod, wherein the plunger stopper and the plunger rod may be mechanically connected. In case of a non-retractable stopper, the plunger rod is not mechanically connected to the plunger stopper. Thus, a non-retractable stopper can be pushed into the syringe barrel by pushing the plunger rod into the syringe barrel towards the outlet but it cannot be retracted by pulling the plunger rod towards the rear of the syringe barrel.

The word "comprising" does not exclude other elements or steps.

DETAILED DESCRIPTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

VEGF-Antagonist Ocular Drugs for Intravitreal Injection

An "intraocular neovascular disease" is a disease characterized by ocular neovascularisation. Examples of intraocular neovascular diseases include, for example, proliferative retinopathies, choroidal neovascularisation (CNV), age-related macular degeneration (AMD), diabetic and other ischemia-related retinopathies, diabetic macular oedema, pathological myopia, von Hippel-Lindau disease, histoplasmosis of the eye, Central Retinal Vein Occlusion (CRVO), Branch Retinal Vein Occlusion (BRVO), corneal neovascularisation, and retinal neovascularisation. The term "age-related macular degeneration" refers to a medical condition which usually affects older adults and results in a loss of vision in the centre of the visual field (the macula) because of damage to the retina. Some or all of these conditions can be treated by intravitreal injection of a VEGF-antagonist.

The term "VEGF-antagonist" refers to a molecule which specifically interacts with VEGF and inhibits one or more of its biological activities, for example its mitogenic, angiogenic and/or vascular permeability activity. It is intended to include both anti-VEGF antibodies and antigen-binding fragments thereof and non-antibody VEGF-antagonists.

Non-antibody VEGF-antagonists include Aflibercept, Pegaptanib, and antibody mimetics. Aflibercept which is presently marketed under the name Eylea® is a recombinant human soluble VEGF receptor fusion protein in which portions of human VEGF receptors 1 and 2 extracellular domains are fused to the Fc portion of human IgG1 (Holash et al. (2002) Proc. Natl. Acad. Sci. USA 99(17): 11393-11398; WO 00/75319 A1). Pegaptanib which is presently marketed under the name Macugen® is a pegylated anti-vascular endothelial growth factor (VEGF) aptamer (Bell et al. (1999) In Vitro Cell Dev Biol Anim. 35(9): 533-42). Antibody mimetics which are VEGF-antagonists include binding proteins comprising an ankyrin repeat domain that binds VEGF and inhibits its binding to the receptor, such as DARPin® MP0112 (see also WO 2010/060748 and WO 2011/135067).

The term "anti-VEGF antibody" refers to an antibody or antibody fragment such as a Fab or an scFV fragment that specifically binds to VEGF and inhibits one or more of its biological activities, for example its mitogenic, angiogenic and/or vascular permeability activity. Anti-VEGF antibodies act, for example, by interfering with the binding of VEGF to a cellular receptor, by interfering with vascular endothelial cell activation after VEGF binding to a cellular receptor, or by killing cells activated by VEGF. Anti-VEGF antibodies include, for example, antibodies A4.6.1, Bevacizumab, Ranibizumab, G6, B20, 2C3, and others as described in, for example, WO 98/45331, US 2003/0190317, U.S. Pat. Nos. 6,582,959, 6,703,020, WO 98/45332, WO 96/30046, WO 94/10202, WO 2005/044853, EP 0 666 868 B1, WO 2009/155724 and Popkov et al. (2004) J. Immunol. Meth. 288: 149-64. Preferably, the anti-VEGF antibody or antigen-binding fragment thereof present in the pharmaceutical composition of the present invention is Ranibizumab or Bevacizumab. Most preferably, it is Ranibizumab or an antigen-binding fragment thereof.

"Ranibizumab" is a humanised monoclonal Fab fragment directed against VEGF-A having the light and heavy chain variable domain sequences of Y0317 as described in SEQ ID Nos. 115 and 116 of WO 98/45331 and Chen et al. (1999) J. Mol. Biol. 293: 865-81. The CAS number of Ranibizumab is 347396-82-1. Ranibizumab inhibits endothelial cell proliferation and neovascularisation and has been approved for the treatment of neovascular (wet) age-related macular degeneration (AMD), the treatment of visual impairment due to diabetic macular oedema (DME), the treatment of visual impairment due to macular oedema secondary to retinal vein occlusion (branch RVO or central RVO), or treatment of visual impairment due to choroidal neovascularisation (CNV) secondary to pathologic myopia. Ranibizumab is related to Bevacizumab and derived from the same parent mouse antibody as Bevacizumab but it is much smaller than the parent molecule and has been affinity matured to provide stronger binding to VEGF-A. Ranibizumab is produced recombinantly in *Escherichia coli*, for example as described in WO 98/45331 A2. The present commercial Ranibizumab formulation contains α, α-trehalose dihydrate, histidine hydrochloride monohydrate, histidine, polysorbate 20 and water for injection and is supplied in a concentration of 10 mg/ml. In particular, it contains 6 or 10 mg. Ranibizumab, 100 mg. α,α-trehalose dihydrate; 0.32 mg. L-histidine, 1.66 mg. L-histidine hydrochloride monohydrate, 0.1 mg Polysorbate 20 and water for injection qs to 1 mL. The pH of the present commercial Ranibizumab formulation may be adjusted to pH 5.5.

"Bevacizumab" is a full-length, humanized murine monoclonal antibody that recognizes all isoforms of VEGF and which is the parent antibody of Ranibizumab. The CAS number of Bevacizumab is 216974-75-3. Bevacizumab inhibits angiogenesis and is presently approved for the treatment of different cancer types. However, it is also used off-label in ophthalmological diseases such as age-related macular degeneration. The present commercial Bevacizumab formulation contains α, α-trehalose dihydrate, sodium phosphate, polysorbate 20 and water for injection and is supplied as a concentrate with a concentration of 25 mg/ml. In particular, it contains 25 mg/ml Bevacizumab, 240 mg α,α-trehalose dihydrate, 23.2 mg sodium phosphate (monobasic, monohydrate), 4.8 mg sodium phosphate (dibasic, anhydrous), 1.6 mg polysorbate 20, and water for Injection, USP.

The antibody concentration within the pre-filled syringes of the present invention is typically 1-100 mg/ml, preferably 2-75 mg/ml, more preferably 3-50 mg/ml, even more preferably 5 to 30 mg/ml and most preferably 6 or 10 mg/ml. If Ranibizumab is contained within the pre-filled syringe of the present invention the Ranibizumab concentration is 10 mg/ml.

Aflibercept, marketed under the name Eylea, is a recombinant fusion protein consisting of the VEGF binding portion from the extracellular domains of human VEGF receptors 1 and 2 that are fused to the Fc portion of the human IgG1 immunoglobulin. It is approved for the treatment of wet macular degeneration. The CAS number of Aflibercept is 862111-32-8. It has received a marketing authorization for the treatment of wet age-related macular degeneration, visual impairment due to diabetic macular oedema (DME) and diabetic retinopathy in patients with diabetic macular edema. The present commercial Aflibercept formulation contains sodium phosphate, sodium chloride, polysorbate 20, sucrose and water for injection and is supplied in a concentration of 40 mg/ml. In particular, it contains 40 mg/ml Aflibercept, 10 mM sodium phosphate buffer, 40 mM NaCl, 0.03% polysorbate 20, 5% sucrose; and water for injection. An alternative Aflibercept formulation may contain a histidine buffer, sodium chloride, polysorbate 20, sucrose and water for injection and is supplied in a concentration of 40 mg/ml. In particular, it contains 40 mg/ml Aflibercept, 10 mM histidine buffer, 40 mM NaCl, 0.03% polysorbate 20, 5% sucrose; and water for injection. The pH of the commercial and the alternative Aflibercept formulation may be adjusted to 6.2.

Ranibizumab, marketed under the name Lucentis®, is a Fab fragment of a humanized murine monoclonal antibody directed against VEGF and has been approved for the treatment of ocular diseases such as age-related macular degeneration and diabetic macular oedema.

In addition, the off-label use of the full-length antibody Bevacizumab (Avastin®), which is also directed against VEGF for the treatment of ocular diseases, is common.

Ranibizumab and Bevacizumab appear to have similar efficacy profiles in the treatment of neovascular age-related macular degeneration, although rare adverse events seem to occur more often with Bevacizumab (Johnson and Sharma (2013) Curr. Opin. Ophthalmol.: 24(3):205-12).

The drug contained in the pre-filled syringe of the present invention, i.e. the VEGF-antagonist, preferably an anti-VEGF antibody or Aflibercept, is stable at a temperature of 2 to 8° C. for at least six months, preferably for at least 9 months, more preferably for at least one year, particularly preferably for at least 18 months and most preferably for about two years. The drug contained in the pre-filled syringe of the present invention, i.e. the VEGF-antagonist, preferably an anti-VEGF antibody or Aflibercept and more preferably Ranibizumab, is stable at room temperature, i.e. a temperature between 20° C. and 25° C., for at least three days or one week, preferably for at least two or three weeks, more preferably for about 4 weeks and most preferably for at least three months. The drug contained in the pre-filled syringe of the present invention, i.e. the VEGF-antagonist, preferably an anti-VEGF antibody or a VEGF receptor fusion protein and more preferably Ranibizumab or Aflibercept, is stable at a temperature of about 40° C., for at least four or six hours, preferably for at least 10 or 12 hours, more preferably for at least 18 or 24 hours and most preferably for one or two weeks.

The stability of the drug within the syringe can, for example, be determined by ion exchange chromatography, by which modifications of the drug such as oxidized and deamidated species can be detected or by size exclusion chromatography, by which aggregates of the drugs can be detected. A description of such an analysis is provided in the examples section.

The drug, i.e. the VEGF-antagonist, preferably the anti-VEGF antibody or Aflibercept, is considered stable, if the sum of all impurities comprising aggregates and chemically modified species is less than 2%, preferably less than 1.5%, more preferably less than 1.2% and most preferably less than 1% compared to the amount of non-modified, non-aggregated drug.

The components of a pre-filled syringe are known to a skilled person and basically comprise a syringe barrel and a plunger.

The syringe barrel contains a defined volume of the liquid composition which can be expelled from the barrel through an outlet positioned on one end of the barrel when the plunger is pushed into and moves along the barrel. The syringe barrel typically has a substantially cylindrical shape. The outlet may comprise a projection from the outlet end through which extends a channel having a smaller diameter than the rest of the syringe barrel. The outlet may be adapted, for example by a luer lock type connection, (if no staked needle is used) for connection with a needle or other accessory such as a sealing device which is able to seal the barrel and can be removed to allow a needle to be attached to the syringe. This sealing can be achieved by the use of known sealing devices such as the OVS™ system of Vetter Pharma International GmbH. Staked needles are also available, either molded-in needles that are permanently incorporated when injection molding the syringe barrel or glued needles that are secured in a molded delivery passage of the syringe barrel.

Optionally in a pre-filled syringe the syringe outlet is firmly connected with a staked needle and does not need to be assembled prior to use. In this case, the risk of injuries with the needle during assembly of the syringe before injection is reduced. The staked needle can be attached to the pre-filled plastic syringe of the present invention without using an adhesive, since it can be molded into the syringe. In contrast, an adhesive is required to attach the needle to a glass syringe and can lead to impurities or increased protein oxidation (presentation of Adler at the 2011 PDA Europe The Universe of Pre-Filled Syringes and Injection Devices, Basel, 7-11 Nov. 2011; presentation of Markovic at the PDA Single Use Systems Workshop, Bethesda, 22-23 Jun. 2011).

For intravitreal administration, the needle size is typically 29, 29 or 30 gauge, although 31-, 32-, 33- and 34-gauge needles may also be used. The pre-filled syringe may be equipped with a passive needle safety guard to further avoid the danger of needle sticks after injection.

The syringe barrel is preferably tungsten-free, i.e. it does not contain any traces of tungsten, since it is not necessary to use tungsten in the syringe manufacturing process. Hence, there is no risk of tungsten-induced protein aggregation.

In one embodiment the syringe barrel comprises a mark such as a line printed on the syringe barrel which line allows the person injecting the liquid composition to align a predetermined part of the stopper (such as the tip of the front surface) or plunger with the mark. Thereby, any excess liquid composition and potential air bubbles are removed from the syringe barrel, allowing the safe administration of an exact predetermined dosage to the patient.

The plunger is pushed inside the syringe barrel, allowing the syringe to expel the liquid formulation through the outlet.

In a prefilled syringe the stopper is in contact with the liquid formulation. The stopper is typically made of an elastomeric material such as natural or synthetic rubber, which engages an inner surface of the syringe barrel to create a seal that facilitates ejecting the liquid formulation from the syringe when pressure is applied to the plunger.

In a preferred embodiment the plunger stopper is a non-retractable stopper, i.e. a stopper which is not mechanically connected to plunger rod. The term "non-retractable stopper" is intended to mean that the stopper can only be moved in the direction of the syringe outlet, but not in the opposite direction, i.e. to the rear part of the syringe. Hence, any risk for the contamination of the liquid composition within the syringe is minimized. Typically, a non-retractable stopper can be pushed by the plunger rod in the direction of the syringe outlet to expel the liquid formulation, but stays in its position when the plunger rod is retracted towards the rear end of the syringe.

The syringe has a nominal maximum fill volume, i.e. a volume which can be maximally taken up by the syringe, of 0.3 ml to 1.5 ml, preferably of 0.5 ml to 1.0 ml, most preferably 0.5 ml or 1.0 ml. For an injection volume of about 0.05 ml, a syringe having a nominal fill volume of 0.5 ml is preferred.

The volume of the liquid composition filled into the syringe is about 0.05 ml to about 1 ml, preferably about 0.1 ml to about 0.5 ml, more preferably 0.14 ml to 0.3 ml and most preferably 0.15 ml to 0.2 ml.

The skilled person knows that the syringe is usually filled with a volume which is larger than the volume actually administered to the patient to take into account any dead space within the syringe and the needle and the loss due to the preparation of the syringe for injection. Hence, the volume which is actually administered to the patient is between 0.01 ml and 1 ml, preferably between 0.02 and 0.5 ml, more preferably between 0.025 and 0.5 ml and most preferably between 0.03 ml and 0.05 ml.

Ranibizumab is typically administered in a volume of 0.05 ml with a Ranibizumab concentration of 6 or 10 mg/ml or in a volume of 0.03 ml or 0.05 ml with a Ranibizumab concentration of 10 mg/ml, yielding a delivered amount of 0.3 or 0.5 mg. For Aflibercept the administered volume is typically 0.05 ml with an Aflibercept concentration of 40 mg/ml, yielding a delivered amount of 2 mg. As discussed above, Bevacizumab is used off-label for the treatment of ocular diseases. In this case, the administered volume of Bevacizumab is 0.05 ml with a Bevacizumab concentration of 25 mg/ml, yielding a delivered amount of 1.25 mg.

Hence, in one embodiment the syringe is filled with a volume of the liquid composition of 0.15 ml to 0.2 ml and 0.03 ml to 0.05 ml of the liquid composition are administered to the patient.

The drug contained in the pre-filled syringe of the present invention, i.e. the VEGF-antagonist, preferably an anti-VEGF antibody or Aflibercept and more preferably Ranibizumab, retains its biological activity when stored at a temperature of 2 to 8° C. for at least six months, preferably for at least 9 months, more preferably for at least one year, particularly preferably for at least 18 months and most preferably for about two years. The drug contained in the pre-filled syringe of the present invention, i.e. the VEGF-antagonist, preferably an anti-VEGF antibody or Aflibercept and more preferably Ranibizumab, retains its biological activity when stored at room temperature, i.e. a temperature between 20° C. and 25° C., for at least one hour, preferably for at least six hours, more preferably for at least twelve hours, and most preferably for about 24 hours.

The biological activity of the VEGF-antagonist, preferably an anti-VEGF antibody or Aflibercept and more preferably Ranibizumab, can be determined by incubating the antagonist which was stored under the conditions described above with human umbilical vein endothelial cells (HUVEC) and VEGF and measuring the VEGF-induced proliferation of the cells in the presence of the antagonist, i.e. by the CellTiter-Blue® Cell Viability Assay available from Promega, in comparison to cells not incubated with the antagonist. Since the VEGF-antagonist inhibits VEGF-induced signal transduction, the VEGF-induced proliferation will be reduced, if biologically active VEGF-antagonist is present in the sample.

The VEGF-antagonist, preferably the anti-VEGF antibody or Aflibercept and more preferably Ranibizumab retains its biological activity after storage in the pre-filled syringe, if the VEGF-induced proliferation is inhibited by at least 50%, preferably by at least 55% or 60%, more preferably by at least 65%, 70%, 75% or 80%, even more preferably by at least 85%, 87% or 90% and most preferably by at least 92%, 94%, 96%, 98% or 99%.

The pre-filled syringe may contain one or more pharmacologically active agents in addition to the VEGF antagonist. A pharmacologically active agent is able to exert a pharmacological effect when administered to a subject. Preferably, the additional pharmacologically active agent is a PDGF antagonist or an Ang2 antagonist. More preferably, the PDGF antagonist is an anti-PDGF antibody such as rinucumab or an aptamer such as E10030, marketed as Fovista®. Most preferably, the PDGF antagonist is E10030 which is described in Green et al. (1996) Biochemistry 35: 14413; U.S. Pat. Nos. 6,207,816; 5,731,144; 5,731,424; and 6,124,449. Also more preferably, the Ang2 antibody is an anti-Ang2 antibody and most preferably it is nesvacumab.

The liquid composition within the pre-filled syringe of the present invention has low particle content. In particular, it comprises less than 50 particles having a size of more than 10 μm after the syringe has been rotated at 40° C. for five minutes, two weeks or four weeks after three freeze-thaw cycles from +5° C. to −20° C. with 1° C. per minute, or after storage of the syringe at 5° C., 25° C. and 60% relative humidity or 40° C. and 75% relative humidity for three months. Alternatively or additionally, the liquid composition comprises less than 5 particles having a size of more than 25 μm after the syringe has been rotated at 40° C. for five minutes, two weeks or four weeks, or after three freeze-thaw cycles from +5° C. to −20° C. with 1° C. per minute, or after storage of the syringe at 5° C., 25° C./60% relative humidity or 40° C./75% relative humidity for three months. Hence, the pre-filled syringe meets the requirements of United States Pharmacopoeia <789> for ophthalmic solutions with respect to these particle sizes.

The pre-filled syringe of the present invention further has excellent gliding behaviour (breakout force and plunger sliding force). In particular, the breakout force, i.e. the force required to initiate the movement of the plunger, is less than 15N, 10N, or 9N, preferably less than 8N or 7N, more preferably less than 6N and most preferably less than 5N. The breakout force does not change significantly, i.e. by more than 10%, when the syringe is stored for an extended period such as eight weeks. In contrast, in a syringe containing silicone the breakout force increases upon storage by at least twofold.

Further, the plunger sliding force, i.e. the force required to sustain the movement of the plunger along the syringe barrel to expel the liquid composition, is less than 10N, preferably less than 9N, more preferably less than 8N and most preferably less than 7N. In a particularly preferred embodiment there is no significant difference between the breakout force and the plunger sliding force.

The present invention also provides a kit comprising one or more of the pre-filled syringes of the present invention. Preferably, the kit comprises a blister pack. A "blister pack" has a cavity or pocket which is usually made from thermoformed plastic and a backing of paperboard or a lidding seal of aluminum foil or plastic. The kit may further comprise a needle, if the pre-filled syringe does not comprise a staked-in needle. The kit may further comprise instructions for use. Preferably, the kit does not comprise an oxygen absorber which is typically used to reduce the level of oxygen within a package such as a blister pack. Oxygen absorbers usually contain a substance such as ferrous carbonate or ascorbate which substance reacts with any oxygen within a package with a high affinity, thereby reducing the oxygen content of the package.

Figure 2:
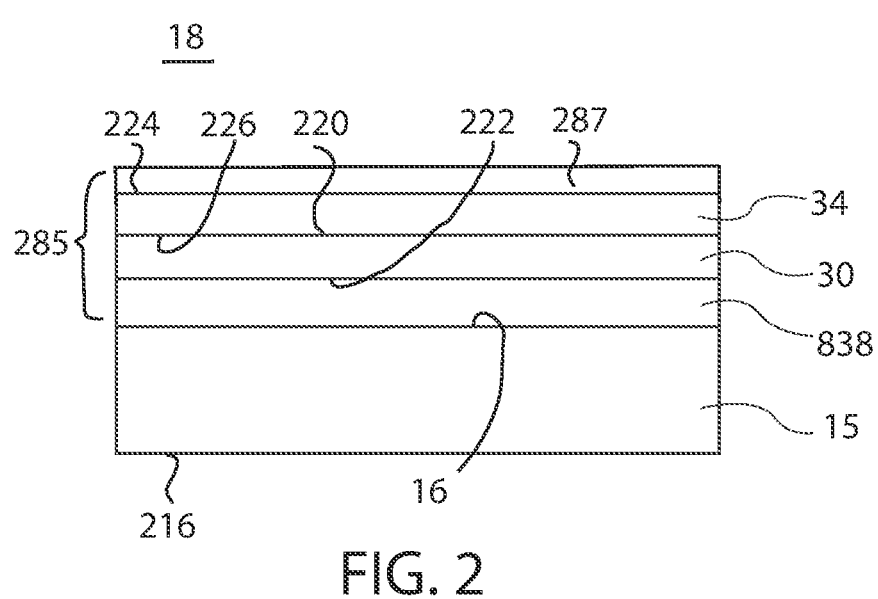
FIG. 2 is an enlarged detail view of the indicated portion of FIG. 1.
Figure 3:
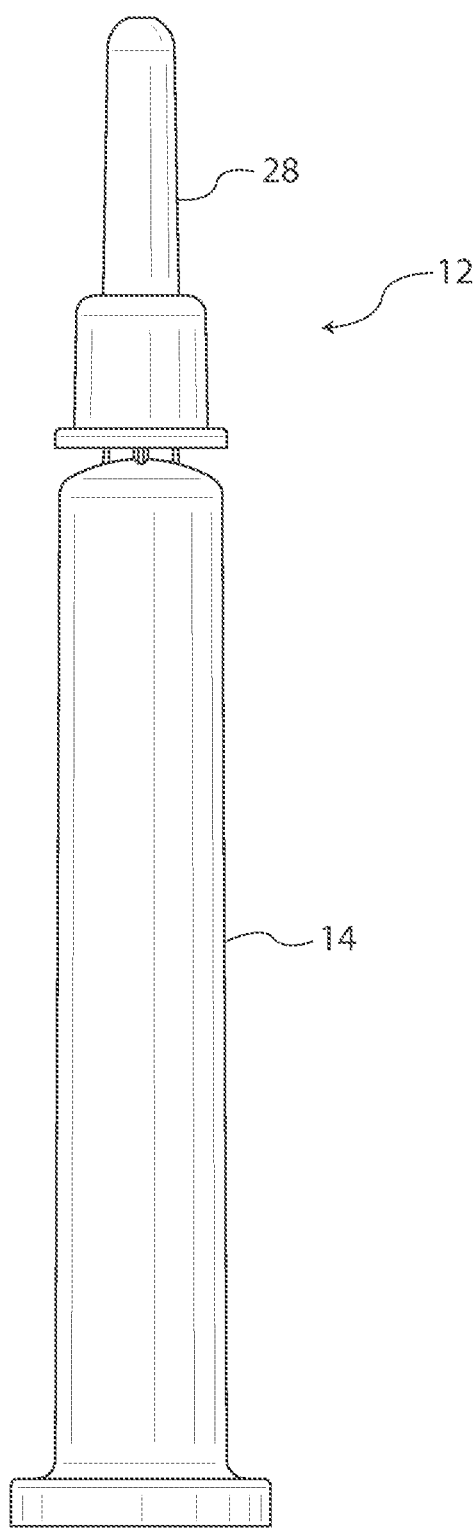
FIG. 3 is an elevation view of a capped assembly of a medical barrel, hypodermic needle, and cap, also known as a capped assembly, according to an embodiment of the disclosure.
Figure 4:
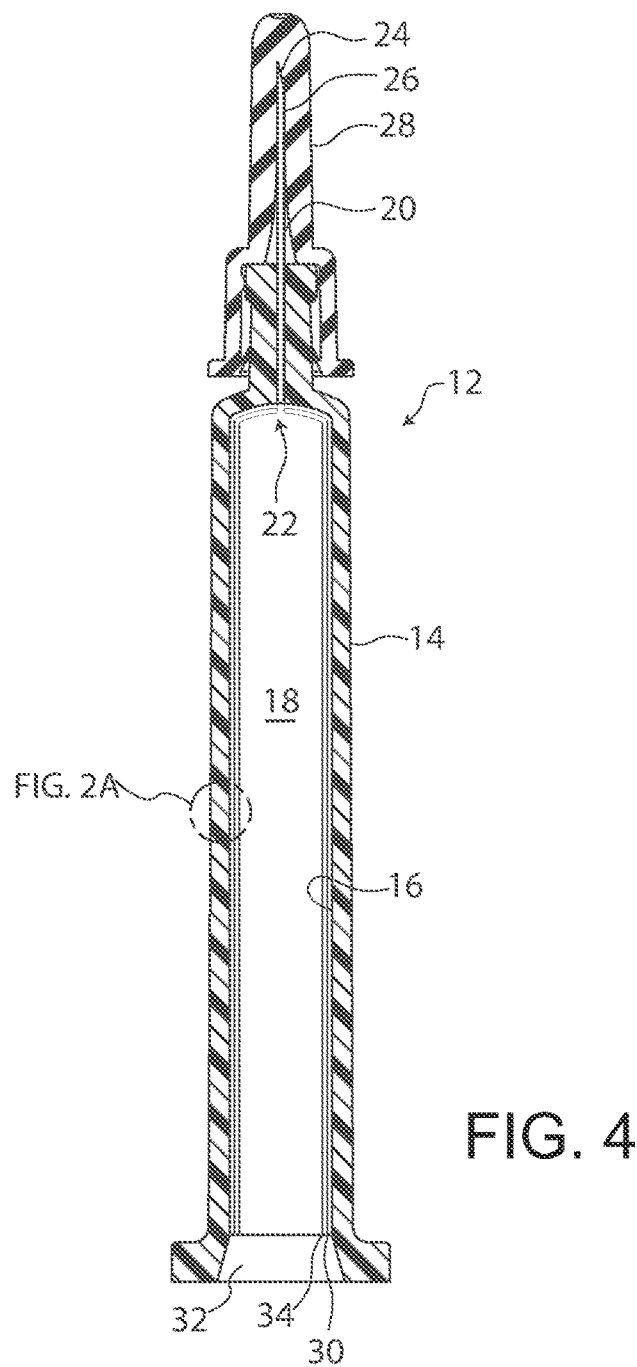
FIG. 4 is a longitudinal section of the capped assembly of FIG. 1, showing in an enlarged detail view, FIG. 4A, a trilayer PECVD set.
Figure 4A:
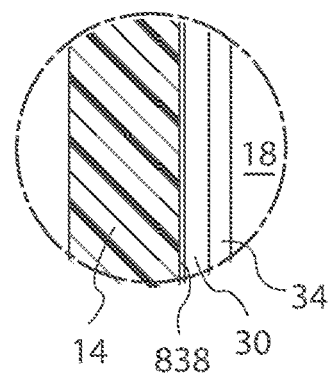
Figure 5:
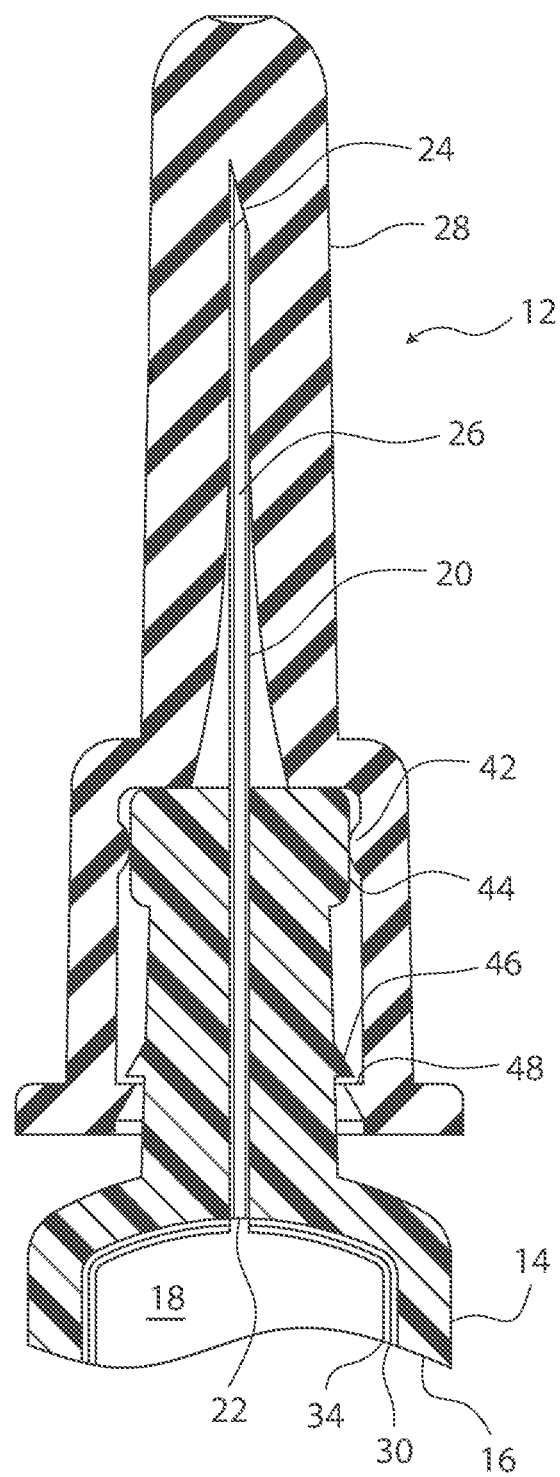
FIG. 5 is an enlarged fragmentary view of the capped assembly of FIG. 3.

Referring to FIGS. 1 and 2, a vessel 214, here in the form of a disassembled pharmaceutical package 210 is shown. Several non-limiting examples of such pharmaceutical packages 210 or their parts are a syringe barrel, a vial, a cartridge, a bottle, a stopper, a needle, a plunger, or a cap.

The pharmaceutical package 210 of FIGS. 1 and 2 has a lumen 18 defined at least in part by a wall 15. At least a portion of the wall 15 optionally comprises a thermoplastic material, optionally cyclic olefin polymer. More generally, suitable materials for the wall 15 of the vessel 14 include a polyolefin (for example a cyclic olefin polymer, a cyclic olefin copolymer, or polypropylene), polyester, for example polyethylene terephthalate, a polycarbonate, or any combination or copolymer of any of these. A combination of any two or more of the materials in this paragraph can also be used.

The wall 15 has an interior surface 16 facing the lumen, an outer surface 216, and a vessel coating set 285 on at least a portion of the wall 15 facing the lumen 18. The interior surface 16 comprises a tie coating or layer 838, a barrier coating or layer 30, a pH protective coating or layer 34, and optionally a lubricity coating or layer 287. In this embodiment of the vessel coating set 285, the combination of the tie coating or layer 838, the barrier coating or layer 30, and the pH protective coating or layer 34 is sometimes known as a "trilayer coating" in which the barrier coating or layer 30 of $SiO_x$ optionally is protected against contents having a pH otherwise high enough to remove it by being sandwiched between the pH protective coating or layer 34 and the tie coating or layer 838, each an organic layer of $SiO_xC_y$ as defined in this specification.

FIGS. 1 and 2 show a vessel 14 having at least a single opening, and should be understood to include a vessel 14 having two or more openings, such as a syringe barrel. Tie Coating or Layer Referring to FIGS. 1 and 2, a tie coating or layer 838 is provided, sometimes referred to as an adhesion coating or layer. The tie coating or layer 838 optionally can be deposited by plasma enhanced chemical vapor deposition (PECVD) or other chemical vapor deposition processes on the vessel of a pharmaceutical package 210, for example a thermoplastic pharmaceutical package.

The tie coating or layer 838 optionally functions to improve adhesion of a barrier coating or layer 30 to a substrate such as the interior surface 16, in particular a thermoplastic substrate, although a tie coating or layer 838 can be used to improve adhesion to a glass substrate or to another coating or layer.

Optionally, the tie coating or layer 838 improves adhesion of the barrier coating or layer 30 to the substrate or wall 15. For example, the tie coating or layer 838 can be applied to the substrate and the barrier coating or layer 30 can be applied to the tie coating or layer 838 to improve adhesion of the barrier coating or layer 30 to the substrate. Optionally, the tie coating or layer 838 is also believed to relieve stress on the barrier coating or layer 30, making the barrier coating or layer 30 less subject to damage from thermal expansion or contraction or mechanical shock.

Optionally, the tie coating or layer 838 applied under a barrier coating or layer 30 can improve the function of a pH protective coating or layer 34 applied over the barrier coating or layer 30.

Optionally, the tie coating or layer 838 is also believed to decouple defects between the barrier coating or layer 30 and the thermoplastic substrate, here wall 15. This is believed to occur because any pinholes or other defects that may be formed when the tie coating or layer 838 is applied tend not to be continued when the barrier coating or layer 30 is applied, so the pinholes or other defects in one coating do not line up with defects in the other. Optionally, the tie coating or layer 838 has some efficacy as a barrier coating or layer 30, so even a defect providing a leakage path extending through the barrier coating or layer 30 is blocked by the tie coating or layer 838.

Optionally, the tie coating or layer 838 comprises $SiO_xC_y$, preferably can be composed of, comprise, or consist essentially of $SiO_xC_y$, wherein x is from about 0.5 to about 2.4 and y is from about 0.6 to about 3. The atomic ratios of Si, O, and C in the tie coating or layer 838 optionally can be:

Si 100: O 50-150: C 90-200 (i.e. x=0.5 to 1.5, y=0.9 to 2);
Si 100: O 70-130: C 90-200 (i.e. x=0.7 to 1.3, y=0.9 to 2)
Si 100: O 80-120: C 90-150 (i.e. x=0.8 to 1.2, y=0.9 to 1.5)
Si 100: O 90-120: C 90-140 (i.e. x=0.9 to 1.2, y=0.9 to 1.4), or
Si 100: O 92-107: C 116-133 (i.e. x=0.92 to 1.07, y=1.16 to 1.33).

The atomic ratio can be determined by XPS. Taking into account the H atoms, which are not measured by XPS, the tie coating or layer 838 may thus in one aspect have the formula $Si_wO_xC_yH$ (or its equivalent $SiO_xC_y$), for example where w is 1, x is from about 0.5 to about 2.4, y is from about 0.6 to about 3, and z is from about 2 to about 9. Typically, the tie coating or layer 838 would hence contain 36% to 41% carbon when normalized to 100% carbon plus oxygen plus silicon.

Optionally, the tie coating or layer 838 can be similar or identical in composition with the pH protective coating or layer 34 described elsewhere in this specification, although this is not a requirement.

Optionally, the tie coating or layer 838 is on average between 5 and 200 nm (nanometers), optionally between 5 and 100 nm, optionally between 5 and 20 nm thick. These thicknesses are not critical. Commonly but not necessarily, the tie coating or layer 838 will be relatively thin, since its function is to change the surface properties of the substrate.

The tie coating or layer 838 has an interior surface facing the lumen 18 and an outer surface facing the wall 15 interior surface 16. Optionally, the tie coating or layer 286 is at least coextensive with the barrier coating or layer. Optionally, the tie coating or layer is applied by PECVD, for example of a precursor feed comprising octamethylcyclotetrasiloxane (OMCTS), tetramethyldisiloxane (TMDSO), or hexamethyldisiloxane (HMDSO).

The thickness of the tie coating or layer 838 can be measured, for example, by transmission electron microscopy (TEM), and its composition can be measured by X-ray photoelectron spectroscopy (XPS).

Barrier Coating or Layer

Referring to FIGS. 1 and 2, a barrier coating or layer 30 optionally can be deposited by plasma enhanced chemical vapor deposition (PECVD) or other chemical vapor deposition processes on the vessel of a pharmaceutical package 210, for example a thermoplastic pharmaceutical package, to prevent oxygen, carbon dioxide, or other gases from entering the vessel, the barrier coating 288 optionally being effective to reduce the ingress of atmospheric gas into the lumen 210 compared to an uncoated pharmaceutical package 210, and/or to prevent leaching of the formulation 40 into or through the package wall, and to prevent sterilizing fluids such as hydrogen peroxide and ethylene oxide from permeating the thermoplastic wall and thus entering the lumen of the container.

The barrier coating or layer 30 optionally can be applied directly or indirectly to the thermoplastic wall 15 (for example the tie coating or layer 838 can be interposed between them) so that in the filled pharmaceutical package 210 the barrier coating or layer 30 is located between the inner or interior surface 16 of the wall 15 and the lumen 18 that is adapted to contain the formulation 40 to be stored. The barrier coating or layer 30 of $SiO_x$ is supported by the thermoplastic wall 15. The barrier coating or layer 30 as described elsewhere in this specification, or in U.S. Pat. No. 7,985,188, can be used in any embodiment.

The barrier coating or layer 30 optionally is characterized as an "$SiO_x$" coating, and contains silicon, oxygen, and optionally other elements, in which x, the ratio of oxygen to silicon atoms, is from about 1.5 to about 2.9, or 1.5 to about 2.6, or about 2. One suitable barrier composition is one where x is 2.3, for example.

Optionally, the barrier coating or layer 30 is from 2 to 1000 nm thick, optionally from 4 nm to 500 nm thick, optionally between 10 and 200 nm thick, optionally from 20 to 200 nm thick, optionally from 20 to 30 nm thick, and comprises $SiO_x$, wherein x is from 1.5 to 2.9. The barrier coating or layer 30 of $SiO_x$ has an interior surface 220 facing the lumen 18 and an outer surface 222 facing the interior surface of the tie coating or layer 838. For example, the barrier coating or layer 30 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The barrier coating or layer 30 can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick.

Ranges of from 4 nm to 500 nm thick, optionally from 7 nm to 400 nm thick, optionally from 10 nm to 300 nm thick, optionally from 20 nm to 200 nm thick, optionally from 20 to 30 nm thick, optionally from 30 nm to 100 nm thick are contemplated. Specific thickness ranges composed of any one of the minimum thicknesses expressed above, plus any equal or greater one of the maximum thicknesses expressed above, are expressly contemplated.

The thickness of the $SiO_x$ or other barrier coating or layer 30 can be measured, for example, by transmission electron microscopy (TEM), and its composition can be measured by X-ray photoelectron spectroscopy (XPS).

pH Protective Coating or Layer

Certain barrier coatings or layers 30 such as $SiO_x$ as defined here have been found to have the characteristic of being subject to being measurably diminished in barrier improvement factor in less than six months as a result of attack by certain relatively high pH contents of the coated vessel 14 as described elsewhere in this specification, particularly where the barrier coating or layer 30 directly contacts the formulation 40 or other contents. The inventors have found that a barrier coating or layer 30 of $SiO_x$ is eroded or dissolved by some fluids, for example aqueous compositions having a pH above about 5. Since coatings applied by chemical vapor deposition can be very thin—tens to hundreds of nanometers thick—even a relatively slow rate of erosion can remove or reduce the effectiveness of the barrier coating or layer 30 in less time than the desired shelf life of a pharmaceutical package 214. This is particularly a problem for aqueous formulations 40, since many of them have a pH of roughly 7, or more broadly in the range of 4 to 8, alternatively from 5 to 9, similar to the pH of blood and other human or animal fluids. The higher the pH of the formulation 40, the more quickly it erodes or dissolves the $SiO_x$ coating. Optionally, this problem can be addressed by protecting the barrier coating or layer 30, or other pH sensitive material, with a pH protective coating or layer 34.

The pH protective coating or layer 34 optionally provides protection of the underlying barrier coating or layer 30 against contents of the pharmaceutical package 210 having a pH from 4 to 8, including where a surfactant is present. For a pre-filled pharmaceutical package 210 that is in contact with the contents of the lumen 18 from the time it is manufactured to the time it is used, the pH protective coating or layer 34 optionally prevents or inhibits attack of the barrier coating or layer 30 sufficiently to maintain an effective oxygen barrier over the intended shelf life of the pre-filled pharmaceutical package 210. The rate of erosion, dissolution, or leaching (different names for related concepts) of the pH protective coating or layer 34, if directly contacted by a fluid, is less than the rate of erosion of the barrier coating or layer 30, if directly contacted by the fluid having a pH of from 5 to 9. The pH protective coating or layer 34 is effective to isolate a formulation 40 having a pH between 5 and 9 from the barrier coating or layer 30, at least for sufficient time to allow the barrier coating or layer 30 to act as a barrier during the shelf life of the pre-filled pharmaceutical package 210.

The inventors have further found that certain pH protective coatings or layers 34 of $SiO_xC_y$ formed from polysiloxane precursors, which pH protective coatings or layers 34 have a substantial organic component, do not erode quickly when exposed to fluids, and in fact erode or dissolve more slowly when the fluids have pHs within the range of 4 to 8 or 5 to 9. For example, at pH 8, the dissolution rate of a pH protective coating or layer 34 is quite slow. These pH protective coatings or layers 34 of $SiO_xC_y$ can therefore be used to cover a barrier coating or layer 30 of $SiO_x$, retaining the benefits of the barrier coating or layer 30 by protecting it from the formulation 40 in the pharmaceutical package 210. The pH protective coating or layer 34 is applied over at least a portion of the $SiO_x$ barrier coating or layer 30 to protect the barrier coating or layer 30 from contents stored in a pharmaceutical package 210, where the contents otherwise would be in contact with the barrier coating or layer 30 of $SiO_x$.

Effective pH protective coatings or layers 34 for avoiding erosion can be made from siloxanes as described in this disclosure. $SiO_xC_y$ coatings can be deposited from cyclic siloxane precursors, for example octamethylcyclotetrasiloxane (OMCTS), or linear siloxane precursors, for example hexamethyldisiloxane (HMDSO) or tetramethyldisiloxane (TMDSO).

The pH protective coating or layer 34 optionally is effective to keep the barrier coating or layer 30 at least substantially undissolved as a result of attack by the formulation 40 for a period of at least six months.

The pH protective coating or layer 34 optionally can prevent or reduce the precipitation of a compound or component of a formulation 40 (for example, polypeptides such as proteins, natural or synthetic DNA, and the like) in contact with the pH protective coating or layer 34, in comparison to the uncoated surface and/or to a barrier coated surface using HMDSO as precursor.

Referring to FIGS. 1 and 2, the pH protective coating or layer 34 can be composed of, comprise, or consist essentially of $Si_wO_xC_yH_z$ (or its equivalent $SiO_xC_y$), each as defined wherein x is from about 0.5 to about 2.4 and y is from about 0.6 to about 3. The atomic ratios of Si, O, and C in the pH protective coating or layer 34 optionally can be:

Si 100: O 50-150: C 90-200 (i.e. x=0.5 to 1.5, y=0.9 to 2);
Si 100: O 70-130: C 90-200 (i.e. x=0.7 to 1.3, y=0.9 to 2)
Si 100: O 80-120: C 90-150 (i.e. x=0.8 to 1.2, y=0.9 to 1.5)
Si 100: O 90-120: C 90-140 (i.e. x=0.9 to 1.2, y=0.9 to 1.4), or
Si 100: O 92-107: C 116-133 (i.e. x=0.92 to 1.07, y=1.16 to 1.33) or
Si 100: O 80-130: C 90-150.

Alternatively, the pH protective coating or layer 34 can have atomic concentrations normalized to 100% carbon, oxygen, and silicon, as determined by X-ray photoelectron spectroscopy (XPS), of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective coating or layer 34, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer 34 can be increased in comparison to the organosilicon precursor, and/or the atomic ratio of oxygen to silicon can be decreased in comparison to the organosilicon precursor.

Optionally, the pH protective coating or layer 34 can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a pH protective coating or layer 34 is contemplated in any embodiment that can be characterized by a sum formula wherein the atomic ratio C:O can be increased and/or the atomic ratio Si:O can be decreased in comparison to the sum formula of the organosilicon precursor.

The atomic ratio of Si O:C can be determined by XPS (X-ray photoelectron spectroscopy). Taking into account the H atoms, the pH protective coating or layer 34 may thus in one aspect have the formula $Si_wO_xC_yH_z$, or its equivalent $SiO_xC_y$, for example where w is 1, x is from about 0.5 to about 2.4, y is from about 0.6 to about 3, and z is from about 2 to about 9.

The thickness of the pH protective coating or layer 34 as applied optionally is between 10 and 1000 nm; alternatively from 10 nm to 900 nm; alternatively from 10 nm to 800 nm; alternatively from 10 nm to 700 nm; alternatively from 10 nm to 600 nm; alternatively from 10 nm to 500 nm; alternatively from 10 nm to 400 nm; alternatively from 10 nm to 300 nm; alternatively from 10 nm to 200 nm; alternatively from 10 nm to 100 nm; alternatively from 10 nm to 50 nm; alternatively from 20 nm to 1000 nm; alternatively from 50 nm to 1000 nm; alternatively from 50 nm to 800 nm; optionally from 50 to 500 nm; optionally from 100 to 200 nm; alternatively from 100 nm to 700 nm; alternatively from 100 nm to 200 nm; alternatively from 300 to 600 nm. The thickness does not need to be uniform throughout the vessel, and will typically vary from the preferred values in portions of a vessel.

The pH protective coating or layer 34 can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR).

The pH protective coating or layer 34 optionally can have an RMS surface roughness value (measured by AFM) of from about 5 to about 9, optionally from about 6 to about 8, optionally from about 6.4 to about 7.8. The $R_a$ surface roughness value of the pH protective coating or layer 34, measured by AFM, can be from about 4 to about 6, optionally from about 4.6 to about 5.8. The $R_{max}$ surface roughness value of the pH protective coating or layer 34, measured by AFM, can be from about 70 to about 160, optionally from about 84 to about 142, optionally from about 90 to about 130.

The interior surface of the pH protective optionally can have a contact angle (with distilled water) of from 900 to 110°, optionally from 800 to 120°, optionally from 700 to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement."

Optionally an FTIR absorbance spectrum of the pH protective coating or layer 34 of any embodiment has a ratio greater than 0.75 between the maximum amplitude of the Si—O—Si symmetrical stretch peak normally located between about 1000 and 1040 cm-1, and the maximum amplitude of the Si—O—Si asymmetric stretch peak normally located between about 1060 and about 1100 cm-1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 1-5.

Optionally, in any embodiment the pH protective coating or layer 34, in the absence of the medicament, has a non-oily appearance. This appearance has been observed in some instances to distinguish an effective pH protective coating or layer 34 from a lubricity layer, which in some instances has been observed to have an oily (i.e. shiny) appearance.

Optionally, for the pH protective coating or layer 34 in any embodiment, the silicon dissolution rate by a 50 mM potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., is less than 170 ppb/day. (Polysorbate-80 is a common ingredient of pharmaceutical formulations, and is available for example as Tween®-80 from Uniqema Americas LLC, Wilmington Del.)

Optionally, for the pH protective coating or layer 34 in any embodiment, the silicon dissolution rate upon dissolution into a test composition with a pH of 8 from the vessel, is less than 160 ppb/day, or less than 140 ppb/day, or less than 120 ppb/day, or less than 100 ppb/day, or less than 90 ppb/day, or less than 80 ppb/day. Optionally, in any embodiment the silicon dissolution rate is more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here for the pH protective coating or layer 34 in any embodiment.

Optionally in any embodiment the total silicon content of the pH protective coating or layer 34 and barrier coating, upon dissolution into a test composition with a pH of 8 from the vessel, is less than 66 ppm, or less than 60 ppm, or less than 50 ppm, or less than 40 ppm, or less than 30 ppm, or less than 20 ppm.

The pH protective coating or layer 34 has an interior surface 224 facing the lumen 18 and an outer surface 226 facing the interior surface of the barrier coating or layer 30. Optionally, the pH protective coating or layer 34 is at least coextensive with the barrier coating or layer 30. The pH protective coating or layer 34 alternatively can be less extensive than the barrier coating, as when the formulation 40 does not contact or seldom is in contact with certain parts of the barrier coating or layer 30. The pH protective coating or layer 34 alternatively can be more extensive than the barrier coating, as it can cover areas that are not provided with a barrier coating.

The pH protective coating or layer 34 optionally can be applied by plasma enhanced chemical vapor deposition (PECVD) of a precursor feed comprising an acyclic siloxane, a monocyclic siloxane, a polycyclic siloxane, a polysilsesquioxane, a silatrane, a silquasilatrane, a silproatrane, or a combination of any two or more of these precursors. Some particular, non-limiting precursors contemplated for such use include octamethylcyclotetrasiloxane (OMCTS), HMDSO, or TMDSO.

Optionally, an FTIR absorbance spectrum of the pH protective coating or layer 34 has a ratio greater than 0.75 between the maximum amplitude of the Si—O—Si symmetrical stretch peak between about 1000 and 1040 cm$^{-1}$, and the maximum amplitude of the Si—O—Si asymmetric stretch peak between about 1060 and about 1100 cm$^{-1}$.

In the presence of a fluid composition having a pH between 5 and 9, optionally with a pH of 8 in the vessel, contained in the lumen 18, the calculated shelf life of the pharmaceutical package 210 is more than six months at a storage temperature of 4° C. Optionally, the rate of erosion of the pH protective coating or layer 34, if directly contacted by a fluid composition having a pH of 8, is less than 20% optionally less than 15%, optionally less than 10%, optionally less than 7%, optionally from 5% to 20%, optionally 5% to 15%, optionally 5% to 10%, optionally 5% to 7%, of the rate of erosion of the barrier coating or layer 30, if directly contacted by the same fluid composition under the same conditions. Optionally, the fluid composition removes the pH protective coating or layer 34 at a rate of 1 nm or less of pH protective coating or layer 34 thickness per 44 hours of contact with the fluid composition.

Optionally, the silicon dissolution rate of the pH protective coating or layer 34 and barrier coating or layer 30 by a 50 mM potassium phosphate buffer diluted in water for injection, adjusted to pH 8 with concentrated nitric acid, and containing 0.2 wt. % polysorbate-80 surfactant from the vessel is less than 170 parts per billion (ppb)/day.

Optionally, the total silicon content of the pH protective coating or layer 34 and the barrier coating or layer 30, upon dissolution into 0.1 N potassium hydroxide aqueous solution at 40° C. from the vessel, is less than 66 ppm.

Optionally, the calculated shelf life of the pharmaceutical package 210 (total Si/Si dissolution rate) is more than 2 years.

Optionally, the pH protective coating or layer 34 shows an O-Parameter measured with attenuated total reflection (ATR) FTIR of less than 0.4, measured as:

$$O\text{-}Parameter = \frac{\text{Intensity at 1253 cm}^{-1}}{\text{Maximum intensity in the range 1000 to 1100 cm}^{-1}}.$$

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression, for example on the plot shown as FIG. 5 of U.S. Pat. No. 8,067,070, except annotated to show interpolation of the wave number and absorbance scales to arrive at an absorbance at 1253 cm−1 of 0.0424 and a maximum absorbance at 1000 to 1100 cm−1 of 0.08, resulting in a calculated O-parameter of 0.53. The O-Parameter can also be measured from digital wave number versus absorbance data.

U.S. Pat. No. 8,067,070 asserts that the claimed O-parameter range provides a superior passivation coating. Surprisingly, it has been found by the present inventors that O-parameters outside the ranges claimed in U.S. Pat. No. 8,067,070 provide better results than are obtained in U.S. Pat. No. 8,067,070. Alternatively in the embodiment of FIGS. 1-5, the O-parameter has a value of from 0.1 to 0.39, or from 0.15 to 0.37, or from 0.17 to 0.35.

Optionally, the pH protective coating or layer 34 shows an N-Parameter measured with attenuated total reflection (ATR) of less than 0.7, measured as:

$$N\text{-}Parameter = \frac{\text{Intensity at 840 cm}^{-1}}{\text{Intensity at 799 cm}^{-1}}.$$

The N-Parameter is also described in U.S. Pat. No. 8,067,070, and is measured analogously to the O-Parameter except that intensities at two specific wave numbers are used—neither of these wave numbers is a range. U.S. Pat. No. 8,067,070 claims a passivation layer with an N-Parameter of 0.7 to 1.6. Again, the present inventors have made better coatings employing a pH protective coating or layer 34 having an N-Parameter lower than 0.7, as described above. Alternatively, the N-parameter has a value of at least 0.3, or from 0.4 to 0.6, or at least 0.53.

The protective coating or layer of $Si_wO_xC_y$ or its equivalent $SiO_xC_y$, also can have utility as a hydrophobic layer, independent of whether it also functions as a pH protective coating or layer 34. Suitable hydrophobic coatings or layers and their application, properties, and use are described in U.S. Pat. No. 7,985,188. Dual functional protective/hydrophobic coatings or layers having the properties of both types of coatings or layers can be provided for any embodiment of the present invention.

Lubricity Coating or Layer

Referring to the drawings, a method for preparing a lubricity coating or layer 287 on a plastic substrate such as the interior surface 16 of a pharmaceutical package 210, for example on its wall 15, is illustrated. When a vessel 14 is coated by the above coating method using PECVD, the coating method comprises several steps. A vessel 14 is provided having an open end, a closed end, and an interior surface. At least one gaseous reactant is introduced into the vessel 14. Plasma is formed within the vessel 14 under conditions effective to form a reaction product of the reactant, i.e. a coating, on the interior surface of the vessel 14.

Apparatus and general conditions suitable for carrying out this method are described in U.S. Pat. No. 7,985,188, which is incorporated here by reference in full.

The method includes providing a gas including an organosilicon precursor, optionally an oxidizing gas (for example 02), and an inert gas in the vicinity of the substrate surface. The inert gas optionally is a noble gas, for example argon, helium, krypton, xenon, neon, or a combination of two or more of these inert gases. Plasma is generated in the gas by providing plasma-forming energy adjacent to the plastic substrate. As a result, a lubricity coating or layer 287 is formed on the substrate surface such as 16 by plasma enhanced chemical vapor deposition (PECVD). Optionally, the plasma-forming energy is applied in a first phase as a first pulse at a first energy level, followed by further treatment in a second phase at a second energy level lower than the first energy level. Optionally, the second phase is applied as a second pulse.

A gaseous reactant or process gas can be employed having a standard volume ratio of, for example when a lubricity coating is prepared: from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor; from 1 to 100 standard volumes, optionally from 5 to 100 standard volumes, optionally from 10 to 70 standard volumes, of a carrier gas; from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

First Phase of Plasma Forming Energy

In any embodiment, the plasma optionally can be generated with microwave energy or RF energy. The plasma optionally can be generated with electrodes powered at a radio frequency, preferably at a frequency of from 10 kHz to less than 300 MHz, more preferably of from 1 to 50 MHz, even more preferably of from 10 to 15 MHz, most preferably at 13.56 MHz.

In any embodiment, the first pulse energy can be, for example, from 21 to 100 Watts, alternatively from 25 to 75 Watts; alternatively from 40 to 60 Watts.

In any embodiment, the ratio of the electrode power to the plasma volume for the first pulse optionally can be equal to or more than 5 W/ml, preferably is from 6 W/ml to 150 W/ml, more preferably is from 7 W/ml to 100 W/ml, most preferably from 7 W/ml to 20 W/ml.

In any embodiment, the first pulse optionally can be applied for 0.1 to 5 seconds, alternatively 0.5 to 3 seconds, alternatively 0.75 to 1.5 seconds. The first phase energy level optionally can be applied in at least two pulses. The second pulse is at a lower energy level than the first pulse. As a further option, the first phase energy level optionally can be applied in at least three pulses. The third pulse optionally can be at a lower energy level than the second pulse.

Second Phase of Plasma Forming Energy

In any embodiment, the second phase energy level optionally can be from 0.1 to 25 Watts, alternatively from 1 to 10 Watts, alternatively from 2 to 5 Watts.

Relation Between First and Second Phases

In any embodiment, the plasma-forming energy optionally can be applied in the first phase as a first pulse at a first energy level, followed by further treatment in a second phase at a second energy level.

Lubricity Profile

The lubricity coating optionally provides a consistent plunger force that reduces the difference between the break loose force ($F_i$) and the glide force ($F_m$). These two forces are important performance measures for the effectiveness of a lubricity coating. For $F_i$ and $F_m$, it is desired to have a low, but not too low value. With too low $F_i$, which means a too low level of resistance (the extreme being zero), premature/unintended flow may occur, which might e.g. lead to an unintentional premature or uncontrolled discharge of the content of a prefilled syringe.

Further advantageous $F_i$ and $F_m$ values can be found in the Tables of the Examples. Lower $F_i$ and $F_m$ values can be achieved than the ranges indicated above. Coatings having such lower values are also considered to be encompassed by the present invention.

Break-loose and glide forces are important throughout a device's shelf life especially in automated devices such as auto-injectors. Changes in break-loose and/or glide forces can lead to misfiring of auto injectors.

The vessels (e.g. syringe barrels and/or plungers) coated with a lubricity coating according to present invention have a higher lubricity, which means a lower $F_i$ and/or $F_m$ (determined, e.g. by measuring the $F_i$ and/or $F_m$) than the uncoated vessels. They also have a higher lubricity than vessels coated with an $SiO_x$ coating as described herein at the external surface.

Another aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of carbon, normalized to 100% of carbon, oxygen, and silicon, as determined by X-ray photoelectron spectroscopy (XPS), greater than the atomic concentration of carbon in the atomic formula for the feed gas.

Optionally, the atomic concentration of carbon increases by from 1 to 80 atomic percent (as calculated and based on the XPS conditions in Example 15 of EP 2 251 455), alternatively from 10 to 70 atomic percent, alternatively from 20 to 60 atomic percent, alternatively from 30 to 50 atomic percent, alternatively from 35 to 45 atomic percent, alternatively from 37 to 41 atomic percent in relation to the atomic concentration of carbon in the organosilicon precursor when a lubricity coating is made.

An additional aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of silicon, normalized to 100% of carbon, oxygen, and silicon, as determined by X-ray photoelectron spectroscopy (XPS), less than the atomic concentration of silicon in the atomic formula for the feed gas. See Example 15 of EP 2 251455.

Optionally, the atomic concentration of silicon decreases by from 1 to 80 atomic percent (as calculated and based on the XPS conditions in Example 15 of EP 2251 455), alternatively from 10 to 70 atomic percent, alternatively from 20 to 60 atomic percent, alternatively from 30 to 55 atomic percent, alternatively from 40 to 50 atomic percent, alternatively from 42 to 46 atomic percent.

The lubricity coating can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR).

Other types of lubricity coatings or layers 287 are also contemplated as alternatives to the plasma-applied SiOxCyHz coatings or layers just described in the illustrated embodiments. One example is a fluorinated polymer, for example polytetrafluoroethylene (PTFE), coating, and another is a crosslinked fluorinated polymer, e.g. perfluoropolyether (PFPE), or polysiloxane coating, e.g. crosslinked silicone oil.

The fluorinated polymer coating can be applied, for example, using a fluorinated precursor, by chemically modifying the precursor while on or in the vicinity of the fluid receiving interior surface.

Optionally, the precursor comprises: dimeric tetrafluoroparaxylylene; difluorocarbene; monomeric tetrafluoroethylene; oligomeric tetrafluoroethylene having the formula $F_2C=CF(CF_2)_xF$ in which x is from 1 to 100, optionally 2 to 50, optionally 2-20, optionally 2-10; sodium chlorodifluoroacetate; chlorodifluoromethane; bromodifluoromethane; hexafluoropropylene oxide; 1H,1H,2H,2H-perfluorodecyl acrylate (FDA); a bromofluoroalkane in which the alkane moiety has from 1 to 6 carbon atoms; an iodofluoroalkane in which the alkane moiety has from 1 to 6 carbon atoms; or a combination of any two or more of these.

The fluorinated polymer is: optionally from at least 0.01 micrometer to at most 100 micrometers thick; optionally from at least 0.05 micrometers to at most 90 micrometers thick; optionally from at least 0.1 micrometers to at most 80 micrometers thick; optionally from at least 0.1 micrometers to at most 70 micrometers thick; optionally from at least 0.1 micrometers to at most 60 micrometers thick; optionally from at least 0.1 micrometers to at most 50 micrometers thick; optionally from at least 0.1 micrometers to at most 40 micrometers thick; optionally from at least 0.1 micrometers to at most 30 micrometers thick; optionally from at least 0.1 micrometers to at most 20 micrometers thick; optionally from at least 0.1 micrometers to at most 15 micrometers thick; optionally from at least 0.1 micrometers to at most 12 micrometers thick; optionally from at least 0.1 micrometers to at most 10 micrometers thick; optionally from at least 0.1 micrometers to at most 8 micrometers thick; optionally from at least 0.1 micrometers to at most 6 micrometers thick; optionally from at least 0.1 micrometers to at most 4 micrometers thick; optionally from at least 0.1 micrometers to at most 2 micrometers thick; optionally from at least 0.1 micrometers to at most 1 micrometers thick; optionally from at least 0.1 micrometers to at most 0.9 micrometers thick; optionally from at least 0.1 micrometers to at most 0.8 micrometers thick; optionally from at least 0.1 micrometers to at most 0.7 micrometers thick; optionally from at least 0.1 micrometers to at most 0.6 micrometers thick; optionally from at least 0.1 micrometers to at most 0.5 micrometers thick; optionally from at least 0.5 micrometers to at most 5 micrometers thick; optionally from at least 0.5 micrometers to at most 4 micrometers thick; optionally from at least 0.5 micrometers to at most 3 micrometers thick; optionally from at least 0.5 micrometers to at most 2 micrometers thick; optionally from at least 0.5 micrometers to at most 1 micrometer thick; optionally about 10 micrometers thick; optionally about 2 micrometers thick.

The fluorinated polymer optionally can be applied by vapor deposition, for example chemical vapor deposition. Optionally, the fluorinated polymer can be applied by chemical vapor deposition of dimeric tetrafluoroparaxylylene. An example of a suitable fluorinated polymer is polytetrafluoroparaxylylene. Optionally, the fluorinated polymer consists essentially of polytetrafluoroparaxylylene.

Optionally in any embodiment, the fluorinated polymer coating or layer comprises polytetrafluoroethylene. Optionally in any embodiment, the fluorinated polymer coating or layer consists essentially of polytetrafluoroethylene.

For example, in any embodiment, the fluorinated polymer coating or layer can be applied by chemically modifying a precursor, while on or in the vicinity of the fluid receiving interior surface, to produce the fluorinated polymer coating or layer on the fluid receiving interior surface. Optionally in any embodiment, the fluorinated polymer coating or layer is applied by chemical vapor deposition. For one example, in any embodiment, the fluorinated polymer coating or layer can be applied by heated wire chemical vapor deposition (HWCVD). For another example, in any embodiment, the fluorinated polymer coating or layer can be applied by plasma enhanced chemical vapor deposition (PECVD). Mixed processes or other processes for applying a suitable coating are also contemplated, in any embodiment.

Another example of a suitable HWCVD process for applying the fluorinated polymer coating is the process described in Hilton G. Pryce Lewis, Neeta P. Bansal, Aleksandr J. White, Erik S. Handy, HWCVD of Polymers: Commercialization and Scale-up, THIN SOLID FILMS 517 (2009) 3551-3554; and US Publ. Appl. 2012/0003497 A1, published Jan. 5, 2012, which are incorporated here by reference in their entirety for their description of fluorinated polymer coatings and their application.

Optionally in any embodiment, the precursor comprises Parylene N or poly(paraxylylene); Parylene C or poly(2-chloroparaxylylene); Parylene D or poly(2,5-dichloroparaxylylene); Parylene HT® or poly(tetrafluoroparaxylylene), or their dimers, or a combination of two or more of these. Parylenes can be applied to a substrate as described by Specialty Coating Systems, Inc., discussed for example in Lonny Wolgemuth, Challenges With Prefilled Syringes: The Parylene Solution, www.ongrugdelivery.com, pp. 44-45 (Frederick Furness Publishing, 2012). The documents mentioned in this paragraph are incorporated by reference here.

The crosslinked perfluoropolyether (PFPE) or polysiloxane coating 287 can be applied, for example, by applying a liquid perfluoropolyether (PFPE) or polysiloxane to a surface, then treating it by exposing it to an energy source. An optional additional step comprises exposing the surface to an energy source, specifically an ionizing gas plasma at about atmospheric pressure, prior to the application of the lubricant. As a result of these methods, the lubricant resists migrating from the surface, thereby reducing the break-out force and sliding frictional force and reducing the introduction of the lubricant into the contents of a prefilled syringe thus lubricated.

The lubricant can be applied to the surface of the object by any of the numerous methods know in the art. By way of example, suitable application methods include spraying, atomizing, spin casting, painting, dipping, wiping, tumbling, and ultrasonics. The method used to apply the lubricant is not limited. The lubricant may be a fluorochemical compound or a polysiloxane-based compound.

The energy source can be an ionizing gas plasma. The gas may be a noble gas including, for example, helium, neon, argon, and krypton. Alternatively, the gas may be an oxidative gas including, for example, air, oxygen, carbon dioxide, carbon monoxide, and water vapor. In yet another alternative, the gas may be a non-oxidative gas including, for example, nitrogen and hydrogen. Mixtures of any of these gases may also be used.

The exact parameters under which the ionizing gas plasma are generated are not critical These parameters are selected based on factors including, for example, the gas in which the plasma is to be generated, the electrode geometry, frequency of the power source, and the dimensions of the surface to be treated. The treatment time may range from about 0.001 second to about 10 minutes, in addition ranging from about 0.001 second to about 5 minutes, and further in addition ranging from about 0.01 second to about 1 minute. The frequency may range from about 60 hertz to about 2.6 gigahertz, in addition ranging from about 1 kilohertz to about 100 kilohertz, and further in addition ranging from about 3 kilohertz to about 10 kilohertz. The power setting may be less than or equal to, for example, about 10 kilowatt.

The lubricant-coated surface also or instead can be exposed to ionizing radiation which provides the energy necessary to treat the lubricant. The ionizing radiation source can be gamma radiation or electron-beam radiation. Typically, commercial gamma irradiation processing systems use cobalt-60 as the gamma radiation source, although cesium-137 or other gamma radiation source may also be used. Commercial electron-beam radiation systems generate electrons from an electricity source using an electron gun assembly, accelerate the electrons, then focus the electrons into a beam. This beam of electrons is then directed at the material to be treated. The lubricant-coated surface may be exposed to an ionizing radiation dosage ranging from about 0.1 megarad to about 20 megarads, in addition ranging from about 0.5 megarad to about 15 megarads, and further in addition ranging from about 1 megarad to about 10 megarads.

The above and further details regarding the above process and the resulting lubricity coating or layer 287 are disclosed in U.S. Publ. Appl. 20040231926 A1, Sakhrani, et al., which is incorporated here by reference.

Graded Composite Layer

Another expedient contemplated here, for a barrier coating or layer 30 and an adjacent pH protective coating or layer 34, is a graded composite of any two or more adjacent PECVD layers, for example the barrier coating or layer 30 and a pH protective coating or layer 34 and/or a lubricity coating or layer 287, as shown in FIG. 1. A graded composite can be separate layers of a pH protective coating or layer 34 and/or barrier coating or layer 30 with a transition or interface of intermediate composition between them, or separate layers of a protective and/or hydrophobic layer and SiO$_x$ with an intermediate distinct pH protective coating or layer 34 of intermediate composition between them, or a single coating or layer that changes continuously or in steps from a barrier coating or layer 30 and/or hydrophobic coating or layer to a pH protective coating or layer 34 or a lubricity coating or layer 287, going in a normal direction to the coating set 285.

The grade in the graded composite can go in either direction. For example, the barrier coating or layer 30 can be applied directly to the substrate, such as an interior surface 16, or to a tie coating or layer 838, and graduate to a pH protective coating or layer 34 further from the interior surface 16. It optionally can further graduate to another type of coating or layer, such as a hydrophobic coating or layer or a lubricity coating or layer 287. A graduated tie coating or layer 838 is particularly contemplated if a layer of one composition is better for adhering to the substrate, in which case the better-adhering composition can, for example, be applied directly to the substrate. It is contemplated that the more distant portions of the graded tie coating or layer can be less compatible with the substrate than the adjacent portions of the graded tie coating or layer, since at any point the tie coating or layer is changing gradually in properties, so adjacent portions at nearly the same depth of the tie coating or layer have nearly identical composition, and more widely physically separated portions at substantially different depths can have more diverse properties. It is also contemplated that a tie coating or layer portion that forms a better barrier against transfer of material to or from the substrate can be directly against the substrate, to prevent the more remote tie coating or layer portion that forms a poorer barrier from being contaminated with the material intended to be barred or impeded by the barrier.

The applied coatings or layers, instead of being graded, optionally can have sharp transitions between one layer and the next, without a substantial gradient of composition. Such a coating or layer can be made, for example, by providing the gases to produce a layer as a steady state flow in a non-plasma state, then energizing the system with a brief plasma discharge to form a coating or layer on the substrate. If a subsequent coating or layer is to be applied, the gases for the previous coating or layer are cleared out and the gases for the next coating or layer are applied in a steady-state fashion before energizing the plasma and again forming a distinct layer on the surface of the substrate or its outermost previous coating or layer, with little if any gradual transition at the interface.

An embodiment can be carried out under conditions effective to form a hydrophobic pH protective coating or layer 34 on the substrate. Optionally, the hydrophobic characteristics of the pH protective coating or layer 34 can be set by setting the ratio of the O$_2$ to the organosilicon precursor in the gaseous reactant, and/or by setting the electric power used for generating the plasma. Optionally, the pH protective coating or layer 34 can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the pH protective coating or layer 34 can be more hydrophobic than the uncoated surface.

PECVD Apparatus for Forming PECVD Coatings or Layers

PECVD apparatus, a system and precursor materials suitable for applying any of the PECVD coatings or layers described in this specification, specifically including the tie coating or layer 838, the barrier coating or layer 30, or the pH protective coating or layer 34 are described in PCT Publ. Appl. WO2014085348A2 or U.S. Pat. No. 7,985,188, which are incorporated by reference.

Figure 6:
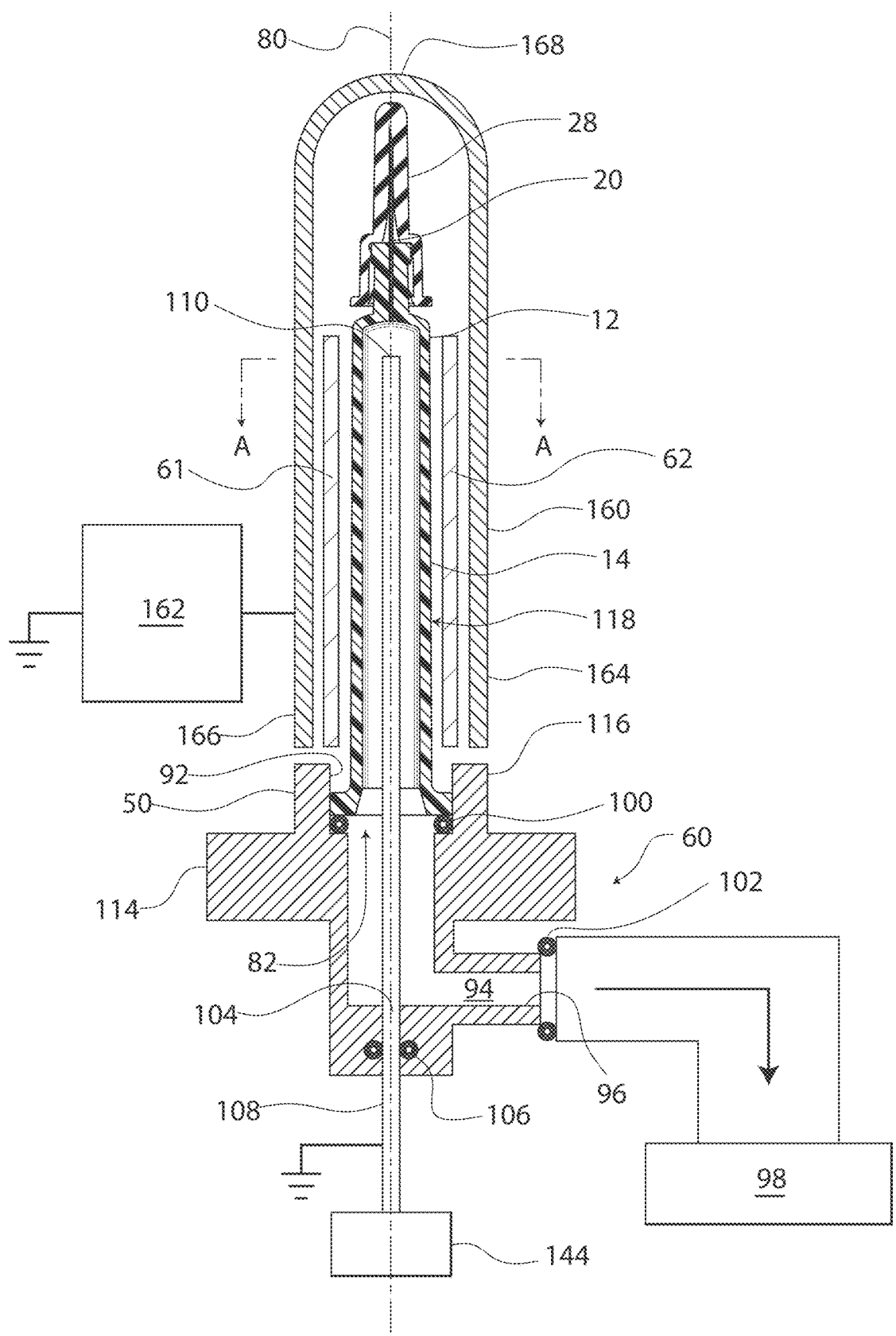
FIG. 6 is a schematic longitudinal section of the capped assembly of FIGS. 3 and 4 seated on a chemical vapor deposition coating station.
Figure 7:
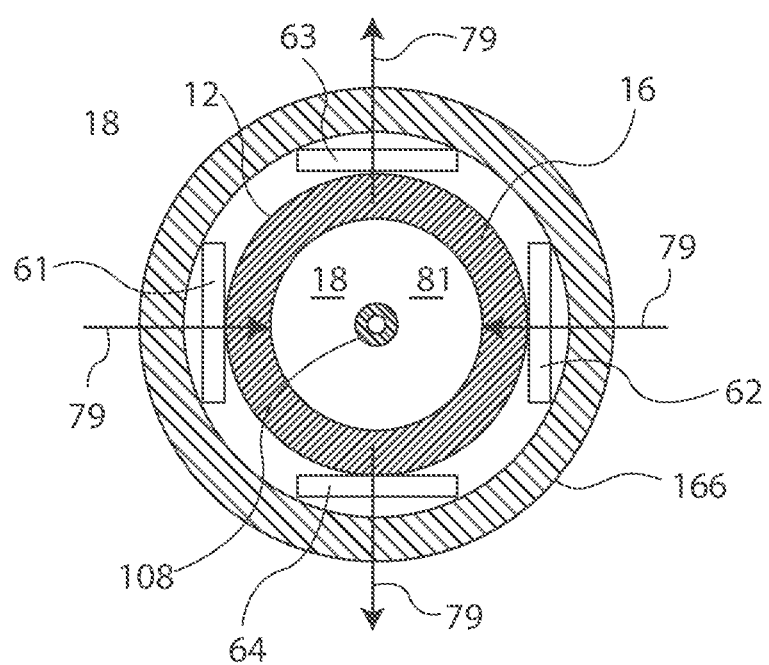
FIG. 7 is a section taken along section lines A A of FIG. 6, showing a rotatable quadrupole magnet array.
Figure 8:
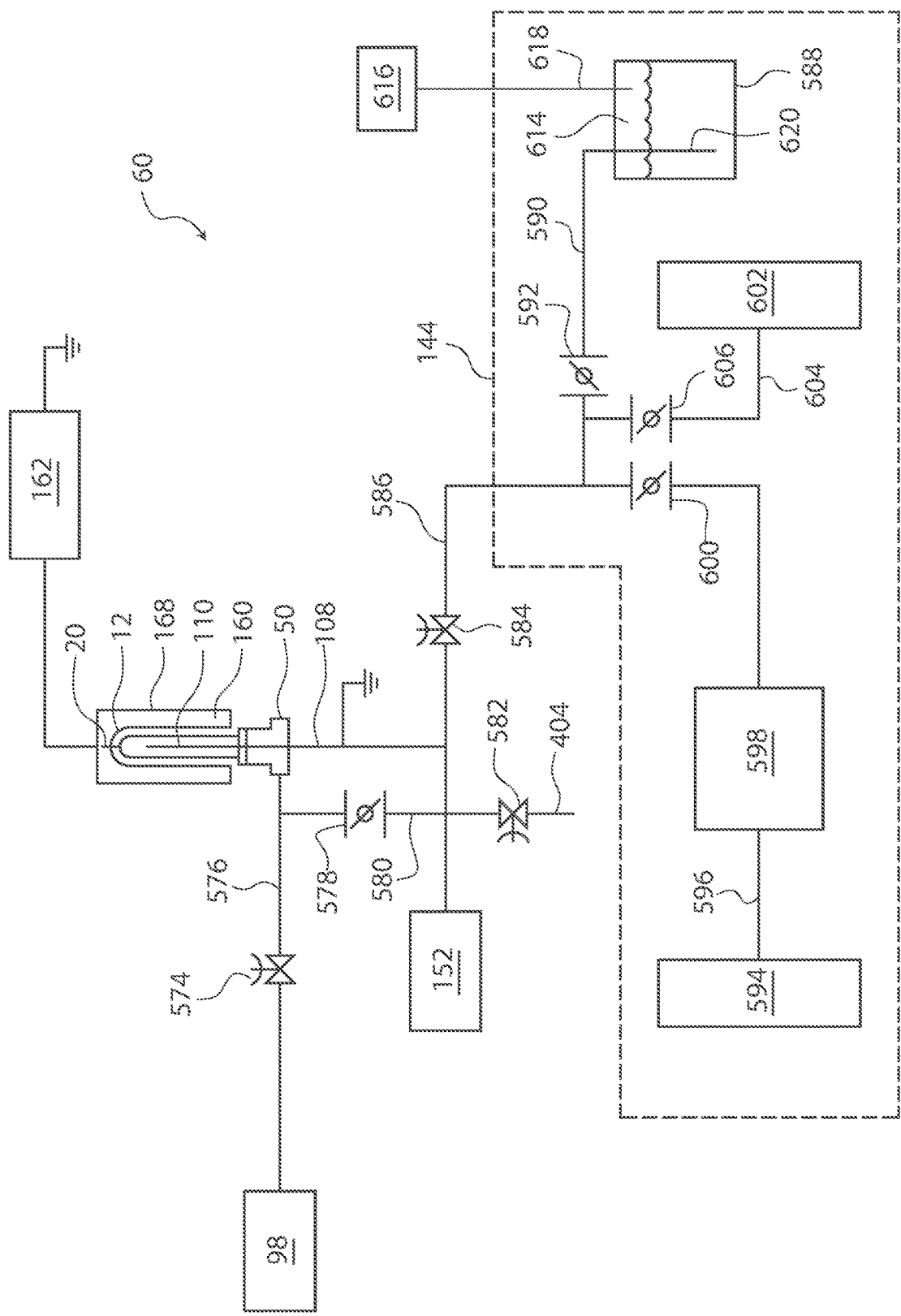
FIG. 8 is a schematic view showing more details of the chemical vapor deposition coating station shown in FIGS. 6-8.

An overview of these conditions is provided in FIGS. 6-8 which show a vessel processing system adapted for making such a vessel. A PECVD apparatus or coating station 60 suitable for the present purpose includes a vessel support 50, an inner electrode defined by the probe 108, an outer electrode 160, which optionally is generally cylindrical, and a power supply 162. The inner electrode 108 is located at least partially within the lumen of the vessel 14 during PECVD processing, and the outer electrode 160 is located outside the lumen of the vessel 14 during PECVD processing. The pre-capped assembly 12 seated on the vessel support 50 has a vessel 14 that defines a plasma reaction chamber, which optionally can be a vacuum chamber. Optionally, a source of vacuum 98, a reactant gas source 144, a gas feed (probe 108) or a combination of two or more of these can be supplied.

In any embodiment of the invention, the PECVD apparatus is contemplated for applying a PECVD set of one or more coatings on a vessel 14, particularly on its wall having a generally cylindrical inner surface defining a lumen, the generally cylindrical inner surface having a diameter in the range from 4 to 15 mm, for example, although these limits are not critical.

The PECVD apparatus can be used for atmospheric-pressure PECVD, in which case the plasma reaction chamber defined by the pre-capped assembly 12 does not need to function as a vacuum chamber.

Referring to FIGS. 6-8, the vessel support 50 comprises a gas inlet port 104 for conveying a gas into the pre-capped assembly 12 seated on the opening 82. The gas inlet port 104 can have a sliding seal provided for example by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 1 10. The distal end 1 10 of the illustrated embodiment can be inserted at an appropriate depth in the pre-capped assembly 12 for providing one or more PECVD reactants and other precursor feed or process gases. The inner electrode defined by the probe 108 has an outer surface including an end or distal portion 1 10 extending into the lumen and coaxial with and (optionally) radially spaced from 10.2 to 6.9 mm. from the generally cylindrical inner surface. The inner electrode 108 has an internal passage or gas delivery port 110 for supplying feed materials, having at least one outlet for introducing a gaseous PECVD precursor into the lumen, optionally one or more perforations or the port 110, for example. Electromagnetic energy can be applied to the outer electrode 160 under conditions effective to form a plasma enhanced chemical vapor deposition (PECVD) gas barrier coating having the desired mean thickness on the generally cylindrical inner surface.

FIG. 8 shows additional optional details of the coating station 60 that are usable, for example, with all the illustrated embodiments. The coating station 60 can also have a main vacuum valve 574 in its vacuum line 576 leading to the pressure sensor 152. A manual bypass valve 578 can be provided in the bypass line 580. A vent valve 582 controls flow at the vent 404.

Flow out of the PECVD gas or precursor source 144 can be controlled by a main reactant gas valve 584 regulating flow through the main reactant feed line 586. One component of the gas source 144 can be the organosilicon liquid reservoir 588, containing the precursor. The contents of the reservoir 588 can be drawn through the organosilicon capillary line 590, which optionally can be provided at a suitable length to provide the desired flow rate. Flow of organosilicon vapor can be controlled by the organosilicon shut-off valve 592. Pressure can be applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 can be sealed and the capillary connection 620 can be at the bottom of the reservoir 588 to ensure that only neat organosilicon liquid (not the pressurized gas from the headspace 614) flows through the capillary tube 590. The organosilicon liquid optionally can be heated above ambient temperature, if necessary or desirable to cause the organosilicon liquid to evaporate, forming an organosilicon vapor. To accomplish this heating, the apparatus can advantageously include heated delivery lines from the exit of the precursor reservoir to as close as possible to the gas inlet into the syringe. Preheating can be useful, for example, when feeding OMCTS.

Oxidant gas can be provided from the oxidant gas tank 594 via an oxidant gas feed line 596 controlled by a mass flow controller 598 and provided with an oxidant shut-off valve 600.

Optionally in any embodiment, other precursor, oxidant, and/or diluent gas reservoirs such as 602 can be provided to supply additional materials if needed for a particular deposition process. Each such reservoir such as 602 can have an appropriate feed line 604 and shut-off valve 606.

Referring especially to FIG. 6, the processing station 60 can include an outer electrode 160 fed by a radio frequency power supply 162 for providing an electric field for generating plasma within the pre-capped assembly 12 during processing. In this embodiment, the probe 108 can be electrically conductive and can be grounded, thus providing a counter-electrode within the pre-capped assembly 12. Alternatively, in any embodiment the outer electrode 160 can be grounded and the probe 108 can be directly connected to the power supply 162.

In the embodiment of FIGS. 6-8, the outer electrode 160 can either be generally cylindrical as illustrated in FIGS. 6 and 7 or a generally U-shaped elongated channel. Each illustrated embodiment can have one or more sidewalls, such as 164 and 166, and optionally a top end 168, disposed about the pre-capped assembly 12 in close proximity.

Optionally in any embodiment, the outer electrode (160) can be made of foraminous material, for example a metal wire mesh material. Alternatively, the outer electrode (160) can be made of continuous material (meaning not perforated, woven, knitted or felted, for example), such as a metal cylinder.

Optionally in any embodiment, the inner electrode (108) extends axially into the lumen (18).

Optionally in any embodiment, the plasma modification of the surface (16) of the workpiece (12) comprises chemical vapor deposition, optionally plasma enhanced chemical vapor deposition (PECVD).

As was previously indicated, the inner electrode (108) optionally can do double duty as a material supply tube (104) for providing gaseous material to the lumen (18). The material supply tube (104) optionally, in any embodiment, has a wall disposed within the lumen (18).

Optionally in any embodiment, the wall has perforations to pass gaseous material to the lumen (18).

Optionally, further steps can be carried out by the system. For example, the coated vessels can be conveyed to a fluid filler which places formulation 40 from a fluid supply into the lumens of the coated vessels.

For another example the filled vessels can be conveyed to a closure installer, which takes closures, for example plungers or stoppers, from a closure supply and seats them in the lumens of the coated vessels.

Reaction conditions for forming the $SiO_x$ barrier coating or layer 30 are described in U.S. Pat. No. 7,985,188, which is incorporated by reference.

The tie coating or layer (also referred to as an adhesion coating or layer) can be produced, for example, using as the precursor tetramethyldisiloxane (TMDSO) or hexamethyldisiloxane (HMDSO) at a flow rate of 0.5 to 10 sccm, preferably 1 to 5 sccm; oxygen flow of 0.25 to 5 sccm, preferably 0.5 to 2.5 sccm; and argon flow of 1 to 120 sccm, preferably in the upper part of this range for a 1 mL syringe and the lower part of this range for a 5 ml. vial. The overall pressure in the vessel during PECVD can be from 0.01 to 10 Torr, preferably from 0.1 to 1.5 Torr. The power level applied can be from 5 to 100 Watts, preferably in the upper part of this range for a 1 mL syringe and the lower part of this range for a 5 ml. vial. The deposition time (i.e. "on" time for RF power) is from 0.1 to 10 seconds, preferably 1 to 3 seconds. The power cycle optionally can be ramped or steadily increased from 0 Watts to full power over a short time period, such as 2 seconds, when the power is turned on, which may improve the plasma uniformity. The ramp up of power over a period of time is optional, however.

The pH protective coating or layer 34 coating or layer described in this specification can be applied in many different ways. For one example, the low-pressure PECVD process described in U.S. Pat. No. 7,985,188 can be used. For another example, instead of using low-pressure PECVD, atmospheric PECVD can be employed to deposit the pH protective coating or layer 34. For another example, the coating can be simply evaporated and allowed to deposit on the $SiO_x$ layer to be protected. For another example, the coating can be sputtered on the $SiO_x$ layer to be protected. For still another example, the pH protective coating or layer 34 can be applied from a liquid medium used to rinse or wash the $SiO_x$ layer.

Pharmaceutical Package

The pharmaceutical package 210 illustrated most broadly by FIGS. 1 and 2 is contemplated in any embodiment.

FIGS. 1-5 and 10 illustrate several exemplary pharmaceutical packages or other vessels 210 including a wall 15 enclosing a lumen 18, a formulation 40 in the lumen 18, and a vessel coating set 285. The formulation 40 is contained in the lumen 18. Optionally for any of the embodiments of FIGS. 1-5, the formulation 40 is an aqueous fluid having a pH between 5 and 6, optionally between 6 and 7, optionally between 7 and 8, optionally between 8 and 9, optionally between 6.5 and 7.5, optionally between 7.5 and 8.5, optionally between 8.5 and 9. Optionally, the pH protective coating or layer 34 is effective to isolate a formulation 40 from the barrier coating 288. Optionally, the rate of erosion of the pH protective coating or layer 34, if directly contacted by an aqueous formulation 40 having a pH between 5 and 9, is less than the rate of erosion of the barrier coating 288, if directly contacted by an aqueous formulation 40 having a pH between 5 and 9. Optionally for any of the embodiments of FIGS. 1-5, the pharmaceutical package 210 can have a shelf life, after the pharmaceutical package 210 is assembled, of at least one year, alternatively at least two years.

Optionally for any of the embodiments of FIGS. 1-5, the shelf life is measured at 3° C., alternatively at 4° C. or higher, alternatively at 20° C. or higher, alternatively at 23° C., alternatively at 40° C.

Figure 9:
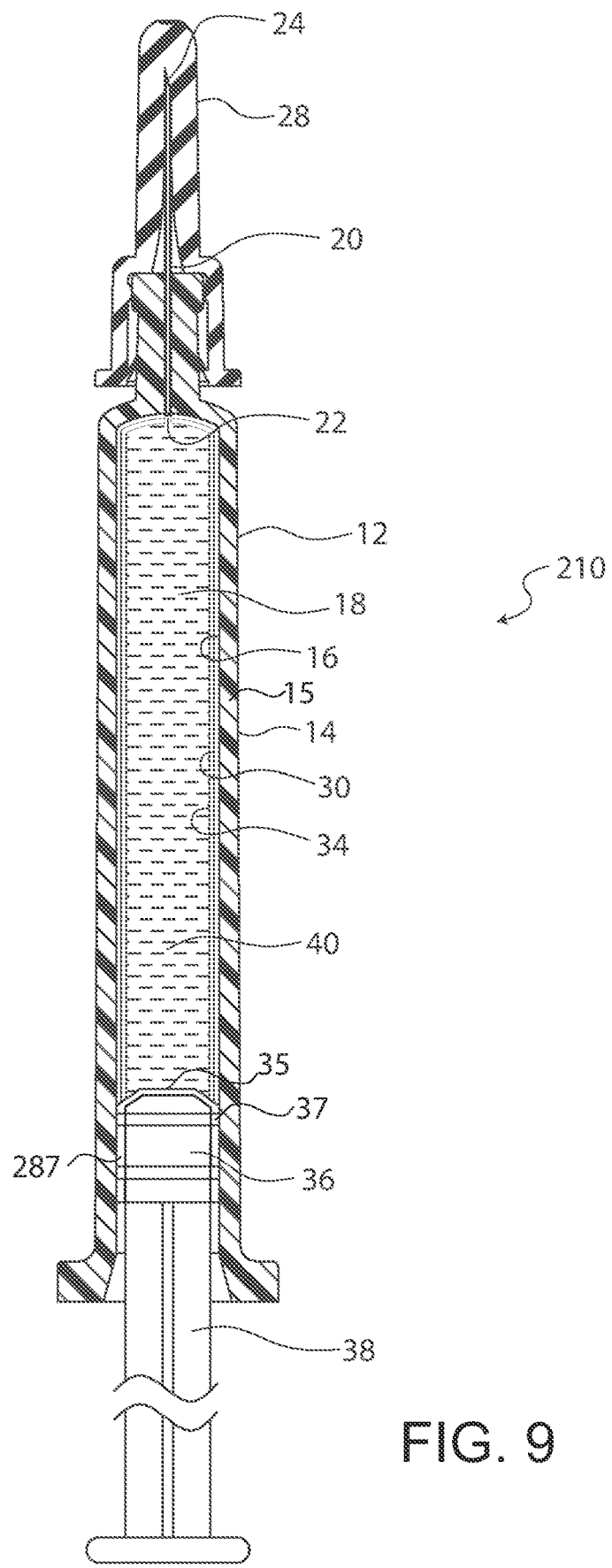
FIG. 9 is a view similar to FIG. 4 of the capped assembly of FIGS. 1-5, filled with a formulation 40 and fitted with a plunger tip, piston, stopper, or seal to define a pre-filled pharmaceutical package 210 embodied as a pre-filled syringe. In the option shown, a plunger tip, piston, stopper, or seal and plunger rod are installed.
Figure 10:
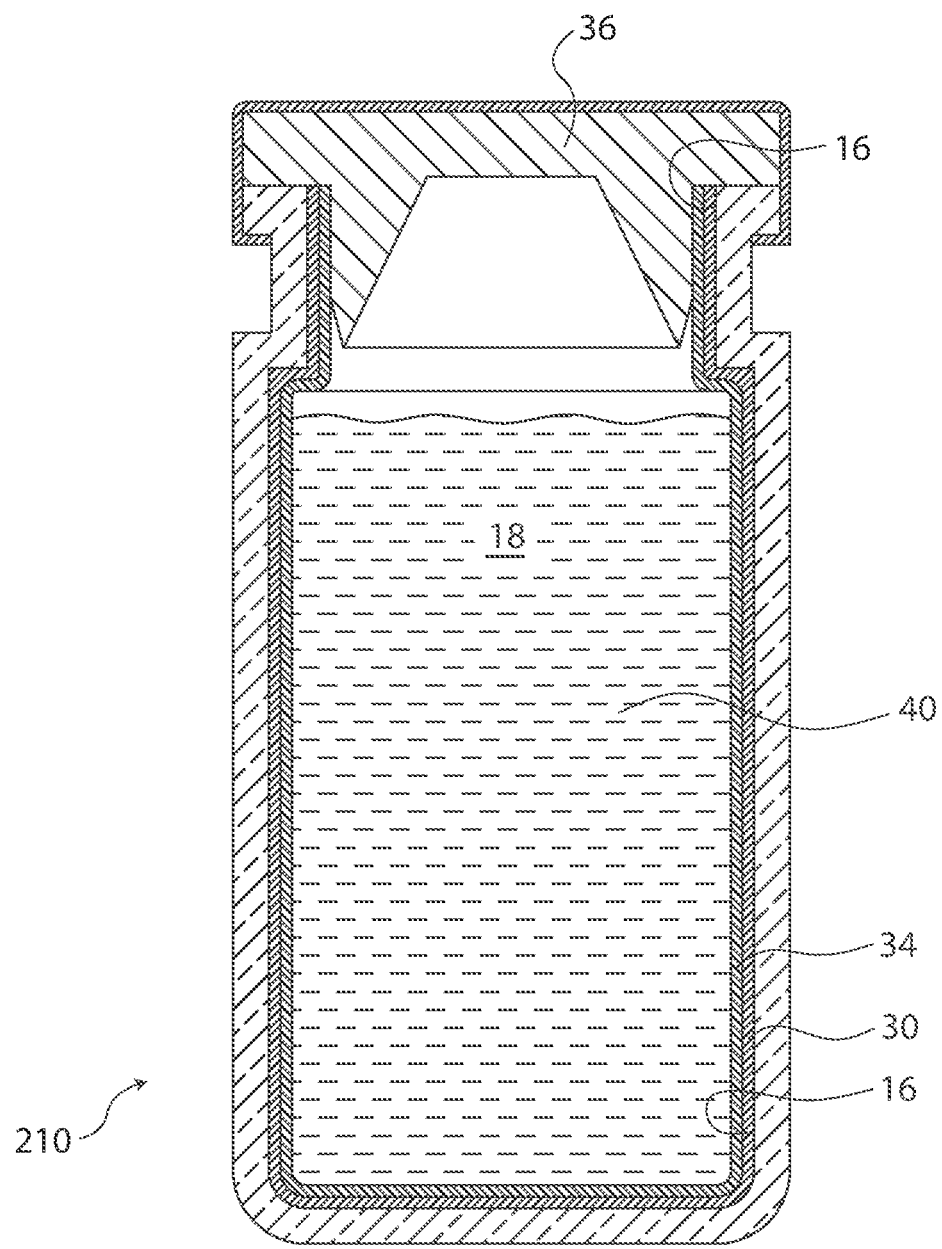
FIG. 10 is a longitudinal section of a pharmaceutical package 210 embodied as a vial fitted with a closure (septum and crimp) and having the same barrier coating or layer, passivation layer or pH protective coating, and other common features.

Referring to FIG. 9, the pharmaceutical package 210 embodied as a syringe optionally comprises a stopper 36 embodied as a plunger inserted in the barrel 14 and a plunger rod 38. The plunger 36 optionally is provided with a lubricity coating or layer 287, at least on its surface in contact with the barrel interior surface 16. The lubricity coating or layer 287 on the plunger is in the right position to prevent "sticktion" during storage and to continue to lower the friction between the plunger tip and barrel when the plunger is advanced, and if applied by CVD is contemplated to be less subject to displacement by the force exerted by the plunger tip on the barrel than traditional silicon oil coatings or layers and more uniformly applied as a uniform coating rather than as isolated droplets of liquid.

Protocols AND TEST METHODS
Atomic Composition

The atomic compositions of the tie coating or layer, the barrier coating or layer 30, and the pH protective coating or layer 34 are characterized using X-Ray Photoelectron Spectroscopy (XPS), to measure silicon, oxygen, and carbon, and either Rutherford backscattering (RBS) or hydrogen forward scattering (HFS) spectrometry to measure hydrogen. A separate analytical method is used to determine the hydrogen content because XPS does not detect hydrogen. The following methods are used, unless otherwise expressly indicated.

XPS Protocol

XPS data is quantified using relative sensitivity factors and a model that assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

The following analytical parameters are used:

| | |
|---|---|
| Instrument: | PHI Quantum 2000 |
| X-ray source: | Monochromated AlKa 1486.6 eV |
| Acceptance Angle | ±23° |
| Take-off angle | 45° |
| Analysis area | 600 μm |
| Charge Correction | C1s 284.8 eV |
| Ion Gun Conditions | Ar+, 1 keV, 2 × 2 mm raster |
| Sputter Rate | 15.6 Å/min (SiO2 Equivalent) |

Values given are normalized to 100 percent using the elements detected. Detection limits are approximately 0.05 to 1.0 atomic percent.

Rutherford Backscattering Spectrometry (RBS)

RBS spectra are acquired at a backscattering angle of 160° and an appropriate grazing angle (with the sample oriented perpendicular to the incident ion beam). The sample is rotated or tilted with a small angle to present a random geometry to the incident beam. This avoids channeling in both the film and the substrate. The use of two detector angles can significantly improve the measurement accuracy for composition when thin surface layers need to be analyzed.

When a thin (<100 nm) amorphous or polycrystalline film resides on a single crystal substrate, "ion channeling" may be utilized to reduce the backscattering signal from the substrate. This results in improved accuracy in the composition of layers containing elements that overlay with the substrate signal, typically light elements such as oxygen and carbon.

Analytical Parameters: RBS

| | |
|---|---|
| He++ Ion Beam Energy | 2.275 MeV |
| Normal Detector Angle | 160° |
| Grazing Detector Angle | ~100° |
| Analysis Mode | CC RR |

Spectra are fit by applying a theoretical layer model and iteratively adjusting elemental concentrations and thickness until good agreement is found between the theoretical and the experimental spectra.

Hydrogen Forward Scattering Spectrometry (HFS)

In an HFS experiment a detector is placed 30° from the forward trajectory of the incident He++ ion beam and the sample is rotated so that the incident beam strikes the surfaces 75° from normal. In this geometry it is possible to collect light atoms, namely hydrogen, forward-scattered from a sample after collisions with the probing He++ ion beam. A thin absorber foil is placed over the detector to filter out He++ ions that are also forward scattered from the sample.

Hydrogen concentrations are determined by comparing the number of hydrogen counts obtained from reference samples after normalizing by the stopping powers of the different materials. A hydrogen implanted silicon sample and a geological sample, muscovite, are used as references. The hydrogen concentration in the hydrogen implanted silicon sample is taken to be its stated implant dose of $1.6 \times 10 \pm 0.2 \times 10^{17}$ atoms/cm$^2$. The muscovite (MUSC) sample is known to have ~6.5±0.5 atomic percent hydrogen.

Samples are checked for hydrogen loss in the analyzed region. This is done by acquiring spectra for different acquisition times (initially a short exposure followed by a longer exposure to the He++ beam). Charge accumulations for 5 and 40 μC are used. A lower proportional signal in the 40 μC spectrum indicates hydrogen loss. In those cases the shorter exposure is chosen for analysis at the expense of higher noise in the spectrum. To account for surface hydrogen due to residual moisture or hydrocarbon adsorption a silicon control sample is analyzed together with the actual samples and the hydrogen signal from the control sample is subtracted from each of the spectra obtained from the actual samples. During the HFS acquisition backscattering spectra are acquired using the 160° angle detector (with the sample in forward scattering orientation). The RBS spectra are used to normalize the total charge delivered to the sample.

Analytical Parameters: HFS

| | |
|---|---|
| He++ Ion Beam Energy | 2.275 MeV |
| Normal Detector Angle | 160° |
| Grazing Detector Angle | ~30° |
| Ion Beam to Sample Normal | 75° |

Protocol for Total Silicon Measurement

This protocol is used to determine the total amount of silicon coatings present on the entire vessel wall. A supply of 0.1 N potassium hydroxide (KOH) aqueous solution is prepared, taking care to avoid contact between the solution or ingredients and glass. The water used is purified water, 18

MΩ quality. A Perkin Elmer Optima Model 7300DV ICP-OES instrument is used for the measurement except as otherwise indicated.

Each device (vial, syringe, tube, or the like) to be tested and its cap and crimp (in the case of a vial) or other closure are weighed empty to 0.001 g, then filled completely with the KOH solution (with no headspace), capped, crimped, and reweighed to 0.001 g. In a digestion step, each vial is placed in an autoclave oven (liquid cycle) at 121° C. for 1 hour. The digestion step is carried out to quantitatively remove the silicon coatings from the vessel wall into the KOH solution. After this digestion step, the vials are removed from the autoclave oven and allowed to cool to room temperature. The contents of the vials are transferred into ICP tubes. The total Si concentration is run on each solution by ICP/OES following the operating procedure for the ICP/OES.

The total Si concentration is reported as parts per billion of Si in the KOH solution. This concentration represents the total amount of silicon coatings that were on the vessel wall before the digestion step was used to remove it.

The total Si concentration can also be determined for fewer than all the silicon layers on the vessel, as when an $SiO_x$ barrier coating or layer 30 is applied, an $SiO_xC_y$ second layer (for example, a lubricity layer or a pH protective coating or layer 34) is then applied, and it is desired to know the total silicon concentration of just the $SiO_xC_y$ layer. This determination is made by preparing two sets of vessels, one set to which only the $SiO_x$ layer is applied and the other set to which the same $SiO_x$ layer is applied, followed by the $SiO_xC_y$ layer or other layers of interest. The total Si concentration for each set of vessels is determined in the same manner as described above. The difference between the two Si concentrations is the total Si concentration of the $SiO_xC_y$ second layer.

Protocol for Measuring Dissolved Silicon in a Vessel

In some of the working examples, the amount of silicon dissolved from the wall of the vessel by a test solution is determined, in parts per billion (ppb), for example to evaluate the dissolution rate of the test solution. This determination of dissolved silicon is made by storing the test solution in a vessel provided with an $SiO_x$ and/or $SiOC_y$ coating or layer under test conditions, then removing a sample of the solution from the vessel and testing the Si concentration of the sample. The test is done in the same manner as the Protocol for Total Silicon Measurement, except that the digestion step of that protocol is replaced by storage of the test solution in the vessel as described in this protocol. The total Si concentration is reported as parts per billion of Si in the test solution Protocol for Determining Average Dissolution Rate As shown in the working examples, the silicon dissolution rate is measured by determining the total silicon leached from the vessel into its contents, and does not distinguish between the silicon derived from the pH protective coating or layer 34, the lubricity layer 281, the barrier coating or layer 30, or other materials present.

The average dissolution rates reported in the working examples are determined as follows. A series of test vessels having a known total silicon measurement are filled with the desired test solution analogous to the manner of filling the vials with the KOH solution in the Protocol for Total Silicon Measurement. (The test solution can be a physiologically inactive test solution as employed in the present working examples or a physiologically active formulation 40 intended to be stored in the vessels to form a pharmaceutical package 210). The test solution is stored in respective vessels for several different amounts of time, and then analyzed for the Si concentration in parts per billion in the test solution for each storage time. The respective storage times and Si concentrations are then plotted. The plots are studied to find a series of substantially linear points having the steepest slope.

The plot of dissolution amount (ppb Si) versus days decreases in slope with time, even though it does not appear that the Si layer has been fully digested by the test solution.

For the PC194 test data in Table 10 below, linear plots of dissolution versus time data are prepared by using a least squares linear regression program to find a linear plot corresponding to the first five data points of each of the experimental plots. The slope of each linear plot is then determined and reported as representing the average dissolution rate applicable to the test, measured in parts per billion of Si dissolved in the test solution per unit of time.

Measurement of Coating Thickness

The thickness of a PECVD coating or layer such as the pH protective coating or layer 34, the barrier coating or layer 30, the lubricity coating or layer, and/or a composite of any two or more of these layers can be measured, for example, by transmission electron microscopy (TEM).

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered coating or layer of platinum (50-100 nm thick) using a K575X Emitech tie coating or layer system, or the samples can be coated directly with the protective sputtered Pt layer. The coated samples can be placed in an FEI FIB200 FIB system. An additional coating or layer of platinum can be FIB-deposited by injection of an organometallic gas while rastering the 30 kV gallium ion beam over the area of interest. The area of interest for each sample can be chosen to be a location half way down the length of the syringe barrel. Thin cross sections measuring approximately 15 m ("micrometers") long, 2 m wide and 15 m deep can be extracted from the die surface using an in-situ FIB lift-out technique. The cross sections can be attached to a 200 mesh copper TEM grid using FIB-deposited platinum. One or two windows in each section, measuring about 8 m wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | 2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |

-continued

| Instrument | Scanning Transmission Electron Microscope |
|---|---|
| Pixel Resolution | 1280 × 960 |
| Acquisition Time | 20 sec. (×4) |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | 1 |
| Objective Lens Aperture for imaging | 3 |
| Selective Area Aperture for SAD | N/A |

SEM Procedure

SEM Sample Preparation: Each syringe sample is cut in half along its length (to expose the inner or interior surface). The top of the syringe (Luer end) can be cut off to make the sample smaller.

The sample is mounted onto the sample holder with conductive graphite adhesive, then put into a Denton Desk IV SEM Sample Preparation System, and a thin (approximately 50 Å) gold coating is sputtered onto the inner or interior surface of the syringe. The gold coating is used to eliminate charging of the surface during measurement.

The sample is removed from the sputter system and mounted onto the sample stage of a Jeol JSM 6390 SEM (Scanning Electron Microscope). The sample is pumped down to at least $1\times10^{-6}$ Torr in the sample compartment. Once the sample reaches the required vacuum level, the slit valve is opened and the sample is moved into the analysis station.

The sample is imaged at a coarse resolution first, and then higher magnification images are accumulated. The SEM images can be, for example, 5 µm edge-to-edge (horizontal and vertical).

AFM (Atomic Force Microscopy) Procedure

AFM images are collected using a NanoScope III Dimension 3000 machine (Digital Instruments, Santa Barbara, Calif., USA). The instrument is calibrated against a NIST traceable standard. Etched silicon scanning probe microscopy (SPM) tips are used. Image processing procedures involving auto-flattening, plane fitting or convolution are employed. One 10 µm×10 µm area is imaged. Roughness analyses are performed and are expressed in: (1) Root-Mean-Square Roughness, RMS; 2 Mean Roughness, $R_a$; and (3) Maximum Height (Peak-to-Valley), $R_{max}$, all measured in nanometers (nm). For the roughness analyses, each sample is imaged over the 10 µm×10 µm area, followed by three cross sections selected by the analyst to cut through features in the 10 µm×10 µm images. The vertical depth of the features is measured using the cross section tool. For each cross section, a Root-Mean-Square Roughness (RMS) in nanometers is reported.

The Digital Instruments Nanoscope III AFM/STM acquires and stores 3-dimensional representations of surfaces in a digital format. These surfaces can be analyzed in a variety of ways.

The Nanoscope III software can perform a roughness analysis of any AFM or STM image. The product of this analysis is a single page reproducing the selected image in top view. The image can include an "Image Statistics" box, which lists the calculated characteristics of the whole image minus any areas excluded by a stopband (a box with an X through it). Similar additional statistics can be calculated for a selected portion of the image and these can be listed in the "Box Statistics" in the lower right portion of the page. What follows is a description and explanation of these statistics.

Image Statistics:

Z Range ($R_p$): The difference between the highest and lowest points in the image. The value is not corrected for tilt in the plane of the image; therefore, plane fitting or flattening the data will change the value.

Mean: The average of all of the Z values in the imaged area. This value is not corrected for the tilt in the plane of the image; therefore, plane fitting or flattening the data will change this value.

RMS($R_q$): This is the standard deviation of the Z values (or RMS roughness) in the image. It is calculated according to the formula:

$$Rq = \{\Sigma(Z_1 - Z_{avg})2/N\}$$

where $Z_{avg}$ is the average Z value within the image; $Z_1$ is the current value of Z; and N is the number of points in the image. This value is not corrected for tilt in the plane of the image; therefore, plane fitting or flattening the data will change this value.

Mean roughness ($R_a$): This is the mean value of the surface relative to the Center Plane and is calculated using the formula:

$$R_a = [1/(L_x L_y)] \int_0^{L_y} \int_0^{L_x} \{f(x,y)\} dx dy$$

where f(x,y) is the surface relative to the Center plane, and $L_x$ and $L_y$ are the dimensions of the surface.

Max height ($R_{max}$): This is the difference in height between the highest and lowest points of the surface relative to the Mean Plane.

Surface area: (Optical calculation): This is the area of the 3-dimensional surface of the imaged area. It is calculated by taking the sum of the areas of the triangles formed by 3 adjacent data points throughout the image.

Surface area diff: (Optional calculation) This is the amount that the Surface area is in excess of the imaged area. It is expressed as a percentage and is calculated according to the formula:

$$\text{Surface area diff} = 100[(\text{Surface area}/S_1 {-}1)]$$

where $S_1$ is the length (and width) of the scanned area minus any areas excluded by stopbands.

Center Plane: A flat plane that is parallel to the Mean Plane. The volumes enclosed by the image surface above and below the center plane are equal.

Mean Plane: The image data has a minimum variance about this flat plane. It results from a first order least squares fit on the Z data.

Spectral Reflectance Protocol for Thickness Mapping

A Filmetrics Thin-Film Analyzer Model 205-0436 F40 spectral reflectance instrument was used. The syringe is placed in a holder with the back end facing up and index marks on the back end dividing the circumference into 8 equal 45-degree segments. The instrument camera is focused on the coating or layer and a thickness measurement is acquired at 0 degrees on the circumference and 6 mm from the back end of the mapped area of the syringe barrel, vial, sample collection tube, or other vessel. Then the syringe is shifted 45 degrees, remaining at 6 mm axially, and another measurement is acquired. The process is repeated at 45 degree intervals around the syringe at 6 mm. The syringe is then advanced axially to 11 mm from the back end of the mapped area, and eight measurements are taken around the circumference. The syringe is successively advanced by 5 mm increments axially and 45 degree increments circumferentially to complete the map. The data is mapped using Filmetrics software. The mapped data can be analyzed statistically to determine the mean thickness and standard deviation values for the coated vessel.

Protocol for Lubricity Testing

The following materials are used in this test: [0146] Commercial (BD Hypak® PRTC) glass prefillable syringes with Luer-Lok® tip) (ca 1 mL) [0147] COC syringe barrels made according to the Protocol for Forming COC Syringe barrel; [0148] Commercial plastic syringe plungers with elastomeric tips taken from Becton Dickinson Product No. 306507 (obtained as saline prefilled syringes); [0149] Normal saline solution (taken from the Becton-Dickinson Product No. 306507 prefilled syringes); [0150] Dillon Test Stand with an Advanced Force Gauge (Model AFG-50N) [0151] Syringe holder and drain jig (fabricated to fit the Dillon Test Stand)

The following procedure is used in this test.

The jig is installed on the Dillon Test Stand. The platform probe movement is adjusted to 6 in/min (2.5 mm/sec) and upper and lower stop locations were set. The stop locations were verified using an empty syringe and barrel. The commercial saline-filled syringes were labeled, the plungers were removed, and the saline solution is drained via the open ends of the syringe barrels for re-use. Extra plungers were obtained in the same manner for use with the COC and glass barrels.

Syringe plungers were inserted into the COC syringe barrels so that the second horizontal molding point of each plunger is even with the syringe barrel lip (about 10 mm from the tip end). Using another syringe and needle assembly, the test syringes were filled via the capillary end with 2-3 milliliters of saline solution, with the capillary end uppermost. The sides of the syringe were tapped to remove any large air bubbles at the plunger/fluid interface and along the walls, and any air bubbles were carefully pushed out of the syringe while maintaining the plunger in its vertical orientation.

The samples were created by coating COC syringe barrels according to the Protocol for Coating COC Syringe Barrel Interior with OMCTS Lubricity layer. An alternative embodiment of the technology herein, would apply the lubricity layer or coating over another thin film coating, such as $SiO_x$, for example applied according to the Protocol for Coating COC Syringe barrel Interior with $SiO_x$.

Instead of the Dillon Test Stand and drain jig, a Genesis Packaging Plunger Force Tester (Model SFT-01 Syringe Force Tester, manufactured by Genesis Machinery, Lionville, Pa.) can also be used following the manufacturer's instructions for measuring Fi and Fm. The parameters that are used on the Genesis tester are: Start: 10 mm; Speed: 100 mm/min; Range: 20; Units: Newtons.

Examples A-C—Determination of Ranibizumab Stability in Glass Vs. Coated COP Pharmaceutical Packages Three types of pharmaceutical packages in the form of pre-filled syringes with stoppers, identified in Table 1, were made, filled with 167 μL of a Ranibizumab formulation, and tested for stability properties as described below.

TABLE 1

| Type | Syringe size | Syringe barrel | Coating | Stopper |
|---|---|---|---|---|
| A | 1.0 ml | Cyclo-olefin polymer (COP) | Trilayer | FluroTec ®* |
| B | 1.0 ml | Borosilicate glass | Baked on silicone | FluroTec ® |
| C | 1.0 ml | Cyclo-olefin polymer (COP) | Trilayer + Lubricity | FluroTec ® |

*Trademark of West Pharmaceutical Services, Inc. for commercial syringe plungers with FluroTec ® film laminate surfaces, adapted for use in pre-filled syringes.

The A and C type pharmaceutical packages used in testing (COP syringes with staked needles) were made as follows. Syringe barrels suitable for intravitreal injection, having a nominal maximum fill volume of 1 mL, illustrated by FIGS. 3-5, were injection molded from COP resin. The staked hypodermic needles were molded-in inserts, secured in place without using any glue. Needle shields 28 were installed on the syringe barrels and kept in place throughout the manufacturing process. The shields functioned both to protect the needle and, by burying the needle in the material of the shield, to seal off the needle. Sterilizing gas, in particular ethylene oxide, is able to penetrate the needle shield during sterilization to effectively sterilize the exterior of the needle and the air captured within the shield.

PECVD coaters, illustrated by FIGS. 6-8 and the accompanying text above, were used to apply adhesive, barrier, and pH protective coatings or layers to the inside of each Type A and Type C syringe barrel. The coating conditions in Tables 2-4 were used for the type A barrels, and the coating conditions in Tables 2-6 were used for the type B barrels.

TABLE 2

Adhesive Coating or Layer

| Variable | Units | Value |
|---|---|---|
| Net Power | WATTS | 20 |
| Ar | SCCM | 20 |
| TMDSO | SCCM | 2 |
| $O_2$ | SCCM | 1 |
| Plasma Duration | Time (sec.) | 2.5 |
| Plasma Start Delay | Time (sec.) | 15 |
| Vaporizer Temp. | CELSIUS | 90/80 |
| Reflected Power | WATTS | 0 |
| Chuck Pressure | TORR | 0.8 |
| Inlet Pressure | TORR | 17 |

TABLE 3

Barrier Coating or Layer

| Variable | Units | Value |
|---|---|---|
| Net Power | WATTS | 40 |
| HMDSO | SCCM | 0.75 |
| $O_2$ | SCCM | 75 |
| Plasma Duration | Time (sec.) | 10 |
| Plasma Start Delay | Time (sec.) | 10 |
| Vaporizer Temp. Controller | CELSIUS | 110/80 |

TABLE 3-continued

Barrier Coating or Layer

| Variable | Units | Value |
|---|---|---|
| Reflected Power | WATTS | 0 |
| Chuck Pressure | TORR | 1.5 |
| Inlet Pressure | TORR | 37.0 |

TABLE 4 pH Protective Coating or Layer

| Variable | Units | Value |
|---|---|---|
| Net Power | WATTS | 20 |
| Ar | SCCM | 20 |
| TMDSO | SCCM | 2 |
| $O_2$ | SCCM | 1 |
| Plasma Duration | Time (sec.) | 10 |
| Plasma Start Delay | Time (sec.) | 15 |
| Vaporizer Temp. Controller | CELSIUS | 90/80 |
| Chuck Pressure | TORR | 0.8 |
| Inlet Pressure | TORR | 17.0 |

TABLE 5

Lubricity Coating or Layer-Step 1

| Variable | Units | Value |
|---|---|---|
| Net Power | WATTS | 50 |
| Ar | SCCM | 7.5 |
| OMCTS | SCCM | 4 |
| $O_2$ | SCCM | 3.1 |
| Plasma Duration | Time (sec.) | 1 |
| Plasma Start Delay | Time (sec.) | 15 |
| Vaporizer Temp. Controller | CELSIUS | 120/100 |
| Main Vacuum Pressure | TORR | N/A |
| Chuck Pressure | TORR | N/A |
| Inlet Pressure | TORR | N/A |

TABLE 6

Lubricity Coating or Layer-Step 2

| Variable | Units | Value |
|---|---|---|
| Net Power | WATTS | 2 |
| Ar | SCCM | 7.5 |
| OMCTS | SCCM | 4 |
| $O_2$ | SCCM | 3.1 |
| Plasma Duration | Time (sec.) | 15 |
| Plasma Start Delay | Time (sec.) | 3 |
| Vaporizer Temp. Controller | CELSIUS | 120/100 |
| Main Vacuum Pressure | TORR | 0.045 |
| Chuck Pressure | TORR | 0.168 |
| Inlet Pressure | TORR | 3.45 |

Figure 11:
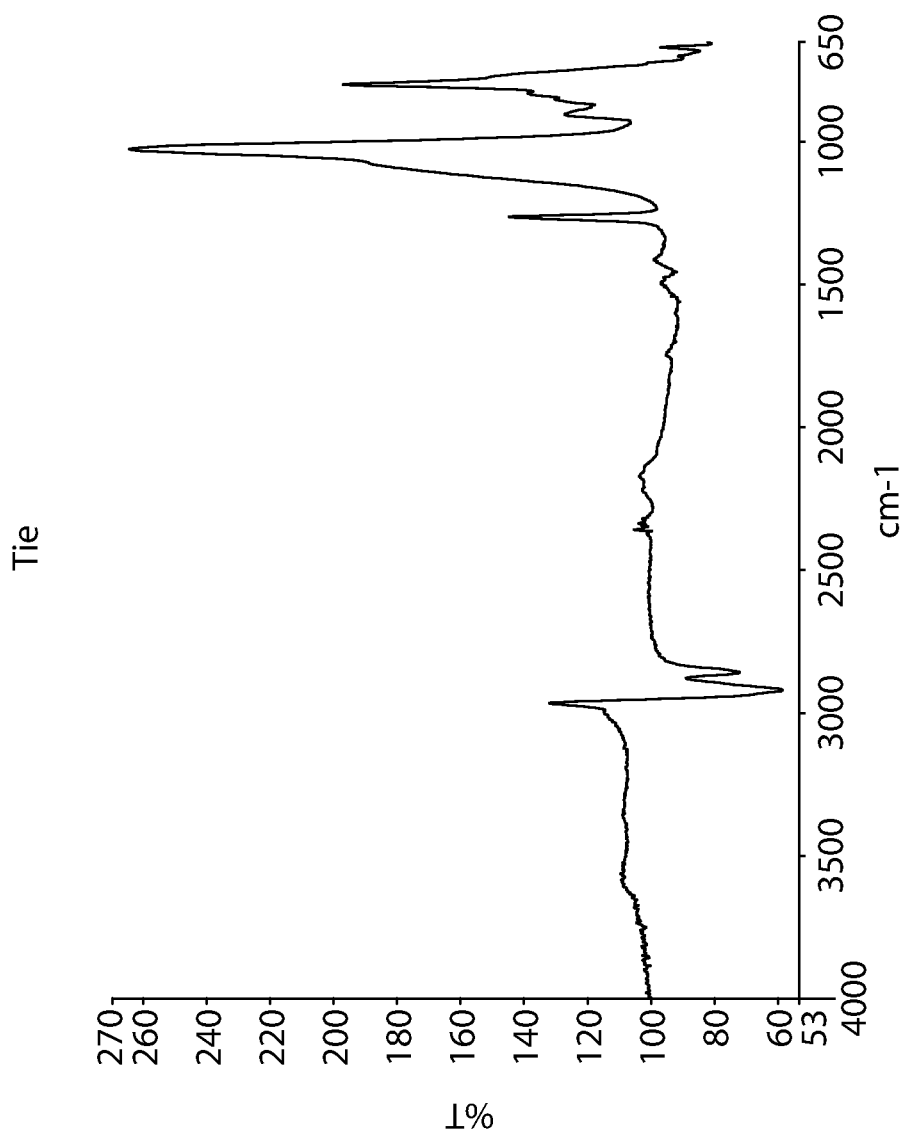
FIG. 11 is a Fourier-transform infrared spectrum representative of the tie coating or layer applied in Examples A and C, characterizing the coating chemistry.
Figure 12:
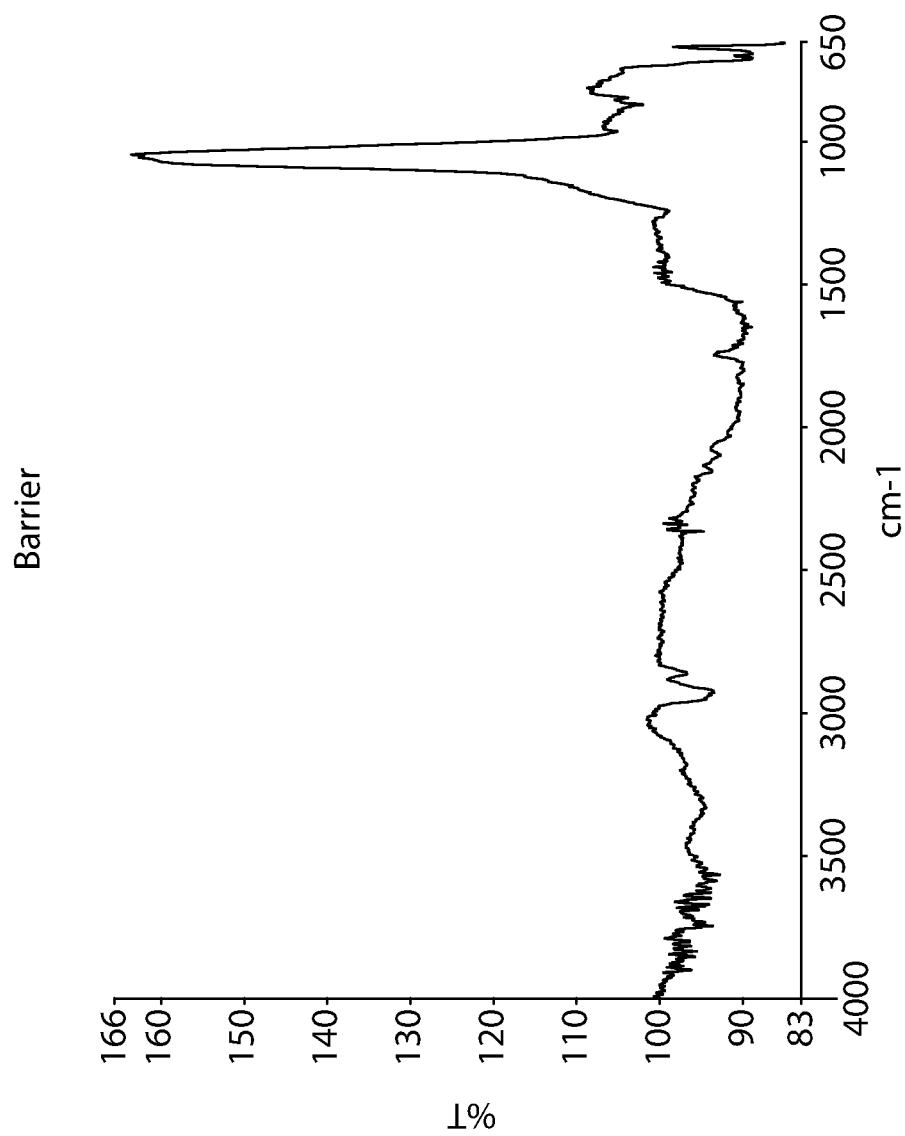
FIG. 12 is a Fourier-transform infrared spectrum representative of the barrier coating or layer applied in Examples A and C, characterizing the coating chemistry.
Figure 13:
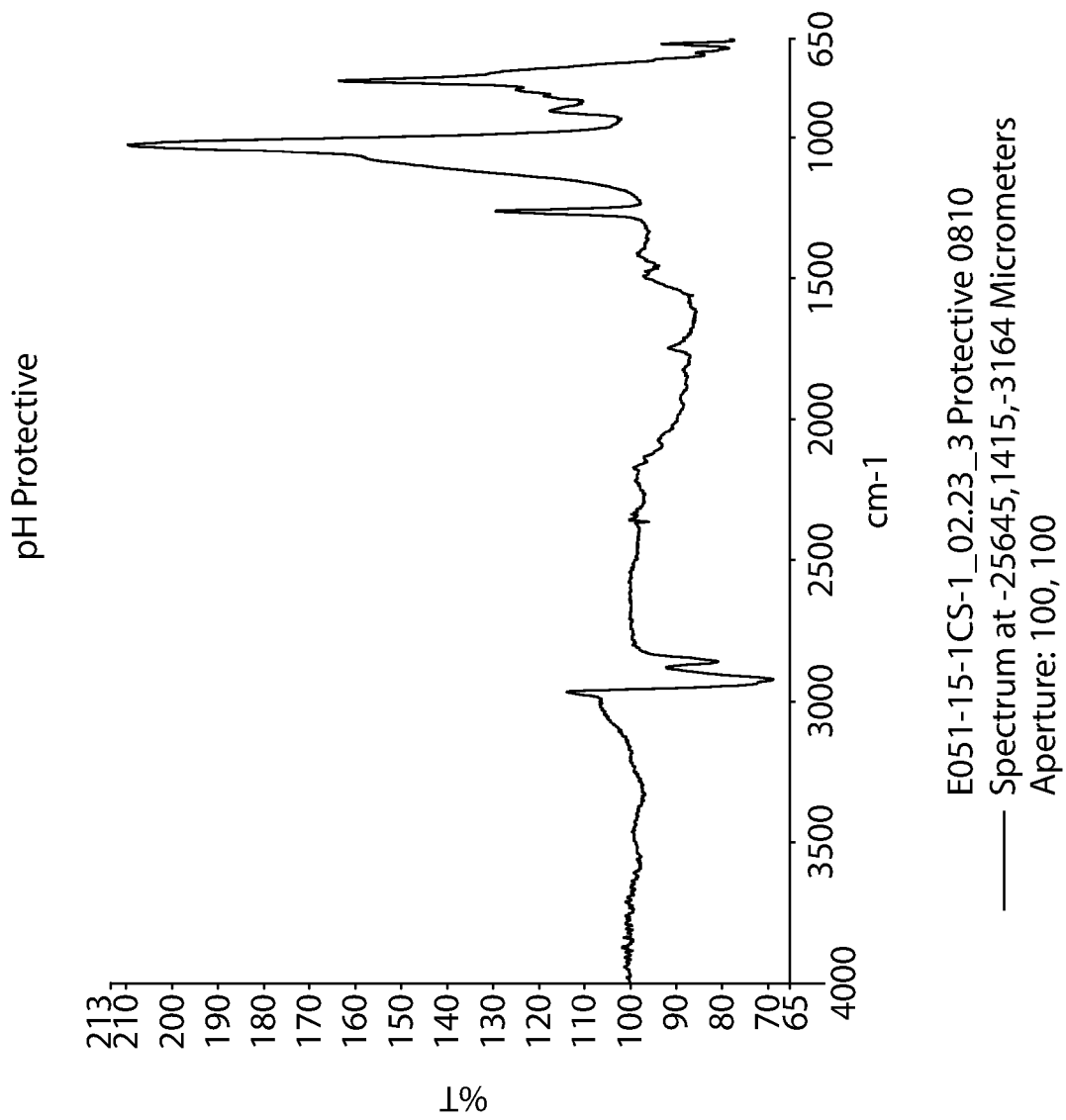
FIG. 13 is a Fourier-transform infrared spectrum representative of the pH protective coating or layer applied in Examples A and C, characterizing the coating chemistry.

The respective adhesive, barrier, and pH protective coatings or layers of representative syringes had the following properties. The adhesive coating or layer and the pH protective coating or layer of a representative syringe each had the empirical composition $SiO_{1.3}C_{0.8}H_{3.6}$, measured by XPS and Rutherford Backscattering. The barrier coating or layer of the representative syringe had the empirical composition $SiO_{2.0}$, measured by XPS. FIGS. 11-13 show representative FTIR plots of the respective adhesive coating or layer (FIG. 11), the barrier coating or layer (FIG. 12), and the pH protective coating or layer (FIG. 13).

Figure 14:
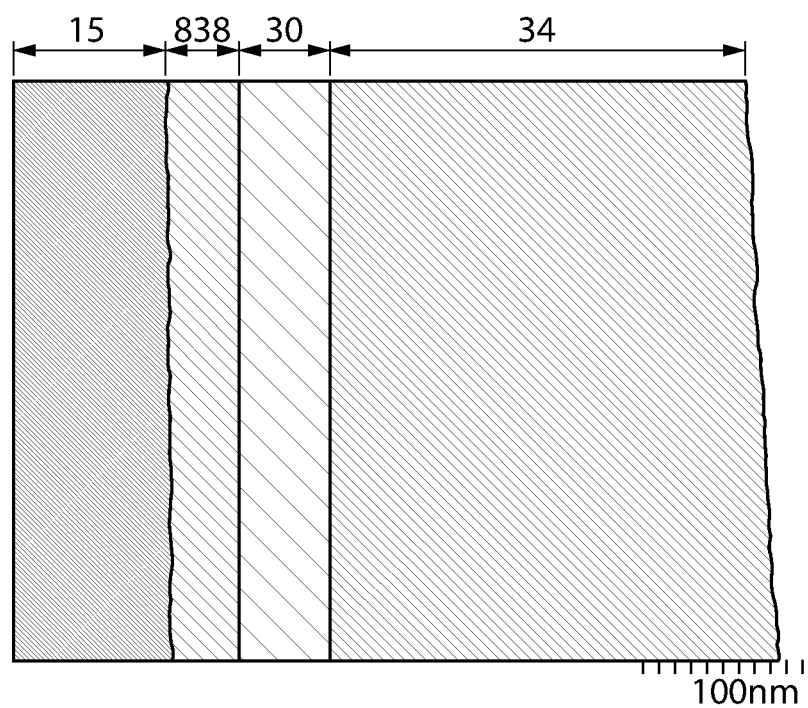
FIG. 14 is a TEM image of a cross-section of the coating applied in Example A, showing the relative thickness of, and sharp transitions between, the tie coating or layer, the barrier coating or layer, and the pH protective coating or layer.

A TEM measurement was made at one point half way down the length of a representative coated Type A syringe barrel, producing the image shown in FIG. 14. This measurement showed the adhesion coating or layer was 38 nm thick, the barrier coating or layer was 55 nm thick, and the pH protective coating or layer was 273 nm thick at that point. The coating thickness varied depending on the point of measurement, as is typical. The overall coating set of the syringe barrel was measured using Filmetrics Thin-Film Analyzer Model 205-0436 F40 spectral reflectance analysis, and found to be 572±89 nm thick, which is very consistent for a 1 mL syringe barrel.

For the Type C syringe barrels, the first three layers were formed and had the properties described for the Type A syringe barrel, then an additional PECVD lubricity coating or layer was applied in the same equipment, using the specific coating conditions of Table 6. The resulting PECVD lubricity coating has a thickness profile from less than 10 nm near the front (also known as the dispensing end) of the syringe barrel, where lubricity is not required, to about 12 nm about half way down the axial length of the barrel where lubricity is required only to reduce the plunger sliding force, to about 80 nm near the back of the syringe where lubricity is required to reduce both the breakout force and the plunger sliding force The Type B syringe barrels were commercial borosilicate glass syringe barrels, having a nominal maximum fill volume of 1 mL similar or identical to a pre-filled Ranibizumab syringe approved by the European Medicines Agency (EMA). The syringe barrel consists of borosilicate glass which was spray-coated with silicon oil-in-water emulsion and subsequently heat-fixed (so-called "baked silicone") (poster presentation by Clunas et al. at the 5th World Congress on Controversies in Ophthalmology, Mar. 20-23, 2014; poster presentation of Michaud et al. at the ARVO Annual Meeting 2014).

The three types of syringe barrels were filled as follows. 165 µl of a solution of the anti-VEGF antibody Ranibizumab containing 10 mg/ml of the antibody and histidine buffer, trehalose dihydrate, polysorbate 20, pH 5.5 was filled into the syringes as listed above in Table 1, then incubated at different temperatures for different periods.

Afterward, the samples were analyzed by RP-HPLC for the presence of hydrophilic and hydrophobic species, by cation exchange chromatography for the presence of acidic and basic variants of the antibody and by size exclusion chromatography for the presence of aggregates.

a) RP-HPLC Analysis

The protein samples from the syringes were loaded onto a ZORBAX 300SB-C18, 4.6×100 mm, 3.5 µm column to detect hydrophilic and hydrophobic impurities.

The protein was eluted with a gradient of eluent A (0.1% trifluoroacetic acid in water) and eluent B (0.1% trifluoroacetic acid in 70% acetonitrile, 20% 1-propanol and 10% water) according to Table 7:

TABLE 7

| Time [min] | Flow [mL/min] | Solvent composition Eluent A [%] | Solvent composition Eluent B [%] |
|---|---|---|---|
| 0 | 1.0 | 100 | 0 |
| 7 | 1.0 | 62.5 | 37.5 |
| 10 | 1.0 | 62.5 | 37.5 |

TABLE 7-continued

| Time [min] | Flow [mL/min] | Solvent composition Eluent A [%] | Solvent composition Eluent B [%] |
|---|---|---|---|
| 26 | 1.0 | 58.5 | 41.5 |
| 31 | 1.0 | 58.5 | 41.5 |
| 33 | 1.0 | 0 | 100 |
| 35 | 1.0 | 0 | 100 |
| 37 | 1.0 | 100 | 0 |
| 45 | 1.0 | 100 | 0 |

Eluted species were detected and displayed on a graph showing the concentration of the eluted species vs. time, at periods ranging from $T_0$ (storage time of zero days), to the indicated periods of weeks or months. The elution profile showed a main peak with the unmodified protein and some further peaks eluting before and after the main peak, representing hydrophilic and hydrophobic variants of the protein, respectively. The total area of all peaks as well as the areas of the single peaks were determined. Table 8 shows the percentage of the peak area for hydrophilic species in relation to the total peak area of the eluted species for the syringes of Table 1 incubated under the conditions indicated in Table 8.

TABLE 8

| Condition | Syringe Type | Hydrophilic species (%) |
|---|---|---|
| $T_0$ | A | 1.32 |
|  | B | 1.41 |
|  | C | 1.34 |
| 2W 25° C. | A | 1.52 |
|  | B | 1.55 |
|  | C | 1.53 |
| 2W 40° C. | A | 2.03 |
|  | B | 2.47 |
|  | C | 2.21 |
| 1M 25° C. | A | 1.87 |
|  | B | 1.65 |
|  | C | 1.56 |
| 1M 40° C. | A | 2.67 |
|  | B | 3.48 |
|  | C | 3.08 |
| 3M 5° C. | A | 1.39 |
|  | B | 1.43 |
|  | C | 1.51 |
| 3M 25° C. | A | 2.30 |
|  | B | 2.41 |
|  | C | 2.29 |
| 3M 40° C. | A | 7.68 |
|  | B | 10.65 |
|  | C | 8.11 |

W: weeks;
M: months b) Cation Exchange Analysis

The protein samples from the syringes were loaded onto a Dionex, BioLCProPac® WCX-10, 4.0×250 mm, 10 μm column to detect acidic and basic variants of the protein.

The protein was eluted with a gradient of mobile phase A (20 mM potassium phosphate buffer, pH 6.0) and mobile phase B (250 mM KCl, 20 mM potassium phosphate buffer, pH 6.0) according to Table 9:

TABLE 9

| Time [min] | Solvent composition [%-B] | Solvent composition [mM KCl] |
|---|---|---|
| 0 | 0 | 0 |
| 3 | 0 | 0 |
| 33 | 50 | 125 |
| 35 | 50 | 125 |
| 36 | 0 | 0 |
| 40 | 0 | 0 |

Eluted species were detected and displayed on a graph showing the concentration of the eluted species vs. time. The elution profile showed a main peak with the unmodified protein and some further peaks eluting before and after the main peak, representing acidic and basic variants of the protein, respectively. The total area of all peaks as well as the area of the single peaks was determined. Table 10 shows the percentage of the peak area for acidic variants and basic variants, respectively, in relation to the total peak area of the eluted species for the syringes of Table 1 incubated under the conditions indicated in Table 10.

TABLE 10

| Condition | Syringe Type | Acidic species [%] | Basic Species [%] |
|---|---|---|---|
| $T_0$ | A | 0.06 | 0.33 |
|  | B | 0.05 | 0.30 |
|  | C | 0.05 | 0.32 |
| 2W 25° C. | A | 0.16 | 0.56 |
|  | B | 0.26 | 0.51 |
|  | C | 0.19 | 0.61 |
| 2W 40° C. | A | 0.95 | 1.82 |
|  | B | 0.90 | 1.77 |
|  | C | 1.20 | 2.86 |
| 1M 25° C. | A | 0.34 | 0.67 |
|  | B | 0.41 | 0.65 |
|  | C | 0.47 | 0.97 |
| 1M 40° C. | A | 1.83 | 2.36 |
|  | B | 1.93 | 2.84 |
|  | C | 2.16 | 3.74 |
| 3M 5° C. | A | 0.15 | 0.48 |
|  | B | 0.23 | 0.54 |
|  | C | 0.14 | 0.47 |
| 3M 25° C. | A | 1.23 | 2.67 |
|  | B | 1.53 | 2.93 |
|  | C | 1.23 | 3.22 |
| 3M 40° C. | A | 7.95 | 6.72 |
|  | B | 9.44 | 10.38 |
|  | C | 7.02 | 9.58 |

W: weeks;
M: months c) Size Exclusion Chromatography

The protein samples from the syringes were loaded onto a YMC-Pack Diol-200, 5 μm, 20 nm (8.0×300 mm) column to detect aggregates of the protein.

The protein was eluted by isocratic elution using 0.1 M potassium phosphate and 0.2 M sodium chloride. Eluted species were detected and displayed on a graph showing the concentration of the eluted species vs. time. The elution profile showed a main peak with the non-aggregated protein and some further peaks of the protein representing aggregated forms of the protein. The area of all peaks was determined. Table 11 shows the percentage of peak area for the aggregates in relation to the total peak area of the eluted species for the syringes of Table 1 incubated under the conditions indicated in Table 11.

TABLE 11

| Conditions | Syringe Type | Aggregates [%] |
|---|---|---|
| $T_0$ | A | 0.04 |
|  | B | 0.04 |
|  | C | 0.05 |
| 2W 25° C. | A | 0.08 |
|  | B | 0.10 |
|  | C | 0.08 |
| 2W 40° C. | A | 0.14 |
|  | B | 0.14 |
|  | C | 0.11 |
| 1M 25° C. | A | 0.08 |
|  | B | 0.08 |
|  | C | 0.10 |
| 1M 40° C. | A | 0.17 |
|  | B | 0.24 |
|  | C | 0.16 |
| 3M 5° C. | A | 0.07 |
|  | B | 0.06 |
|  | C | 0.07 |
| 3M 25° C. | A | 0.12 |
|  | B | 0.18 |
|  | C | 0.12 |
| 3M 40° C. | A | 0.42 |
|  | B | 0.90 |
|  | C | 0.40 |

W: weeks;
M: months

Tables 8, 10, and 11 are interpreted as follows. In each case, higher values for the same storage conditions (other than $T_0$, which simply represents random error) are less favorable, indicating the presence of more decomposition products, while lower values for the same storage conditions indicate fewer decomposition products and thus better storage stability. The decomposition products are hydrophilic and hydrophobic species in Table 8, basic species or acidic species in Table 10, and aggregates in Table 11.

Table 8, testing for Hydrophilic species, shows that Syringe Types A and C of the present invention performed better than Syringe Type B in almost every instance, including all of the 3-month storage times.

Table 10, testing for Acidic species, shows that Syringe Type A according to the invention performed better than Syringe Type B in almost every instance, including all of the 3-month storage times. Syringe Type C was less consistently better, although in a majority of the tests, and all of the 3-month storage tests, it performed better than Syringe Type B. Table 10, testing for Basic species, shows that Syringe Type A in a majority of the tests, and all of the 3-month storage tests, performed better than Syringe Type B.

Table 11, testing for Aggregates, shows that Syringe Types A and C according to the invention performed the same as or better than the Syringe Type B, and under the more stringent 3-month tests at higher temperatures and humidities, significantly better than Syringe Type B.

Looking at the results overall, syringe types A and C according to the invention performed the same as or better than the commercially approved syringe type B, which is very surprising.

Examples D and E—Determination of Ranibizumab Stability in Glass Vs. Coated COP Pharmaceutical Packages Sample Preparation:

165 µl of a solution containing 40 mg/ml of the VEGF antagonist Aflibercept and 10 mM histidine buffer, 40 mM sodium chloride, 5% (w/v) sucrose, 0.03% (w/v) polysorbate 20, pH 6.2 was filled into the syringes as listed in Table 12.

The syringes as listed above in Table 12 were incubated at 5° C., 25° C./60% relative humidity and 40° C./75% relative humidity for one month and 3 months.

Afterward, the samples were analyzed by UV-Vis for protein concentration, by size exclusion chromatography (SEC) and asymmetric flow field-flow fractionation (AF4) for the presence of high molecular weight species (HMWS), by non-reduced sodium dodecyl sulfate polyacrylamide gel electrophoresis (SDS-PAGE) for the presence of fragments and HMWS and by reduced peptide mapping for the presence of deamidation. Isoelectric focusing (IEF) was used to analyze samples for chemical modifications which results in charge variants of Aflibercept. Also pH was monitored within the whole incubation period.

TABLE 12

| No. | Syringe size | Syringe barrel | Syringe type | Silicone level [mg] | Stopper coating |
|---|---|---|---|---|---|
| D | 1.0 mL | $SiO_2$ coated cycloolefin polymer | Staked needle 27 G × ½" | L-OMCTS (no silicone) | Fluoropolymer (Flurotec) |
| E | 1.0 ml | Borosilicate glass | Luer cone | 0.16 (baked-on) | Fluoropolymer (Flurotec) |

During the complete stability program in all samples no significant change as well in protein concentration (spectrophotometric quantification at 280 nm; n=3) and pH (n=2) was detected.

AF4:

The asymmetric flow field flow fractionation (AF4) is a technique to identify and quantify higher molecular weight species of Aflibercept based on their size. This separation is obtained by the difference in mobility (diffusion coefficient) in the flow field induced by the liquid flow across the channel. In combination with MALS (multi angle light scattering) and UV (280 nm) as concentration-dependent detector the Aflibercept aggregates can be characterized and quantified.

20 µg Aflibercept was loaded onto a 15.5 cm separation channel 15.5 cm (short channel) combined with a W490 separation spacer (both Wyatt Technology) and a PLGC 10 kD SC-5 Membrane (Millipore). The protein was eluted using 0.1 M sodium phosphate (pH 6.0) and 0.02% sodium azide according to elution conditions shown in Table 13 representing the cross flow and focus flow during the separation (channel flow: 0.8 mL/min).

Eluted species were detected at a wavelength of 280 nm and displayed on a graph showing the concentration of the eluted species vs. time. The elution profile showed a main peak with the non-aggregated protein and some further peaks of the protein representing higher molecular weight forms of the protein. The corresponding molecular weights were calculated with a MALLS detector.

TABLE 13

| Step | Delta t [min] | Time [min] | Mode | $X_{Start}$ [mL/min] | $X_{End}$ [mL/min] | FF [mL/min] |
|---|---|---|---|---|---|---|
| 1 | 4.0 | 4.0 | Elution | 1.5 | 1.5 | — |
| 2 | 1.0 | 5.0 | Focus | — | — | 2.0 |
| 3 | 2.0 | 7.0 | Focus + Inj. | — | — | 2.0 |
| 4 | 1.0 | 8.0 | Focus | — | — | 2.0 |

TABLE 13-continued

| Step | Delta t [min] | Time [min] | Mode | $X_{Start}$ [mL/min] | $X_{End}$ [mL/min] | FF [mL/min] |
|---|---|---|---|---|---|---|
| 5 | 32.0 | 40.0 | Elution | 1.5 | 1.5 | — |
| 6 | 10.0 | 50.0 | Elution | 1.5 | 0.2 | — |
| 7 | 10.0 | 60.0 | Elution | 0.2 | 0.2 | — |
| 8 | 10.0 | 70.0 | Elution + Inj. | 0.2 | 0.0 | — |
| 9 | 10.0 | 80.0 | Elution + Inj. | 0.0 | 0.0 | — |

Table 14 shows the percentage of peak areas for the higher molecular weight species in relation to the total peak areas of the eluted species for the 1 and 3 months 40° C./75% relative humidity incubated syringes of Table 12. Each sample was examined in duplicate measurements unless otherwise noted.

All other temperatures (5° C. and 25° C./60% relative humidity) showed no significant increase of higher molecular weight species during storage compared to the starting material.

TABLE 14

| Condition | Syringe | HMWS [%] | SD [%] |
|---|---|---|---|
| $T_0$ | D | 1.4 | n.a.*) |
|  | E | 1.1 | n.a.*) |
| 1M 40° C. | D | 10.8 | n.a.*) |
|  | E | 10.7 | 0.1 |
| 3M 40° C. | D | 28.6 | 0.2 |
|  | E | 26.8 | 0.7 |

*)only single measurement

The generation of HMWS determined by AF4-MALS was highly comparable during incubation at 40° C./75 relative humidity between the two syringes E (glass syringe) and D (COP) in the period up to 3 months. Both the identities of the higher molecular weight species and the temperature dependent kinetics were comparable between the two primary packaging systems.

SEC:

The protein samples from the syringes were loaded onto a TSKgel G3000SWXL, (Tosoh, 300×7.8 mm, 5 μm) column to detect high molecular weight species of Aflibercept by size exclusion chromatography.

The protein was eluted by isocratic elution using 0.02 M sodium phosphate (pH 6.0) and 0.8 M sodium chloride at a flow rate of 1.0 mL/min at 25° C. Eluted species were detected at a wavelength of 214 nm and displayed on a graph showing the concentration of the eluted species vs. time. The elution profile showed a main peak with the non-aggregated protein and some further peaks of the protein representing higher molecular weight forms of the protein. The area of all peaks was determined. Table 15 shows the percentage of peak area for the aggregates in relation to the total peak area of the eluted species for the syringes of Table 12. Each sample was examined in duplicate measurements.

TABLE 15

| Condition | Syringe | HMWS [%] | SD [%] |
|---|---|---|---|
| $T_0$ | D | 2.18 | 0.02 |
|  | E | 2.20 | 0.01 |
| 1M 5° C. | D | 2.25 | 0.00 |
|  | E | 2.31 | 0.01 |
| 3M 5° C. | D | 2.36 | 0.01 |
|  | E | 2.38 | 0.01 |
| 2W 25° C. | D | 2.47 | 0.00 |
|  | E | 2.45 | 0.01 |
| 1M 25° C. | D | 2.55 | 0.01 |
|  | E | 2.55 | 0.01 |
| 3M 25° C. | D | 3.12 | 0.01 |
|  | E | 3.03 | 0.01 |
| 0.5M 40° C. | D | 9.94 | 0.04 |
|  | E | 9.80 | 0.02 |
| 1M 40° C. | D | 15.68 | 0.06 |
|  | E | 15.58 | 0.01 |
| 3M 40° C. | D | 35.82 | 0.19 |
|  | E | 33.71 | 0.01 |

The generation of HMWS determined by SEC was highly comparable during all incubation parameters (temperature, storage time) between the two syringes E (glass syringe) and D (COP). Both the identities of the higher molecular weight species and the temperature dependent kinetics were comparable between the two primary packaging systems.

Non-Reduced SDS-PAGE:

By non-reduced SDS-PAGE physical modifications like fragmentation and oligomerization of Aflibercept in the different syringe systems according to Table 12 were determined.

The SDS-PAGE was performed under non-reducing conditions in a 4-12% Tris-Glycine gel. Samples were pre-diluted to 0.4 mg/ml with water and further diluted to 0.2 mg/ml with SDS sample buffer. The samples were incubated at 95° C. for 5 min.

After the run the gel was rinsed three times with 100 mL deionized water and dyed with Coomassie overnight at room temperature. After discoloration the gel was scanned and analyzed using QuantityOne Software.

Figure 15:
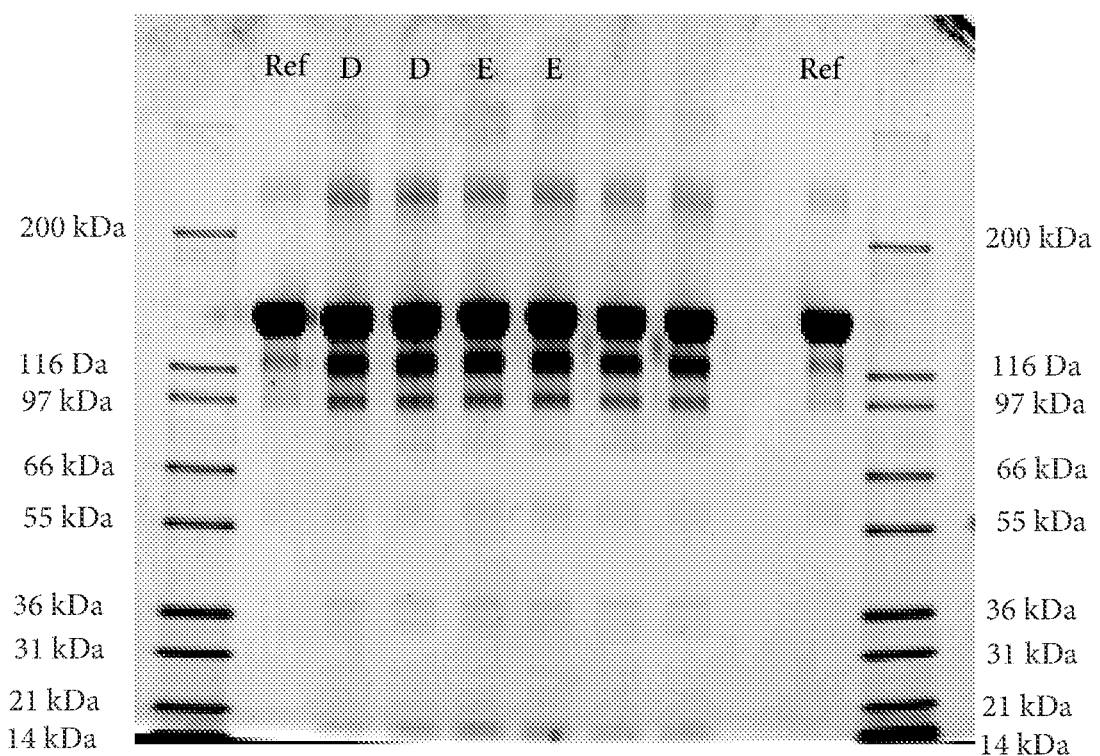
FIG. 15 is a non-reduced SDS-PAGE analysis of Examples D and E incubated for three months at 40° C./75% relative humidity.

The running conditions were as follows:
Voltage: 125 V
Current: 35 mA
Power: 5 W
Time: 130 min Non-reduced SDS-PAGE was performed at all temperatures during the complete incubation period of 3 months. Storing the samples at 5° C. did not lead to significant changes of the banding pattern in all primary packaging systems, no generation of new impurity bands or significant increment of existing impurity bands could be detected in both syringe materials over the whole incubation period. Storing the samples at 25° C./60% relative humidity led to stronger impurity bands, the results of the non-reduced SDS PAGE analysis of 3 months incubated samples at 40° C./75% relative humidity are shown in FIG. 15.

In the non-reduced SDS-PAGE analysis of all samples incubated for three months at 40° C./75 relative humidity bands representing fragments and higher molecular weight species of Aflibercept were visible. The generation of fragments and HMWS during the 3 months incubation was highly comparable as well in the kinetics and the identity of the impurities in both primary packaging systems shown in Table 12.

IEF:

Isoelectric focusing (IEF) separates different isoforms of Aflibercept due to differences in their isoelectric points because of e.g. deamidation. The ready-to-use IEF gel (Focus Gel (pH 6-11) from Serva, No. 43329.01) contains a pH gradient within the gel. After application, proteins migrate due to their net charge in the pH gradient until they reach the pH equivalent to their isoelectric point (IEP, IP).

Aflibercept samples were diluted to 0.5 mg/ml with ultrapure water. 10 µl thereof equal to 5 µg Aflibercept were applied onto the focus gel. Each sample was analyzed as duplicate.

After the run the proteins were fixed for 60 minutes in a solution containing 12% (w/v) trichloroacetic acid and 3.5% 5-sulfosalicyl acid dihydrate (w/v), rinsed three times with deionized water and dyed with Coomassie overnight at room temperature. After discoloration with 20% ethanol the gel was scanned with a GS 800 densitometer from BioRad and analyzed.

Table 16 shows the focusing conditions:

TABLE 16

| Phase | Time (min) | Power (W) | Current (mA) | Voltage (V) |
|---|---|---|---|---|
| Pre focusing | 20 | 10 | 50 | 1000 |
| Sample entrance | 30 | 10 | 30 | 500 |
| Isoelectric focusing | 90 | 20 | 18 | 1500 |
| Sharpening | 30 | 25 | 15 | 2000 |

In the IEF no change in the banding pattern of Aflibercept compared to the reference could be detected in all primary packaging systems after one month storage at all temperatures. After 3 months only 5° C. and 25° C./60% incubated samples complied with the reference and showed no alteration to the starting material. Samples incubated at 40° C./75% relative humidity comprised a comparable shift to acidic species in all tested primary packaging materials, there was no difference with regard to the different primary packaging materials shown in Table 12.

Reduced Peptide Mapping:

By reduced peptide mapping the purity of Aflibercept with regard to deamidation was analyzed after digestion with trypsin and liquid chromatography coupled to mass spectrometry (LC-MS).

After reduction and alkylation, the protein was submitted to enzymatic cleavage with trypsin. The resulting peptides were analyzed by RP-UPLC-MS. During chromatography the peptides were eluted by changing the mobile phase from highly polar (trifluoroacetic acid in water) to less polar (trifluoroacetic acid in acetonitrile) and analyzed by mass spectrometry (Xevo G2-XS QTOF). The peptide data was processed and compared with the theoretical protein sequence and a reference sample to detect oxidations and deamidations.

Syringes shown in Table 12 were analyzed as single measurement after 3 months incubation at 5° C., 25° C./60% relative humidity and 40° C./75 relative humidity and compared to corresponding values for the filled syringes at $T_0$.

Samples were diluted with denaturation buffer (50 mM Tris(hydroxymethyl)aminomethane) to a Aflibercept concentration of 1.25 mg/mL. 80 µl of the diluted samples were mixed with 10 µl of 0.5% RapiGest (from Waters, solved in 50 mM Tris(hydroxymethyl)aminomethane) and incubated 5 minutes at 95° C. 4.5 µl of 0.02 M DTT (solved in 50 mM Tris(hydroxymethyl)-aminomethane) were added for reduction and incubated for 30 minutes at 37° C. For Aflibercept digestion 5 µl of a 1 mg/mL Trypsin solution (solved in 50 mM acetic acid) were added and incubated for further 3 hours at 37° C. The reaction was stopped with 20 µl of 2% (v/v) trifluoroacetic acid and an incubation for 30 minutes at 37° C. The supernatant was diluted to 0.125 mg/mL with 50 mM Tris(hydroxymethyl)-aminomethane for analysis of the peptides.

UPLC Parameters:

The digested protein samples from the syringes were loaded onto an ACQUITY UPLC-CSH C-18 column from Waters, 100 mm×2.1 mm, 1.7 µm. 0.25 µg of the digested samples were eluted at 65° C. with a gradient of eluent A (water), eluent B (acetonitrile), eluent C (0.25% trifluoroacetic acid) and D (n-propanol) according to the following Table:

TABLE 17

| Time [minutes] | Eluent A [%] | Eluent B [%] | Eluent C [%] | Eluent D [%] |
|---|---|---|---|---|
| 0.0 | 89.0 | 1.0 | 10.0 | 0.0 |
| 2.5 | 89.0 | 1.0 | 10.0 | 0.0 |
| 5.0 | 80.0 | 8.0 | 10.0 | 2.0 |
| 50.0 | 57.5 | 26.0 | 10.0 | 6.5 |
| 52.0 | 0.0 | 72.0 | 10.0 | 18.0 |
| 54.0 | 0.0 | 72.0 | 10.0 | 18.0 |
| 56.0 | 89.0 | 1.0 | 10.0 | 0.0 |
| 60.0 | 89.0 | 1.0 | 10.0 | 0.0 |

Method Parameters for Mass Spectrometry:

| | | | |
|---|---|---|---|
| Ionisation type: | ESI | Polarity: | Positive |
| Analyser mode: | Sensitivity | Experiment type: | MS |
| Start Mass: | 50 m/z | End Mass: | 2000 m/z |
| Source Temperature: | 120° C. | Cone Gas Flow: | 30 L/h |
| Desolvation Temperature: | 450° C. | Desolvation Gas Flow: | 1000 L/h |
| Capillary Voltage: | 3.0 kV | Scan Time: | 0.5 s |
| Cone Voltage: | 35 V | | |

LockSpray Profile
Reference Compound: Leucine Enkephalin
MS Lock mass: 556.2766 m/z
Scan Time: 0.5 s
Interval: 30 s 6 deamidations of Aflibercept could be identified in the peptides (1:T10_AS12; 1:T11; 1:T10_AS12; 1:T12_AS3; 1:T12_AS3; 1:T30_AS12; 1:T30_AS?; 1:T33_AS14) and were summed up for evaluation of the total deamidation (see Table 6)

TABLE 18

| Condition | Syringe | Total deamidations [%] |
|---|---|---|
| $T_0$ | D | 31.9 |
| | E | 35.3 |
| 3M 5° C. | D | 29.3 |
| | E | 36.8 |
| 3M 25° C. | D | 40.8 |
| | E | 44.0 |
| 3M 40° C. | D | 88.9 |
| | E | 92.0 |

The increase of deamidation was temperature dependent. Both syringe systems D and E comprised a comparable increase of deamidation in the stability program.

From the results shown it is apparent that the stability of Aflibercept in the pre-filled plastic syringe of the present invention (syringe D) is at least comparable with the stability in the glass syringes (syringe E) under the conditions tested.

The invention claimed is:

1. A pre-filled pharmaceutical package comprising a liquid formulation of a VEGF-antagonist, wherein the pre-filled pharmaceutical package comprises:

a wall comprising a cyclic olefin polymer, having an interior surface enclosing at least a portion of a lumen;

a tie coating or layer on the wall interior surface comprising $SiO_xC_yH_z$, in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS);

a barrier coating or layer of $SiO_x$, in which x is from about 1.5 to about 2.9 as measured by XPS, the barrier coating or layer positioned between the tie coating or layer and the lumen;

a pH protective coating or layer of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS, positioned between the barrier coating or layer and the lumen;

a lubricity coating or layer positioned between the pH protective coating or layer and the lumen, wherein the lubricity coating or layer has the atomic proportions SiOxCyHz, in which x is from about 0.5 to about 2.4 as measured by XPS, y is from about 0.6 to about 3 as measured by XPS, and z is from about 2 to about 9 as measured by at least one of RBS or HFS;

a liquid formulation of a VEGF-antagonist in the lumen; and a closure closing the lumen;

wherein the VEGF antagonist is Ranibizumab.

2. The prefilled pharmaceutical package according to claim 1, in which the liquid formulation of Ranibizumab in the lumen comprises Ranibizumab at a concentration of 6 or 10 mg/ml.

3. The pre-filled pharmaceutical package according to claim 1, having a nominal maximum fill volume of 0.5 or 1 mL.

4. The pre-filled pharmaceutical package according to claim 1, in which the liquid formulation of Ranibizumab contains no more than 50 particles ≥10 μm diameter per mL, no more than 5 particles ≥25 μm diameter per mL, and/or no more than 2 particles ≥50 μm diameter per mL, during shelf life, measured by microscopic inspection.

5. The pre-filled pharmaceutical package according to claim 1, which is free of baked-on silicone.

6. The pre-filled pharmaceutical package according to claim 1, which is terminally sterilized.

7. The pre-filled pharmaceutical package according to claim 1, in which the liquid formulation of Ranibizumab in the lumen forms an equal or smaller area % of basic decomposition species, after storage of the pharmaceutical package at 5° C. for three months, than a glass pharmaceutical package of the same volumetric capacity, internally coated with baked-on silicone.

8. The pre-filled pharmaceutical package according to claim 1, in which the liquid formulation of Ranibizumab in the lumen forms an equal or smaller area % of acidic decomposition species, after storage of the pharmaceutical package at 5° C. for three months, than a glass pharmaceutical package of the same volumetric capacity, internally coated with baked-on silicone.

9. The pre-filled pharmaceutical package according to claim 1, in which the Ranibizumab retains its biological activity when stored at a temperature of 2 to 8° C. for at least six months.

10. The pre-filled pharmaceutical package according to claim 1, being a syringe.

11. The pre-filled pharmaceutical package according to claim 10, comprising a plunger which comprises a side surface slidable along the wall, wherein at least a portion of the side surface comprises a fluoropolymer lubricity coating or layer abutting the wall.

12. The pre-filled pharmaceutical package according to claim 10, having a breakout force less than or equal to 15N for initiating travel of the stopper in the lumen.

13. The pre-filled pharmaceutical package according to claim 10, having a plunger sliding force less than or equal to 15N for advancing the stopper in the lumen.

14. The pre-filled pharmaceutical package of claim 1 for use in administering a liquid formulation of a VEGF-antagonist to a patient having an ocular disease.

15. The pre-filled pharmaceutical package for the use according to claim 14, wherein the ocular disease is selected from the group consisting of age-related macular degeneration (AMD), visual impairment due to diabetic macular edema (DME), visual impairment due to macular edema secondary to retinal vein occlusion (branch RVO or central RVO), or visual impairment due to choroidal neovascularization (CNV) secondary to pathologic myopia.

16. The pre-filled pharmaceutical package for the use according to claim 14, wherein the VEGF antagonist is Ranibizumab which is administered in a volume of 0.05 mL.

17. A liquid formulation of a VEGF-antagonist in a pre-filled pharmaceutical package according to claim 1, in which the liquid formulation of Ranibizumab has been adjusted to pH 5.5 with HCl.

18. A liquid formulation of a VEGF-antagonist in a pre-filled pharmaceutical package according to claim 1, in which the liquid formulation of Ranibizumab in the lumen comprises, per mL of formulation:

6 or 10 mg. Ranibizumab;
100 mg. α,α-trehalose dihydrate;
0.32 mg. L-histidine
1.66 mg. L-histidine hydrochloride monohydrate;
0.1 mg Polysorbate 20; and
water for injection qs to 1 mL.

19. Kit comprising one or more pre-filled pharmaceutical packages according to claim 1.

* * * * *